(12) United States Patent
Georges et al.

(10) Patent No.: US 11,382,969 B2
(45) Date of Patent: *Jul. 12, 2022

(54) VACCINES AGAINST HEPATITIS B VIRUS

(71) Applicant: Altimmune UK Limited, London (GB)

(72) Inventors: Bertrand Victor Gilbert Georges, London (GB); Carlton Bradley Brown, London (GB)

(73) Assignee: Altimmune UK LTD, Leeds (GB)

( * ) Notice: Subject to any disclaimer, the term of this patent is extended or adjusted under 35 U.S.C. 154(b) by 110 days.

This patent is subject to a terminal disclaimer.

(21) Appl. No.: 16/423,149

(22) Filed: May 27, 2019

(65) Prior Publication Data

US 2020/0016263 A1 Jan. 16, 2020

Related U.S. Application Data

(62) Division of application No. 14/655,041, filed as application No. PCT/GB2013/053410 on Dec. 20, 2013, now Pat. No. 10,300,132.

(30) Foreign Application Priority Data

Dec. 24, 2012 (GB) ..................................... 1223386

(51) Int. Cl.
| | | |
|---|---|---|
| *A61K 39/29* | (2006.01) |
| *A61K 39/12* | (2006.01) |
| *C12N 7/00* | (2006.01) |
| *A61K 45/06* | (2006.01) |
| *C07K 14/005* | (2006.01) |
| *A61K 39/00* | (2006.01) |

(52) U.S. Cl.
CPC ............ *A61K 39/292* (2013.01); *A61K 39/12* (2013.01); *A61K 45/06* (2013.01); *C07K 14/005* (2013.01); *C12N 7/00* (2013.01); *A61K 2039/55* (2013.01); *A61K 2039/572* (2013.01); *A61K 2039/58* (2013.01); *A61K 2039/60* (2013.01); *A61K 2039/70* (2013.01); *C12N 2730/10122* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| | | | | |
|---|---|---|---|---|
| 6,607,727 | B1 * | 8/2003 | Chisari ................ | C07K 14/005 424/227.1 |
| 9,119,811 | B2 | 9/2015 | Brown et al. | |
| 2007/0059799 | A1 | 3/2007 | Sette et al. | |
| 2010/0183650 | A1 | 7/2010 | Bonnet et al. | |
| 2012/0034259 | A1 | 2/2012 | Bonnet et al. | |
| 2012/0251569 | A1 | 10/2012 | Martin et al. | |
| 2012/0315293 | A1 | 12/2012 | Bonnet et al. | |
| 2013/0330382 | A1 | 12/2013 | Brown et al. | |
| 2015/0112042 | A1 | 4/2015 | Bonnet et al. | |
| 2016/0051661 | A1 | 2/2016 | Brown et al. | |

FOREIGN PATENT DOCUMENTS

| | | |
|---|---|---|
| WO | 1993003753 A1 | 3/1993 |
| WO | 1995003777 A1 | 2/1995 |
| WO | WO 95/03777 * | 2/1995 |
| WO | 0219986 A1 | 3/2002 |
| WO | 2005099752 A2 | 10/2005 |
| WO | 2012090002 A1 | 7/2012 |

OTHER PUBLICATIONS

Krafft et al. 1998 Biochimie vol. 80, pp. 489-514 (Year: 1998).*
Desmond et al. Antiviral Therapy 13: 161-175 (Year: 2008).*
Cao, et al. "Characterization of HLA DR1 3-restricted CD4+ T cell epitopes of hepatitis B core antigen associated with self-limited, acute hepatitis B" Journal of General Virology, 2002, 83(Pt 12):3023-3033.
Castelli, F.A., et al., HLA-DP4, the most frequent HLA II molecule, defines a new supertype of peptide-binding specificity, J Immunology, 2002;169(12):6928-6934.
Database UniProt [Online], "Subname: Full=Precore/core protein;" retrieved from EBI accession No. UNIPROT: Q9DH31, Mar. 2001.
Greenbaum, J., et al., Functional classification of class II human leukocyte antigen (HLA) molecules reveals seven different supertypes and a surprising degree of repertoire sharing across supertypes, Immunogenetics, 2011;63(6):325-335.
International Preliminary Report on Patentability and Written Opinion of the International Searching Authority dated Jun. 30, 2015, which issued during prosecution of International Application No. PCT/GB2013/053410.
International Search Report dated Jun. 3, 2014, which issued during prosecution of International Application No. PCT/GB2013/053410.
Krafft, MP., et al., Highly fluorinated amphiphiles and colloidal systems, and their applications in the biomedical field. A contribution, 1998, Biochimie vol. 80, pp. 489-514.

(Continued)

*Primary Examiner* — Shanon A. Foley
*Assistant Examiner* — Myron G Hill
(74) *Attorney, Agent, or Firm* — Koren Anderson; Duane Morris LLP

(57) ABSTRACT

A pharmaceutical composition comprising at least two peptides of from 15 to 60 amino acids in length, selected from peptides comprising a sequence of at least 15 contiguous amino acids of one of the sequences shown in SEQ ID NOs: 1 to 4 or of a sequence having at least 80% identity to one of the sequences shown in SEQ ID NOs: to 4, wherein each peptide comprises at least one CD8+ T-cell epitope and/or at least one CD4+ T-cell epitope and wherein each peptide elicits a response in peripheral blood mononuclear cells (BMC) from at least one chronically infected HBV individual in an 10 in vitroassay.

19 Claims, 15 Drawing Sheets

Specification includes a Sequence Listing.

(56) References Cited

OTHER PUBLICATIONS

Lund, O., et al., Definition of supertypes for HLA molecules using clustering of specificity matrices, Immunogenetics, 2004;55(12):797-810.

Sette, A., et al., Nine major HLA class I supertypes account for the vast preponderance of HLA-A and -B polymorphism, Immunogenetics, 1999;50(3-4):201-212.

Texier, C., et al., Complementarity and redundancy of the binding specificity of HLA-DRB1, -DRB3, -DRB4 and -DRB5 molecules, European Journal of Immunology, 2001;31(6):1837-1846.

Texier, C., et al., HLA-DR restricted peptide candidates for bee venom immunotherapy, Journal of Immunology, 2000;164(6):3177-3184.

Wilson, C.C., et al., Identification and antigenicity of broadly cross-reactive and conserved human immunodeficiency virus type 1-derived helper T-lymphocyte epitopes, J Virology, 2001;75(9):4195-4207.

\* cited by examiner

SEQUENCE LISTING

<160> NUMBER OF SEQ ID NOS: 222

<210> SEQ ID NO 1
<211> LENGTH: 94
<212> TYPE: PRT
<213> ORGANISM: Artificial Sequence
<220> FEATURE:
<223> OTHER INFORMATION: HBV CONSENSUS SEQUENCE

<400> SEQUENCE: 1

Gln Gln Phe Val Gly Pro Leu Thr Val Asn Glu Lys Arg Arg Leu Lys
1               5                   10                  15

Leu Ile Met Pro Ala Arg Phe Tyr Pro Asn Val Thr Lys Tyr Leu Pro
                20                  25                  30

Leu Asp Lys Gly Ile Lys Pro Tyr Tyr Pro Glu His Val Val Asn His
            35                  40                  45

Tyr Phe Gln Thr Arg His Tyr Leu His Thr Leu Trp Lys Ala Gly Ile
        50                  55                  60

Leu Tyr Lys Arg Glu Thr Thr Arg Ser Ala Ser Phe Cys Gly Ser Pro
65                  70                  75                  80

Tyr Ser Trp Glu Gln Glu Leu Gln Ser Cys Trp Trp Leu Gln
                85                  90

<210> SEQ ID NO 2
<211> LENGTH: 216
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (183)..(183)
<223> OTHER INFORMATION: C OR S

<400> SEQUENCE: 2

Cys Thr Glu His Gly Glu His His Ile Arg Ile Pro Arg Thr Pro Ala
1               5                   10                  15

Arg Val Thr Gly Gly Val Phe Leu Val Asp Lys Asn Pro His Asn Thr
                20                  25                  30

Thr Glu Ser Arg Leu Val Val Asp Phe Ser Gln Phe Ser Arg Gly Asn
            35                  40                  45

Thr Arg Val Ser Trp Pro Lys Phe Ala Val Pro Asn Leu Gln Ser Leu
        50                  55                  60

```
Thr Asn Leu Leu Ser Ser Asn Leu Ser Trp Leu Ser Leu Asp Val Ser
 65                  70                  75                  80

Ala Ala Phe Tyr His Ile Pro Leu His Pro Ala Ala Met Pro His Leu
                 85                  90                  95

Leu Val Gly Ser Ser Gly Leu Ser Arg Tyr Val Ala Arg Leu Ser Ser
            100                 105                 110

Asn Ser Arg Ile Ile Asn Asn Gln His Gly Thr Met Gln Asn Leu His
        115                 120                 125

Asp Ser Cys Ser Arg Asn Leu Tyr Val Ser Leu Met Leu Leu Tyr Lys
    130                 135                 140

Thr Tyr Gly Arg Lys Leu His Leu Tyr Ser His Pro Ile Ile Leu Gly
145                 150                 155                 160

Phe Arg Lys Ile Pro Met Gly Val Gly Leu Ser Pro Phe Leu Leu Ala
                165                 170                 175

Gln Phe Thr Ser Ala Ile Xaa Ser Val Val Arg Arg Ala Phe Pro His
            180                 185                 190

Cys Leu Ala Phe Ser Tyr Met Asp Asp Val Val Leu Gly Ala Lys Ser
        195                 200                 205

Val Gln His Leu Glu Ser Leu Tyr
    210                 215

<210> SEQ ID NO 3
<211> LENGTH: 109
<212> TYPE: PRT
<213> ORGANISM: Artificial Sequence
<220> FEATURE:
<223> OTHER INFORMATION: HBV CONSENSUS SEQUENCE

<400> SEQUENCE: 3

Ala Cys Phe Ala Arg Ser Arg Ser Gly Ala Lys Leu Ile Gly Thr Asp
  1               5                  10                  15

Asn Ser Val Val Leu Ser Arg Lys Tyr Thr Ser Phe Pro Trp Leu Leu
                 20                  25                  30

Gly Cys Ala Ala Asn Trp Ile Leu Arg Gly Thr Ser Phe Val Tyr Val
             35                  40                  45

Pro Ser Ala Leu Asn Pro Ala Asp Asp Pro Ser Arg Gly Arg Leu Gly
         50                  55                  60

Leu Tyr Arg Pro Leu Leu Arg Leu Pro Phe Arg Pro Thr Thr Gly Arg
 65                  70                  75                  80

Thr Ser Leu Tyr Ala Val Ser Pro Ser Val Pro Ser His Leu Pro Asp
                 85                  90                  95

Arg Val His Phe Ala Ser Pro Leu His Val Ala Trp Arg
            100                 105

<210> SEQ ID NO 4
<211> LENGTH: 210
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (41)..(41)
<223> OTHER INFORMATION: S OR T
<220> FEATURE:
<221> NAME/KEY: MISC_FEATURE
<222> LOCATION: (90)..(90)
<223> OTHER INFORMATION: C OR S

<400> SEQUENCE: 4
```

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Xaa Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Xaa Trp Gly Glu Leu Met Thr
                85                  90                  95

Leu Ala Thr Trp Val Gly Ser Asn Leu Glu Asp Pro Ala Ser Arg Asp
            100                 105                 110

Leu Val Val Ser Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser
    210

<210> SEQ ID NO 5
<211> LENGTH: 53
<212> TYPE: PRT
<213> ORGANISM: Artificial Sequence
<220> FEATURE:
<223> OTHER INFORMATION: HBV CONSENSUS SEQUENCE

<400> SEQUENCE: 5

Gln Gln Phe Val Gly Pro Leu Thr Val Asn Glu Lys Arg Arg Leu Lys
1               5                   10                  15

Leu Ile Met Pro Ala Arg Phe Tyr Pro Asn Val Thr Lys Tyr Leu Pro
            20                  25                  30

Leu Asp Lys Gly Ile Lys Pro Tyr Tyr Pro Glu His Val Val Asn His
        35                  40                  45

Tyr Phe Gln Thr Arg
    50

<210> SEQ ID NO 6
<211> LENGTH: 54
<212> TYPE: PRT
<213> ORGANISM: Artificial Sequence
<220> FEATURE:
<223> OTHER INFORMATION: HBV CONSENSUS SEQUENCE

<400> SEQUENCE: 6

Tyr Pro Glu His Val Val Asn His Tyr Phe Gln Thr Arg His Tyr Leu
1               5                   10                  15

His Thr Leu Trp Lys Ala Gly Ile Leu Tyr Lys Arg Glu Thr Thr Arg

```
                    20                  25                  30

Ser Ala Ser Phe Cys Gly Ser Pro Tyr Ser Trp Glu Gln Glu Leu Gln
            35                  40                  45

Ser Cys Trp Trp Leu Gln
    50

<210> SEQ ID NO 7
<211> LENGTH: 67
<212> TYPE: PRT
<213> ORGANISM: Artificial Sequence
<220> FEATURE:
<223> OTHER INFORMATION: HBV CONSENSUS SEQUENCE

<400> SEQUENCE: 7

Arg Val Ser Trp Pro Lys Phe Ala Val Pro Asn Leu Gln Ser Leu Thr
1               5                   10                  15

Asn Leu Leu Ser Ser Asn Leu Ser Trp Leu Ser Leu Asp Val Ser Ala
            20                  25                  30

Ala Phe Tyr His Ile Pro Leu His Pro Ala Ala Met Pro His Leu Leu
        35                  40                  45

Val Gly Ser Ser Gly Leu Ser Arg Tyr Val Ala Arg Leu Ser Ser Asn
    50                  55                  60

Ser Arg Ile
65

<210> SEQ ID NO 8
<211> LENGTH: 53
<212> TYPE: PRT
<213> ORGANISM: Artificial Sequence
<220> FEATURE:
<223> OTHER INFORMATION: HBV CONSENSUS SEQUENCE

<400> SEQUENCE: 8

Gly Thr Met Gln Asn Leu His Asp Ser Cys Ser Arg Asn Leu Tyr Val
1               5                   10                  15

Ser Leu Met Leu Leu Tyr Lys Thr Tyr Gly Arg Lys Leu His Leu Tyr
            20                  25                  30

Ser His Pro Ile Ile Leu Gly Phe Arg Lys Ile Pro Met Gly Val Gly
        35                  40                  45

Leu Ser Pro Phe Leu
    50

<210> SEQ ID NO 9
<211> LENGTH: 95
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (62)..(62)
<223> OTHER INFORMATION: C OR S

<400> SEQUENCE: 9

Gly Thr Met Gln Asn Leu His Asp Ser Cys Ser Arg Asn Leu Tyr Val
1               5                   10                  15

Ser Leu Met Leu Leu Tyr Lys Thr Tyr Gly Arg Lys Leu His Leu Tyr
            20                  25                  30

Ser His Pro Ile Ile Leu Gly Phe Arg Lys Ile Pro Met Gly Val Gly
        35                  40                  45

Leu Ser Pro Phe Leu Leu Ala Gln Phe Thr Ser Ala Ile Xaa Ser Val
```

```
                    50                  55                  60
Val Arg Arg Ala Phe Pro His Cys Leu Ala Phe Ser Tyr Met Asp Asp
 65                  70                  75                  80

Val Val Leu Gly Ala Lys Ser Val Gln His Leu Glu Ser Leu Tyr
                     85                  90                  95

<210> SEQ ID NO 10
<211> LENGTH: 110
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (41)..(41)
<223> OTHER INFORMATION: S OR T
<220> FEATURE:
<221> NAME/KEY: MISC_FEATURE
<222> LOCATION: (90)..(90)
<223> OTHER INFORMATION: C OR S

<400> SEQUENCE: 10

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
                20                  25                  30

Asp Pro Tyr Lys Glu Phe Gly Ala Xaa Val Glu Leu Leu Ser Phe Leu
             35                  40                  45

Pro Ser Asp Phe Phe Pro Ser Val Arg Asp Leu Leu Asp Thr Ala Ser
         50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Xaa Trp Gly Glu Leu Met Thr
                85                  90                  95

Leu Ala Thr Trp Val Gly Ser Asn Leu Glu Asp Pro Ala Ser
                100                 105                 110

<210> SEQ ID NO 11
<211> LENGTH: 123
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (44)..(44)
<223> OTHER INFORMATION: C OR S

<400> SEQUENCE: 11

Phe Leu Pro Ser Asp Phe Phe Pro Ser Val Arg Asp Leu Leu Asp Thr
 1               5                  10                  15

Ala Ser Ala Leu Tyr Arg Glu Ala Leu Glu Ser Pro Glu His Cys Ser
                20                  25                  30

Pro His His Thr Ala Leu Arg Gln Ala Ile Leu Xaa Trp Gly Glu Leu
             35                  40                  45

Met Thr Leu Ala Thr Trp Val Gly Ser Asn Leu Glu Asp Pro Ala Ser
         50                  55                  60

Arg Asp Leu Val Val Ser Tyr Val Asn Thr Asn Met Gly Leu Lys Ile
 65                  70                  75                  80

Arg Gln Leu Leu Trp Phe His Ile Ser Cys Leu Thr Phe Gly Arg Glu
                85                  90                  95
```

Thr Val Leu Glu Tyr Leu Val Ser Phe Gly Val Trp Ile Arg Thr Pro
            100                 105                 110

Pro Ala Tyr Arg Pro Pro Asn Ala Pro Ile Leu
        115                 120

<210> SEQ ID NO 12
<211> LENGTH: 102
<212> TYPE: PRT
<213> ORGANISM: Artificial Sequence
<220> FEATURE:
<223> OTHER INFORMATION: HBV CONSENSUS SEQUENCE

<400> SEQUENCE: 12

Ala Ser Arg Asp Leu Val Val Ser Tyr Val Asn Thr Asn Met Gly Leu
1               5                   10                  15

Lys Ile Arg Gln Leu Leu Trp Phe His Ile Ser Cys Leu Thr Phe Gly
            20                  25                  30

Arg Glu Thr Val Leu Glu Tyr Leu Val Ser Phe Gly Val Trp Ile Arg
        35                  40                  45

Thr Pro Pro Ala Tyr Arg Pro Pro Asn Ala Pro Ile Leu Ser Thr Leu
    50                  55                  60

Pro Glu Thr Thr Val Val Arg Arg Arg Gly Arg Ser Pro Arg Arg Arg
65                  70                  75                  80

Thr Pro Ser Pro Arg Arg Arg Arg Ser Gln Ser Pro Arg Arg Arg Arg
                85                  90                  95

Ser Gln Ser Arg Glu Ser
            100

<210> SEQ ID NO 13
<211> LENGTH: 54
<212> TYPE: PRT
<213> ORGANISM: Artificial Sequence
<220> FEATURE:
<223> OTHER INFORMATION: HBV CONSENSUS SEQUENCE

<400> SEQUENCE: 13

Thr Pro Pro Ala Tyr Arg Pro Pro Asn Ala Pro Ile Leu Ser Thr Leu
1               5                   10                  15

Pro Glu Thr Thr Val Val Arg Arg Arg Gly Arg Ser Pro Arg Arg Arg
            20                  25                  30

Thr Pro Ser Pro Arg Arg Arg Arg Ser Gln Ser Pro Arg Arg Arg Arg
        35                  40                  45

Ser Gln Ser Arg Glu Ser
    50

<210> SEQ ID NO 14
<211> LENGTH: 40
<212> TYPE: PRT
<213> ORGANISM: Artificial Sequence
<220> FEATURE:
<223> OTHER INFORMATION: HBV CONSENSUS SEQUENCE

<400> SEQUENCE: 14

Gln Gln Phe Val Gly Pro Leu Thr Val Asn Glu Lys Arg Arg Leu Lys
1               5                   10                  15

Leu Ile Met Pro Ala Arg Phe Tyr Pro Asn Val Thr Lys Tyr Leu Pro
            20                  25                  30

Leu Asp Lys Gly Ile Lys Pro Tyr
        35                  40

```
<210> SEQ ID NO 15
<211> LENGTH: 39
<212> TYPE: PRT
<213> ORGANISM: Artificial Sequence
<220> FEATURE:
<223> OTHER INFORMATION: HBV CONSENSUS SEQUENCE

<400> SEQUENCE: 15

Tyr Pro Glu His Val Val Asn His Tyr Phe Gln Thr Arg His Tyr Leu
1               5                   10                  15

His Thr Leu Trp Lys Ala Gly Ile Leu Tyr Lys Arg Glu Thr Thr Arg
            20                  25                  30

Ser Ala Ser Phe Cys Gly Ser
        35

<210> SEQ ID NO 16
<211> LENGTH: 42
<212> TYPE: PRT
<213> ORGANISM: Artificial Sequence
<220> FEATURE:
<223> OTHER INFORMATION: HBV CONSENSUS SEQUENCE

<400> SEQUENCE: 16

Arg Val Ser Trp Pro Lys Phe Ala Val Pro Asn Leu Gln Ser Leu Thr
1               5                   10                  15

Asn Leu Leu Ser Ser Asn Leu Ser Trp Leu Ser Leu Asp Val Ser Ala
            20                  25                  30

Ala Phe Tyr His Ile Pro Leu His Pro Ala
        35                  40

<210> SEQ ID NO 17
<211> LENGTH: 47
<212> TYPE: PRT
<213> ORGANISM: Artificial Sequence
<220> FEATURE:
<223> OTHER INFORMATION: HBV CONSENSUS SEQUENCE

<400> SEQUENCE: 17

Gly Thr Met Gln Asn Leu His Asp Ser Cys Ser Arg Asn Leu Tyr Val
1               5                   10                  15

Ser Leu Met Leu Leu Tyr Lys Thr Tyr Gly Arg Lys Leu His Leu Tyr
            20                  25                  30

Ser His Pro Ile Ile Leu Gly Phe Arg Lys Ile Pro Met Gly Val
        35                  40                  45

<210> SEQ ID NO 18
<211> LENGTH: 40
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (35)..(35)
<223> OTHER INFORMATION: C OR S

<400> SEQUENCE: 18

Lys Leu His Leu Tyr Ser His Pro Ile Ile Leu Gly Phe Arg Lys Ile
1               5                   10                  15

Pro Met Gly Val Gly Leu Ser Pro Phe Leu Leu Ala Gln Phe Thr Ser
            20                  25                  30

Ala Ile Xaa Ser Val Val Arg Arg
        35                  40
```

```
<210> SEQ ID NO 19
<211> LENGTH: 38
<212> TYPE: PRT
<213> ORGANISM: Artificial Sequence
<220> FEATURE:
<223> OTHER INFORMATION: HBV CONSENSUS SEQUENCE

<400> SEQUENCE: 19

Ala Ala Asn Trp Ile Leu Arg Gly Thr Ser Phe Val Tyr Val Pro Ser
1               5                   10                  15

Ala Leu Asn Pro Ala Asp Asp Pro Ser Arg Gly Arg Leu Gly Leu Tyr
                20                  25                  30

Arg Pro Leu Leu Arg Leu
            35

<210> SEQ ID NO 20
<211> LENGTH: 38
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (6)..(6)
<223> OTHER INFORMATION: S OR T

<400> SEQUENCE: 20

Lys Glu Phe Gly Ala Xaa Val Glu Leu Leu Ser Phe Leu Pro Ser Asp
1               5                   10                  15

Phe Phe Pro Ser Val Arg Asp Leu Leu Asp Thr Ala Ser Ala Leu Tyr
                20                  25                  30

Arg Glu Ala Leu Glu Ser
            35

<210> SEQ ID NO 21
<211> LENGTH: 60
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (15)..(15)
<223> OTHER INFORMATION: C OR S

<400> SEQUENCE: 21

His Cys Ser Pro His His Thr Ala Leu Arg Gln Ala Ile Leu Xaa Trp
1               5                   10                  15

Gly Glu Leu Met Thr Leu Ala Thr Trp Val Gly Ser Asn Leu Glu Asp
                20                  25                  30

Pro Ala Ser Arg Asp Leu Val Val Ser Tyr Val Asn Thr Asn Met Gly
            35                  40                  45

Leu Lys Ile Arg Gln Leu Leu Trp Phe His Ile Ser
        50                  55                  60

<210> SEQ ID NO 22
<211> LENGTH: 41
<212> TYPE: PRT
<213> ORGANISM: Artificial Sequence
<220> FEATURE:
<223> OTHER INFORMATION: HBV CONSENSUS SEQUENCE

<400> SEQUENCE: 22

Cys Leu Thr Phe Gly Arg Glu Thr Val Leu Glu Tyr Leu Val Ser Phe
```

```
                1               5                  10                 15
Gly Val Trp Ile Arg Thr Pro Pro Ala Tyr Arg Pro Pro Asn Ala Pro
                20                 25                 30

Ile Leu Ser Thr Leu Pro Glu Thr Thr
            35                  40

<210> SEQ ID NO 23
<211> LENGTH: 33
<212> TYPE: PRT
<213> ORGANISM: Artificial Sequence
<220> FEATURE:
<223> OTHER INFORMATION: HBV CONSENSUS SEQUENCE

<400> SEQUENCE: 23

Thr Pro Pro Ala Tyr Arg Pro Pro Asn Ala Pro Ile Leu Ser Thr Leu
1               5                   10                  15

Pro Glu Thr Thr Val Val Arg Arg Arg Gly Arg Ser Pro Arg Arg Arg
                20                  25                  30

Thr

<210> SEQ ID NO 24
<211> LENGTH: 35
<212> TYPE: PRT
<213> ORGANISM: Artificial Sequence
<220> FEATURE:
<223> OTHER INFORMATION: HBV CONSENSUS SEQUENCE

<400> SEQUENCE: 24

Val Gly Pro Leu Thr Val Asn Glu Lys Arg Arg Leu Lys Leu Ile Met
1               5                   10                  15

Pro Ala Arg Phe Tyr Pro Asn Val Thr Lys Tyr Leu Pro Leu Asp Lys
                20                  25                  30

Gly Ile Lys
            35

<210> SEQ ID NO 25
<211> LENGTH: 35
<212> TYPE: PRT
<213> ORGANISM: Artificial Sequence
<220> FEATURE:
<223> OTHER INFORMATION: HBV CONSENSUS SEQUENCE

<400> SEQUENCE: 25

Pro Glu His Val Val Asn His Tyr Phe Gln Thr Arg His Tyr Leu His
1               5                   10                  15

Thr Leu Trp Lys Ala Gly Ile Leu Tyr Lys Arg Glu Thr Thr Arg Ser
                20                  25                  30

Ala Ser Phe
            35

<210> SEQ ID NO 26
<211> LENGTH: 36
<212> TYPE: PRT
<213> ORGANISM: Artificial Sequence
<220> FEATURE:
<223> OTHER INFORMATION: HBV CONSENSUS SEQUENCE

<400> SEQUENCE: 26

Arg Val Ser Trp Pro Lys Phe Ala Val Pro Asn Leu Gln Ser Leu Thr
1               5                   10                  15

Asn Leu Leu Ser Ser Asn Leu Ser Trp Leu Ser Leu Asp Val Ser Ala
                20                  25                  30
```

Ala Phe Tyr His
        35

<210> SEQ ID NO 27
<211> LENGTH: 37
<212> TYPE: PRT
<213> ORGANISM: Artificial Sequence
<220> FEATURE:
<223> OTHER INFORMATION: HBV CONSENSUS SEQUENCE

<400> SEQUENCE: 27

Ser Arg Asn Leu Tyr Val Ser Leu Met Leu Leu Tyr Lys Thr Tyr Gly
1               5                   10                  15

Arg Lys Leu His Leu Tyr Ser His Pro Ile Ile Leu Gly Phe Arg Lys
            20                  25                  30

Ile Pro Met Gly Val
        35

<210> SEQ ID NO 28
<211> LENGTH: 40
<212> TYPE: PRT
<213> ORGANISM: Artificial Sequence
<220> FEATURE:
<223> OTHER INFORMATION: HBV CONSENSUS SEQUENCE

<400> SEQUENCE: 28

Lys Leu His Leu Tyr Ser His Pro Ile Ile Leu Gly Phe Arg Lys Ile
1               5                   10                  15

Pro Met Gly Val Gly Leu Ser Pro Phe Leu Leu Ala Gln Phe Thr Ser
            20                  25                  30

Ala Ile Ser Ser Val Val Arg Arg
        35                  40

<210> SEQ ID NO 29
<211> LENGTH: 36
<212> TYPE: PRT
<213> ORGANISM: Artificial Sequence
<220> FEATURE:
<223> OTHER INFORMATION: HBV CONSENSUS SEQUENCE

<400> SEQUENCE: 29

Ala Asn Trp Ile Leu Arg Gly Thr Ser Phe Val Tyr Val Pro Ser Ala
1               5                   10                  15

Leu Asn Pro Ala Asp Asp Pro Ser Arg Gly Arg Leu Gly Leu Tyr Arg
            20                  25                  30

Pro Leu Leu Arg
        35

<210> SEQ ID NO 30
<211> LENGTH: 33
<212> TYPE: PRT
<213> ORGANISM: Artificial Sequence
<220> FEATURE:
<223> OTHER INFORMATION: HBV CONSENSUS SEQUENCE

<400> SEQUENCE: 30

Lys Glu Phe Gly Ala Thr Val Glu Leu Leu Ser Phe Leu Pro Ser Asp
1               5                   10                  15

Phe Phe Pro Ser Val Arg Asp Leu Leu Asp Thr Ala Ser Ala Leu Tyr
            20                  25                  30

Arg

```
<210> SEQ ID NO 31
<211> LENGTH: 35
<212> TYPE: PRT
<213> ORGANISM: Artificial Sequence
<220> FEATURE:
<223> OTHER INFORMATION: HBV CONSENSUS SEQUENCE

<400> SEQUENCE: 31

Ser Pro His His Thr Ala Leu Arg Gln Ala Ile Leu Ser Trp Gly Glu
1               5                   10                  15

Leu Met Thr Leu Ala Thr Trp Val Gly Ser Asn Leu Glu Asp Pro Ala
                20                  25                  30

Ser Arg Asp
        35

<210> SEQ ID NO 32
<211> LENGTH: 35
<212> TYPE: PRT
<213> ORGANISM: Artificial Sequence
<220> FEATURE:
<223> OTHER INFORMATION: HBV CONSENSUS SEQUENCE

<400> SEQUENCE: 32

Leu Thr Phe Gly Arg Glu Thr Val Leu Glu Tyr Leu Val Ser Phe Gly
1               5                   10                  15

Val Trp Ile Arg Thr Pro Pro Ala Tyr Arg Pro Pro Asn Ala Pro Ile
                20                  25                  30

Leu Ser Thr
        35

<210> SEQ ID NO 33
<211> LENGTH: 31
<212> TYPE: PRT
<213> ORGANISM: Artificial Sequence
<220> FEATURE:
<223> OTHER INFORMATION: HBV CONSENSUS SEQUENCE

<400> SEQUENCE: 33

Pro Pro Ala Tyr Arg Pro Pro Asn Ala Pro Ile Leu Ser Thr Leu Pro
1               5                   10                  15

Glu Thr Thr Val Val Arg Arg Arg Gly Arg Ser Pro Arg Arg Arg
                20                  25                  30

<210> SEQ ID NO 34
<211> LENGTH: 39
<212> TYPE: PRT
<213> ORGANISM: Artificial Sequence
<220> FEATURE:
<223> OTHER INFORMATION: HBV CONSENSUS SEQUENCE

<400> SEQUENCE: 34

Arg Val Ser Trp Pro Lys Phe Ala Val Pro Asn Leu Gln Ser Leu Thr
1               5                   10                  15

Asn Leu Leu Ser Ser Asn Leu Ser Trp Leu Ser Leu Asp Val Ser Ala
                20                  25                  30

Ala Phe Tyr His Lys Lys Lys
        35

<210> SEQ ID NO 35
<211> LENGTH: 39
<212> TYPE: PRT
<213> ORGANISM: Artificial Sequence
<220> FEATURE:
```

<223> OTHER INFORMATION: HBV CONSENSUS SEQUENCE

<400> SEQUENCE: 35

Lys Lys Lys Ala Asn Trp Ile Leu Arg Gly Thr Ser Phe Val Tyr Val
1               5                   10                  15

Pro Ser Ala Leu Asn Pro Ala Asp Asp Pro Ser Arg Gly Arg Leu Gly
            20                  25                  30

Leu Tyr Arg Pro Leu Leu Arg
        35

<210> SEQ ID NO 36
<211> LENGTH: 38
<212> TYPE: PRT
<213> ORGANISM: Artificial Sequence
<220> FEATURE:
<223> OTHER INFORMATION: HBV CONSENSUS SEQUENCE

<400> SEQUENCE: 36

Lys Lys Lys Glu Phe Gly Ala Thr Val Glu Leu Leu Ser Phe Leu Pro
1               5                   10                  15

Ser Asp Phe Phe Pro Ser Val Arg Asp Leu Leu Asp Thr Ala Ser Ala
            20                  25                  30

Leu Tyr Arg Lys Lys Lys
        35

<210> SEQ ID NO 37
<211> LENGTH: 38
<212> TYPE: PRT
<213> ORGANISM: Artificial Sequence
<220> FEATURE:
<223> OTHER INFORMATION: HBV CONSENSUS SEQUENCE

<400> SEQUENCE: 37

Ser Pro His His Thr Ala Leu Arg Gln Ala Ile Leu Ser Trp Gly Glu
1               5                   10                  15

Leu Met Thr Leu Ala Thr Trp Val Gly Ser Asn Leu Glu Asp Pro Ala
            20                  25                  30

Ser Arg Asp Lys Lys Lys
        35

<210> SEQ ID NO 38
<211> LENGTH: 38
<212> TYPE: PRT
<213> ORGANISM: Artificial Sequence
<220> FEATURE:
<223> OTHER INFORMATION: HBV CONSENSUS SEQUENCE

<400> SEQUENCE: 38

Leu Thr Phe Gly Arg Glu Thr Val Leu Glu Tyr Leu Val Ser Phe Gly
1               5                   10                  15

Val Trp Ile Arg Thr Pro Pro Ala Tyr Arg Pro Pro Asn Ala Pro Ile
            20                  25                  30

Leu Ser Thr Lys Lys Lys
        35

<210> SEQ ID NO 39
<211> LENGTH: 1468
<212> TYPE: PRT
<213> ORGANISM: Artificial Sequence
<220> FEATURE:
<223> OTHER INFORMATION: HBV CONSENSUS SEQUENCE

<400> SEQUENCE: 39

```
Met Pro Leu Ser Tyr Gln His Phe Arg Lys Leu Leu Leu Asp Asp
1               5                  10                 15

Glu Ala Gly Pro Leu Glu Glu Leu Pro Arg Leu Ala Asp Glu Gly
            20                  25                 30

Leu Asn Arg Arg Val Ala Glu Asp Leu Asn Leu Gly Asn Leu Asn Val
        35                  40                 45

Ser Ile Pro Trp Thr His Lys Val Gly Asn Phe Thr Gly Leu Tyr Ser
50                  55                  60

Ser Thr Val Pro Val Phe Asn Pro Glu Trp Gln Thr Pro Ser Phe Pro
65                  70                  75                 80

His Ile His Leu Gln Glu Asp Ile Ile Asn Arg Cys Gln Gln Phe Val
                85                  90                 95

Gly Pro Leu Thr Val Asn Glu Lys Arg Arg Leu Lys Leu Ile Met Pro
            100                 105                110

Ala Arg Phe Tyr Pro Asn Val Thr Lys Tyr Leu Pro Leu Asp Lys Gly
        115                 120                125

Ile Lys Pro Tyr Tyr Pro Glu His Val Val Asn His Tyr Phe Gln Thr
    130                 135                 140

Arg His Tyr Leu His Thr Leu Trp Lys Ala Gly Ile Leu Tyr Lys Arg
145                 150                 155                160

Glu Thr Thr Arg Ser Ala Ser Phe Cys Gly Ser Pro Tyr Ser Trp Glu
                165                 170                 175

Gln Glu Leu Gln Ser Cys Trp Trp Leu Gln Phe Arg Asn Ser Lys Pro
            180                 185                 190

Cys Ser Glu Tyr Cys Leu Ser His Ile Val Asn Leu Leu Glu Asp Trp
        195                 200                 205

Gly Pro Cys Thr Glu His Gly Glu His His Ile Arg Ile Pro Arg Thr
    210                 215                 220

Pro Ala Arg Val Thr Gly Gly Val Phe Leu Val Asp Lys Asn Pro His
225                 230                 235                240

Asn Thr Thr Glu Ser Arg Leu Val Val Asp Phe Ser Gln Phe Ser Arg
                245                 250                 255

Gly Asn Thr Arg Val Ser Trp Pro Lys Phe Ala Val Pro Asn Leu Gln
            260                 265                 270

Ser Leu Thr Asn Leu Leu Ser Ser Asn Leu Ser Trp Leu Ser Leu Asp
        275                 280                 285

Val Ser Ala Ala Phe Tyr His Ile Pro Leu His Pro Ala Ala Met Pro
    290                 295                 300

His Leu Leu Val Gly Ser Ser Gly Leu Ser Arg Tyr Val Ala Arg Leu
305                 310                 315                320

Ser Ser Asn Ser Arg Ile Ile Asn Asn Gln His Gly Thr Met Gln Asn
                325                 330                 335

Leu His Asp Ser Cys Ser Arg Asn Leu Tyr Val Ser Leu Met Leu Leu
            340                 345                 350

Tyr Lys Thr Tyr Gly Arg Lys Leu His Leu Tyr Ser His Pro Ile Ile
        355                 360                 365

Leu Gly Phe Arg Lys Ile Pro Met Gly Val Gly Leu Ser Pro Phe Leu
    370                 375                 380

Leu Ala Gln Phe Thr Ser Ala Ile Cys Ser Val Val Arg Arg Ala Phe
385                 390                 395                400

Pro His Cys Leu Ala Phe Ser Tyr Met Asp Asp Val Val Leu Gly Ala
                405                 410                 415
```

Lys Ser Val Gln His Leu Glu Ser Leu Tyr Thr Ala Val Thr Asn Phe
            420                 425                 430

Leu Leu Ser Leu Gly Ile His Leu Asn Pro Asn Lys Thr Lys Arg Trp
            435                 440                 445

Gly Tyr Ser Leu Asn Phe Met Gly Tyr Val Ile Gly Ser Trp Gly Thr
            450                 455                 460

Leu Pro Gln Glu His Ile Val Gln Lys Ile Lys Gln Cys Phe Arg Lys
465                 470                 475                 480

Leu Pro Val Asn Arg Pro Ile Asp Trp Lys Val Cys Gln Arg Ile Val
            485                 490                 495

Gly Leu Leu Gly Phe Ala Ala Pro Phe Thr Gln Cys Gly Tyr Pro Ala
            500                 505                 510

Leu Met Pro Leu Tyr Ala Cys Ile Gln Ala Lys Gln Ala Phe Thr Phe
            515                 520                 525

Ser Pro Thr Tyr Lys Ala Phe Leu Cys Lys Gln Tyr Leu Asn Leu Tyr
            530                 535                 540

Pro Val Ala Arg Gln Arg Pro Gly Leu Cys Gln Val Phe Ala Asp Ala
545                 550                 555                 560

Thr Pro Thr Gly Trp Gly Leu Ala Ile Gly His Gln Arg Met Arg Gly
            565                 570                 575

Thr Phe Val Ala Pro Leu Pro Ile His Thr Ala Glu Leu Leu Ala Ala
            580                 585                 590

Cys Phe Ala Arg Ser Arg Ser Gly Ala Lys Leu Ile Gly Thr Asp Asn
            595                 600                 605

Ser Val Val Leu Ser Arg Lys Tyr Thr Ser Phe Pro Trp Leu Leu Gly
            610                 615                 620

Cys Ala Ala Asn Trp Ile Leu Arg Gly Thr Ser Phe Val Tyr Val Pro
625                 630                 635                 640

Ser Ala Leu Asn Pro Ala Asp Asp Pro Ser Arg Gly Arg Leu Gly Leu
            645                 650                 655

Tyr Arg Pro Leu Leu Arg Leu Pro Phe Arg Pro Thr Thr Gly Arg Thr
            660                 665                 670

Ser Leu Tyr Ala Val Ser Pro Ser Val Pro Ser His Leu Pro Asp Arg
            675                 680                 685

Val His Phe Ala Ser Pro Leu His Val Ala Trp Arg Pro Pro Met Gln
            690                 695                 700

Leu Phe His Leu Cys Leu Ile Ile Ser Cys Ser Cys Pro Thr Val Gln
705                 710                 715                 720

Ala Ser Lys Leu Cys Leu Gly Trp Leu Trp Gly Met Asp Ile Asp Pro
            725                 730                 735

Tyr Lys Glu Phe Gly Ala Ser Val Glu Leu Leu Ser Phe Leu Pro Ser
            740                 745                 750

Asp Phe Phe Pro Ser Val Arg Asp Leu Leu Asp Thr Ala Ser Ala Leu
            755                 760                 765

Tyr Arg Glu Ala Leu Glu Ser Pro Glu His Cys Ser Pro His His Thr
            770                 775                 780

Ala Leu Arg Gln Ala Ile Leu Cys Trp Gly Glu Leu Met Thr Leu Ala
785                 790                 795                 800

Thr Trp Val Gly Ser Asn Leu Glu Asp Pro Ala Ser Arg Asp Leu Val
            805                 810                 815

Val Ser Tyr Val Asn Thr Asn Met Gly Leu Lys Ile Arg Gln Leu Leu
            820                 825                 830

Trp Phe His Ile Ser Cys Leu Thr Phe Gly Arg Glu Thr Val Leu Glu

-continued

```
                835                 840                 845
Tyr Leu Val Ser Phe Gly Val Trp Ile Arg Thr Pro Pro Ala Tyr Arg
    850                 855                 860
Pro Pro Asn Ala Pro Ile Leu Ser Thr Leu Pro Glu Thr Thr Val Val
865                 870                 875                 880
Arg Arg Arg Gly Arg Ser Pro Arg Arg Thr Pro Ser Pro Arg Arg
                885                 890                 895
Arg Arg Ser Gln Ser Pro Arg Arg Arg Ser Gln Ser Arg Glu Ser
    900                 905                 910
Gln Cys Met Ala Ala Arg Leu Cys Cys Gln Leu Asp Pro Ala Arg Asp
    915                 920                 925
Val Leu Cys Leu Arg Pro Val Gly Ala Glu Ser Arg Gly Arg Pro Leu
    930                 935                 940
Ser Gly Pro Leu Gly Thr Leu Pro Ser Pro Ser Pro Ala Val Pro
945                 950                 955                 960
Ala Asp His Gly Ala His Leu Ser Leu Arg Gly Leu Pro Val Cys Ala
                965                 970                 975
Phe Ser Ser Ala Gly Pro Cys Ala Leu Arg Phe Thr Ser Ala Arg Arg
                980                 985                 990
Met Glu Thr Thr Val Asn Ala His  Gln Ile Leu Pro Lys  Val Leu His
            995                 1000                1005
Lys Arg Thr Leu Gly Leu Ser  Ala Met Ser Thr Thr  Asp Leu Glu
    1010                1015                1020
Ala Tyr Phe Lys Asp Cys Val  Phe Lys Asp Trp Glu  Glu Leu Gly
    1025                1030                1035
Glu Glu Ile Arg Leu Lys Val  Phe Val Leu Gly Gly  Cys Arg His
    1040                1045                1050
Lys Leu Val Cys Ser Pro Ala  Pro Cys Asn Phe Phe  Thr Ser Ala
    1055                1060                1065
Met Gly Gly Trp Ser Ser Lys  Pro Arg Lys Gly Met  Gly Thr Asn
    1070                1075                1080
Leu Ser Val Pro Asn Pro Leu  Gly Phe Phe Pro Asp  His Gln Leu
    1085                1090                1095
Asp Pro Ala Phe Arg Ala Asn  Ser Asn Asn Pro Asp  Trp Asp Phe
    1100                1105                1110
Asn Pro Asn Lys Asp Gln Trp  Pro Ala Ala Asn Gln  Val Gly Val
    1115                1120                1125
Gly Ala Phe Gly Pro Gly Phe  Thr Pro Pro His Gly  Gly Leu Leu
    1130                1135                1140
Gly Trp Ser Pro Gln Ala Gln  Gly Ile Leu Thr Thr  Val Pro Ala
    1145                1150                1155
Asp Pro Pro Pro Ala Ser Thr  Asn Arg Gln Ser Gly  Arg Gln Pro
    1160                1165                1170
Thr Pro Ile Ser Pro Pro Leu  Arg Asp Ser His Pro  Gln Ala Met
    1175                1180                1185
Gln Trp Asn Ser Thr Thr Phe  His Gln Ala Leu Gln  Asp Pro Arg
    1190                1195                1200
Val Arg Gly Leu Tyr Phe Pro  Ala Gly Gly Ser Ser  Ser Gly Thr
    1205                1210                1215
Val Asn Pro Ala Pro Thr Thr  Ala Ser Leu Ile Ser  Ser Ile Phe
    1220                1225                1230
Ser Arg Thr Gly Asp Pro Ala  Pro Asn Met Glu Asn  Ile Thr Ser
    1235                1240                1245
```

Gly Phe Leu Gly Pro Leu Leu Val Leu Gln Ala Gly Phe Phe Leu
             1250                1255                1260

Leu Thr Lys Ile Leu Thr Ile Pro Gln Ser Leu Asp Ser Trp Trp
         1265                1270                1275

Thr Ser Leu Asn Phe Leu Gly Gly Thr Pro Val Cys Leu Gly Gln
    1280                1285                1290

Asn Ser Gln Ser Pro Thr Ser Asn His Ser Pro Thr Ser Cys Pro
1295                1300                1305

Pro Ile Cys Pro Gly Tyr Arg Trp Met Cys Leu Arg Arg Phe Ile
    1310                1315                1320

Ile Phe Leu Phe Ile Leu Leu Cys Leu Ile Phe Leu Leu Val
    1325                1330                1335

Leu Leu Asp Tyr Gln Gly Met Leu Pro Val Cys Pro Leu Ile Pro
    1340                1345                1350

Gly Ser Ser Thr Thr Ser Thr Gly Pro Cys Lys Thr Cys Thr Thr
    1355                1360                1365

Pro Ala Gln Gly Thr Ser Met Phe Pro Ser Cys Cys Cys Thr Lys
    1370                1375                1380

Pro Ser Asp Gly Asn Cys Thr Cys Ile Pro Ile Pro Ser Ser Trp
    1385                1390                1395

Ala Phe Gly Lys Tyr Leu Trp Glu Trp Ala Ser Ala Arg Phe Ser
    1400                1405                1410

Trp Leu Ser Leu Leu Val Pro Phe Val Gln Trp Phe Val Gly Leu
    1415                1420                1425

Ser Pro Thr Val Trp Leu Ser Val Ile Trp Met Met Trp Tyr Trp
    1430                1435                1440

Gly Pro Ser Leu Tyr Asn Ile Leu Ser Pro Phe Ile Pro Leu Leu
    1445                1450                1455

Pro Ile Phe Phe Cys Leu Trp Val Tyr Ile
    1460                1465

<210> SEQ ID NO 40
<211> LENGTH: 55
<212> TYPE: PRT
<213> ORGANISM: Artificial Sequence
<220> FEATURE:
<223> OTHER INFORMATION: HBV CONSENSUS SEQUENCE

<400> SEQUENCE: 40

Leu Pro Arg Leu Ala Asp Glu Gly Leu Asn Arg Arg Val Ala Glu Asp
1               5                   10                  15

Leu Asn Leu Gly Asn Leu Asn Val Ser Ile Pro Trp Thr His Lys Val
            20                  25                  30

Gly Asn Phe Thr Gly Leu Tyr Ser Ser Thr Val Pro Val Phe Asn Pro
        35                  40                  45

Glu Trp Gln Thr Pro Ser Phe
    50                  55

<210> SEQ ID NO 41
<211> LENGTH: 51
<212> TYPE: PRT
<213> ORGANISM: Artificial Sequence
<220> FEATURE:
<223> OTHER INFORMATION: HBV CONSENSUS SEQUENCE

<400> SEQUENCE: 41

Cys Thr Glu His Gly Glu His His Ile Arg Ile Pro Arg Thr Pro Ala

```
                1               5                  10                 15
Arg Val Thr Gly Gly Val Phe Leu Val Asp Lys Asn Pro His Asn Thr
                20                 25                 30

Thr Glu Ser Arg Leu Val Val Asp Phe Ser Gln Phe Ser Arg Gly Asn
            35                 40                 45

Thr Arg Val
        50

<210> SEQ ID NO 42
<211> LENGTH: 55
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (22)..(22)
<223> OTHER INFORMATION: C OR S

<400> SEQUENCE: 42

Arg Lys Ile Pro Met Gly Val Gly Leu Ser Pro Phe Leu Leu Ala Gln
1               5                  10                 15

Phe Thr Ser Ala Ile Xaa Ser Val Val Arg Arg Ala Phe Pro His Cys
            20                 25                 30

Leu Ala Phe Ser Tyr Met Asp Asp Val Val Leu Gly Ala Lys Ser Val
        35                 40                 45

Gln His Leu Glu Ser Leu Tyr
    50                 55

<210> SEQ ID NO 43
<211> LENGTH: 52
<212> TYPE: PRT
<213> ORGANISM: Artificial Sequence
<220> FEATURE:
<223> OTHER INFORMATION: HBV CONSENSUS SEQUENCE

<400> SEQUENCE: 43

Leu Gly Ala Lys Ser Val Gln His Leu Glu Ser Leu Tyr Thr Ala Val
1               5                  10                 15

Thr Asn Phe Leu Leu Ser Leu Gly Ile His Leu Asn Pro Asn Lys Thr
            20                 25                 30

Lys Arg Trp Gly Tyr Ser Leu Asn Phe Met Gly Tyr Val Ile Gly Ser
        35                 40                 45

Trp Gly Thr Leu
    50

<210> SEQ ID NO 44
<211> LENGTH: 59
<212> TYPE: PRT
<213> ORGANISM: Artificial Sequence
<220> FEATURE:
<223> OTHER INFORMATION: HBV CONSENSUS SEQUENCE

<400> SEQUENCE: 44

Lys Ile Lys Gln Cys Phe Arg Lys Leu Pro Val Asn Arg Pro Ile Asp
1               5                  10                 15

Trp Lys Val Cys Gln Arg Ile Val Gly Leu Leu Gly Phe Ala Ala Pro
            20                 25                 30

Phe Thr Gln Cys Gly Tyr Pro Ala Leu Met Pro Leu Tyr Ala Cys Ile
        35                 40                 45

Gln Ala Lys Gln Ala Phe Thr Phe Ser Pro Thr
```

<210> SEQ ID NO 45
<211> LENGTH: 50
<212> TYPE: PRT
<213> ORGANISM: Artificial Sequence
<220> FEATURE:
<223> OTHER INFORMATION: HBV CONSENSUS SEQUENCE

<400> SEQUENCE: 45

Ile Gln Ala Lys Gln Ala Phe Thr Phe Ser Pro Thr Tyr Lys Ala Phe
1               5                   10                  15

Leu Cys Lys Gln Tyr Leu Asn Leu Tyr Pro Val Ala Arg Gln Arg Pro
            20                  25                  30

Gly Leu Cys Gln Val Phe Ala Asp Ala Thr Pro Thr Gly Trp Gly Leu
        35                  40                  45

Ala Ile
    50

<210> SEQ ID NO 46
<211> LENGTH: 48
<212> TYPE: PRT
<213> ORGANISM: Artificial Sequence
<220> FEATURE:
<223> OTHER INFORMATION: HBV CONSENSUS SEQUENCE

<400> SEQUENCE: 46

Phe Ala Asp Ala Thr Pro Thr Gly Trp Gly Leu Ala Ile Gly His Gln
1               5                   10                  15

Arg Met Arg Gly Thr Phe Val Ala Pro Leu Pro Ile His Thr Ala Glu
            20                  25                  30

Leu Leu Ala Ala Cys Phe Ala Arg Ser Arg Ser Gly Ala Lys Leu Ile
        35                  40                  45

<210> SEQ ID NO 47
<211> LENGTH: 59
<212> TYPE: PRT
<213> ORGANISM: Artificial Sequence
<220> FEATURE:
<223> OTHER INFORMATION: HBV CONSENSUS SEQUENCE

<400> SEQUENCE: 47

Ala Cys Phe Ala Arg Ser Arg Ser Gly Ala Lys Leu Ile Gly Thr Asp
1               5                   10                  15

Asn Ser Val Val Leu Ser Arg Lys Tyr Thr Ser Phe Pro Trp Leu Leu
            20                  25                  30

Gly Cys Ala Ala Asn Trp Ile Leu Arg Gly Thr Ser Phe Val Tyr Val
        35                  40                  45

Pro Ser Ala Leu Asn Pro Ala Asp Asp Pro Ser
    50                  55

<210> SEQ ID NO 48
<211> LENGTH: 63
<212> TYPE: PRT
<213> ORGANISM: Artificial Sequence
<220> FEATURE:
<223> OTHER INFORMATION: HBV CONSENSUS SEQUENCE

<400> SEQUENCE: 48

Tyr Val Pro Ser Ala Leu Asn Pro Ala Asp Asp Pro Ser Arg Gly Arg
1               5                   10                  15

Leu Gly Leu Tyr Arg Pro Leu Leu Arg Leu Pro Phe Arg Pro Thr Thr

```
                    20                  25                  30
Gly Arg Thr Ser Leu Tyr Ala Val Ser Pro Ser Val Pro Ser His Leu
                35                  40                  45

Pro Asp Arg Val His Phe Ala Ser Pro Leu His Val Ala Trp Arg
            50                  55                  60
```

<210> SEQ ID NO 49
<211> LENGTH: 60
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (41)..(41)
<223> OTHER INFORMATION: S OR T

<400> SEQUENCE: 49

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
                20                  25                  30

Asp Pro Tyr Lys Glu Phe Gly Ala Xaa Val Glu Leu Leu Ser Phe Leu
                35                  40                  45

Pro Ser Asp Phe Phe Pro Ser Val Arg Asp Leu Leu
            50                  55                  60
```

<210> SEQ ID NO 50
<211> LENGTH: 64
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (44)..(44)
<223> OTHER INFORMATION: C OR S

<400> SEQUENCE: 50

```
Phe Leu Pro Ser Asp Phe Phe Pro Ser Val Arg Asp Leu Leu Asp Thr
1               5                   10                  15

Ala Ser Ala Leu Tyr Arg Glu Ala Leu Glu Ser Pro Glu His Cys Ser
                20                  25                  30

Pro His His Thr Ala Leu Arg Gln Ala Ile Leu Xaa Trp Gly Glu Leu
                35                  40                  45

Met Thr Leu Ala Thr Trp Val Gly Ser Asn Leu Glu Asp Pro Ala Ser
            50                  55                  60
```

<210> SEQ ID NO 51
<211> LENGTH: 61
<212> TYPE: PRT
<213> ORGANISM: Artificial Sequence
<220> FEATURE:
<223> OTHER INFORMATION: HBV CONSENSUS SEQUENCE

<400> SEQUENCE: 51

```
Ala Ser Arg Asp Leu Val Val Ser Tyr Val Asn Thr Asn Met Gly Leu
1               5                   10                  15

Lys Ile Arg Gln Leu Leu Trp Phe His Ile Ser Cys Leu Thr Phe Gly
                20                  25                  30

Arg Glu Thr Val Leu Glu Tyr Leu Val Ser Phe Gly Val Trp Ile Arg
                35                  40                  45
```

Thr Pro Pro Ala Tyr Arg Pro Pro Asn Ala Pro Ile Leu
    50              55              60

<210> SEQ ID NO 52
<211> LENGTH: 52
<212> TYPE: PRT
<213> ORGANISM: Artificial Sequence
<220> FEATURE:
<223> OTHER INFORMATION: HBV CONSENSUS SEQUENCE

<400> SEQUENCE: 52

His Leu Ser Leu Arg Gly Leu Pro Val Cys Ala Phe Ser Ser Ala Gly
1               5                   10                  15

Pro Cys Ala Leu Arg Phe Thr Ser Ala Arg Arg Met Glu Thr Thr Val
            20                  25                  30

Asn Ala His Gln Ile Leu Pro Lys Val Leu His Lys Arg Thr Leu Gly
        35                  40                  45

Leu Ser Ala Met
    50

<210> SEQ ID NO 53
<211> LENGTH: 58
<212> TYPE: PRT
<213> ORGANISM: Artificial Sequence
<220> FEATURE:
<223> OTHER INFORMATION: HBV CONSENSUS SEQUENCE

<400> SEQUENCE: 53

Lys Val Leu His Lys Arg Thr Leu Gly Leu Ser Ala Met Ser Thr Thr
1               5                   10                  15

Asp Leu Glu Ala Tyr Phe Lys Asp Cys Val Phe Lys Asp Trp Glu Glu
            20                  25                  30

Leu Gly Glu Glu Ile Arg Leu Lys Val Phe Val Leu Gly Gly Cys Arg
        35                  40                  45

His Lys Leu Val Cys Ser Pro Ala Pro Cys
    50                  55

<210> SEQ ID NO 54
<211> LENGTH: 54
<212> TYPE: PRT
<213> ORGANISM: Artificial Sequence
<220> FEATURE:
<223> OTHER INFORMATION: HBV CONSENSUS SEQUENCE

<400> SEQUENCE: 54

Arg Gln Pro Thr Pro Ile Ser Pro Pro Leu Arg Asp Ser His Pro Gln
1               5                   10                  15

Ala Met Gln Trp Asn Ser Thr Thr Phe His Gln Ala Leu Gln Asp Pro
            20                  25                  30

Arg Val Arg Gly Leu Tyr Phe Pro Ala Gly Gly Ser Ser Ser Gly Thr
        35                  40                  45

Val Asn Pro Ala Pro Thr
    50

<210> SEQ ID NO 55
<211> LENGTH: 56
<212> TYPE: PRT
<213> ORGANISM: Artificial Sequence
<220> FEATURE:
<223> OTHER INFORMATION: HBV CONSENSUS SEQUENCE

<400> SEQUENCE: 55

```
Pro Asn Met Glu Asn Ile Thr Ser Gly Phe Leu Gly Pro Leu Leu Val
1               5                   10                  15

Leu Gln Ala Gly Phe Phe Leu Leu Thr Lys Ile Leu Thr Ile Pro Gln
            20                  25                  30

Ser Leu Asp Ser Trp Trp Thr Ser Leu Asn Phe Leu Gly Gly Thr Pro
        35                  40                  45

Val Cys Leu Gly Gln Asn Ser Gln
    50                  55

<210> SEQ ID NO 56
<211> LENGTH: 35
<212> TYPE: PRT
<213> ORGANISM: Artificial Sequence
<220> FEATURE:
<223> OTHER INFORMATION: HBV CONSENSUS SEQUENCE

<400> SEQUENCE: 56

Pro Gly Tyr Arg Trp Met Cys Leu Arg Arg Phe Ile Ile Phe Leu Phe
1               5                   10                  15

Ile Leu Leu Leu Cys Leu Ile Phe Leu Val Leu Leu Asp Tyr Gln
            20                  25                  30

Gly Met Leu
        35

<210> SEQ ID NO 57
<211> LENGTH: 56
<212> TYPE: PRT
<213> ORGANISM: Artificial Sequence
<220> FEATURE:
<223> OTHER INFORMATION: HBV CONSENSUS SEQUENCE

<400> SEQUENCE: 57

Ile Pro Ile Pro Ser Ser Trp Ala Phe Gly Lys Tyr Leu Trp Glu Trp
1               5                   10                  15

Ala Ser Ala Arg Phe Ser Trp Leu Ser Leu Leu Val Pro Phe Val Gln
            20                  25                  30

Trp Phe Val Gly Leu Ser Pro Thr Val Trp Leu Ser Val Ile Trp Met
        35                  40                  45

Met Trp Tyr Trp Gly Pro Ser Leu
    50                  55

<210> SEQ ID NO 58
<211> LENGTH: 49
<212> TYPE: PRT
<213> ORGANISM: Artificial Sequence
<220> FEATURE:
<223> OTHER INFORMATION: HBV CONSENSUS SEQUENCE

<400> SEQUENCE: 58

Glu Gly Leu Asn Arg Arg Val Ala Glu Asp Leu Asn Leu Gly Asn Leu
1               5                   10                  15

Asn Val Ser Ile Pro Trp Thr His Lys Val Gly Asn Phe Thr Gly Leu
            20                  25                  30

Tyr Ser Ser Thr Val Pro Val Phe Asn Pro Glu Trp Gln Thr Pro Ser
        35                  40                  45

Phe

<210> SEQ ID NO 59
<211> LENGTH: 39
<212> TYPE: PRT
<213> ORGANISM: Artificial Sequence
```

<220> FEATURE:
<223> OTHER INFORMATION: HBV CONSENSUS SEQUENCE

<400> SEQUENCE: 59

Arg Thr Pro Ala Arg Val Thr Gly Gly Val Phe Leu Val Asp Lys Asn
1               5                   10                  15

Pro His Asn Thr Thr Glu Ser Arg Leu Val Val Asp Phe Ser Gln Phe
            20                  25                  30

Ser Arg Gly Asn Thr Arg Val
        35

<210> SEQ ID NO 60
<211> LENGTH: 37
<212> TYPE: PRT
<213> ORGANISM: Artificial Sequence
<220> FEATURE:
<223> OTHER INFORMATION: HBV CONSENSUS SEQUENCE

<400> SEQUENCE: 60

Lys Phe Ala Val Pro Asn Leu Gln Ser Leu Thr Asn Leu Leu Ser Ser
1               5                   10                  15

Asn Leu Ser Trp Leu Ser Leu Asp Val Ser Ala Ala Phe Tyr His Ile
            20                  25                  30

Pro Leu His Pro Ala
        35

<210> SEQ ID NO 61
<211> LENGTH: 38
<212> TYPE: PRT
<213> ORGANISM: Artificial Sequence
<220> FEATURE:
<223> OTHER INFORMATION: HBV CONSENSUS SEQUENCE

<400> SEQUENCE: 61

Val Ser Ala Ala Phe Tyr His Ile Pro Leu His Pro Ala Ala Met Pro
1               5                   10                  15

His Leu Leu Val Gly Ser Ser Gly Leu Ser Arg Tyr Val Ala Arg Leu
            20                  25                  30

Ser Ser Asn Ser Arg Ile
        35

<210> SEQ ID NO 62
<211> LENGTH: 37
<212> TYPE: PRT
<213> ORGANISM: Artificial Sequence
<220> FEATURE:
<223> OTHER INFORMATION: HBV CONSENSUS SEQUENCE

<400> SEQUENCE: 62

Leu Ala Phe Ser Tyr Met Asp Asp Val Val Leu Gly Ala Lys Ser Val
1               5                   10                  15

Gln His Leu Glu Ser Leu Tyr Thr Ala Val Thr Asn Phe Leu Leu Ser
            20                  25                  30

Leu Gly Ile His Leu
        35

<210> SEQ ID NO 63
<211> LENGTH: 38
<212> TYPE: PRT
<213> ORGANISM: Artificial Sequence
<220> FEATURE:
<223> OTHER INFORMATION: HBV CONSENSUS SEQUENCE -continued

<400> SEQUENCE: 63

Ala Val Thr Asn Phe Leu Leu Ser Leu Gly Ile His Leu Asn Pro Asn
1               5                   10                  15

Lys Thr Lys Arg Trp Gly Tyr Ser Leu Asn Phe Met Gly Tyr Val Ile
            20                  25                  30

Gly Ser Trp Gly Thr Leu
        35

<210> SEQ ID NO 64
<211> LENGTH: 41
<212> TYPE: PRT
<213> ORGANISM: Artificial Sequence
<220> FEATURE:
<223> OTHER INFORMATION: HBV CONSENSUS SEQUENCE

<400> SEQUENCE: 64

Phe Ala Asp Ala Thr Pro Thr Gly Trp Gly Leu Ala Ile Gly His Gln
1               5                   10                  15

Arg Met Arg Gly Thr Phe Val Ala Pro Leu Pro Ile His Thr Ala Glu
            20                  25                  30

Leu Leu Ala Ala Cys Phe Ala Arg Ser
        35                  40

<210> SEQ ID NO 65
<211> LENGTH: 41
<212> TYPE: PRT
<213> ORGANISM: Artificial Sequence
<220> FEATURE:
<223> OTHER INFORMATION: HBV CONSENSUS SEQUENCE

<400> SEQUENCE: 65

Pro Ala Asp Asp Pro Ser Arg Gly Arg Leu Gly Leu Tyr Arg Pro Leu
1               5                   10                  15

Leu Arg Leu Pro Phe Arg Pro Thr Thr Gly Arg Thr Ser Leu Tyr Ala
            20                  25                  30

Val Ser Pro Ser Val Pro Ser His Leu
        35                  40

<210> SEQ ID NO 66
<211> LENGTH: 42
<212> TYPE: PRT
<213> ORGANISM: Artificial Sequence
<220> FEATURE:
<223> OTHER INFORMATION: HBV CONSENSUS SEQUENCE

<400> SEQUENCE: 66

Pro Leu Leu Arg Leu Pro Phe Arg Pro Thr Thr Gly Arg Thr Ser Leu
1               5                   10                  15

Tyr Ala Val Ser Pro Ser Val Pro Ser His Leu Pro Asp Arg Val His
            20                  25                  30

Phe Ala Ser Pro Leu His Val Ala Trp Arg
        35                  40

<210> SEQ ID NO 67
<211> LENGTH: 35
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (15)..(15)
<223> OTHER INFORMATION: C OR S

<400> SEQUENCE: 67

His Cys Ser Pro His His Thr Ala Leu Arg Gln Ala Ile Leu Xaa Trp
1               5                   10                  15

Gly Glu Leu Met Thr Leu Ala Thr Trp Val Gly Ser Asn Leu Glu Asp
            20                  25                  30

Pro Ala Ser
        35

<210> SEQ ID NO 68
<211> LENGTH: 27
<212> TYPE: PRT
<213> ORGANISM: Artificial Sequence
<220> FEATURE:
<223> OTHER INFORMATION: HBV CONSENSUS SEQUENCE

<400> SEQUENCE: 68

Ala Ser Arg Asp Leu Val Val Ser Tyr Val Asn Thr Asn Met Gly Leu
1               5                   10                  15

Lys Ile Arg Gln Leu Leu Trp Phe His Ile Ser
            20                  25

<210> SEQ ID NO 69
<211> LENGTH: 40
<212> TYPE: PRT
<213> ORGANISM: Artificial Sequence
<220> FEATURE:
<223> OTHER INFORMATION: HBV CONSENSUS SEQUENCE

<400> SEQUENCE: 69

Ala Ser Arg Asp Leu Val Val Ser Tyr Val Asn Thr Asn Met Gly Leu
1               5                   10                  15

Lys Ile Arg Gln Leu Leu Trp Phe His Ile Ser Cys Leu Thr Phe Gly
            20                  25                  30

Arg Glu Thr Val Leu Glu Tyr Leu
        35                  40

<210> SEQ ID NO 70
<211> LENGTH: 46
<212> TYPE: PRT
<213> ORGANISM: Artificial Sequence
<220> FEATURE:
<223> OTHER INFORMATION: HBV CONSENSUS SEQUENCE

<400> SEQUENCE: 70

Ser Ala Gly Pro Cys Ala Leu Arg Phe Thr Ser Ala Arg Arg Met Glu
1               5                   10                  15

Thr Thr Val Asn Ala His Gln Ile Leu Pro Lys Val Leu His Lys Arg
            20                  25                  30

Thr Leu Gly Leu Ser Ala Met Ser Thr Thr Asp Leu Glu Ala
        35                  40                  45

<210> SEQ ID NO 71
<211> LENGTH: 43
<212> TYPE: PRT
<213> ORGANISM: Artificial Sequence
<220> FEATURE:
<223> OTHER INFORMATION: HBV CONSENSUS SEQUENCE

<400> SEQUENCE: 71

Thr Ser Gly Phe Leu Gly Pro Leu Leu Val Leu Gln Ala Gly Phe Phe
1               5                   10                  15

Leu Leu Thr Arg Ile Leu Thr Ile Pro Gln Ser Leu Asp Ser Trp Trp
            20                  25                  30

Thr Ser Leu Asn Phe Leu Gly Gly Thr Pro Val
        35                  40

<210> SEQ ID NO 72
<211> LENGTH: 41
<212> TYPE: PRT
<213> ORGANISM: Artificial Sequence
<220> FEATURE:
<223> OTHER INFORMATION: HBV CONSENSUS SEQUENCE

<400> SEQUENCE: 72

Ala Phe Gly Lys Tyr Leu Trp Glu Trp Ala Ser Ala Arg Phe Ser Trp
1               5                   10                  15

Leu Ser Leu Leu Val Pro Phe Val Gln Trp Phe Val Gly Leu Ser Pro
            20                  25                  30

Thr Val Trp Leu Ser Val Ile Trp Met
        35                  40

<210> SEQ ID NO 73
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 73

Leu Pro Arg Leu Ala Asp Glu Gly Leu Asn Arg Arg Val Ala Glu Asp
1               5                   10                  15

Leu Asn Leu

<210> SEQ ID NO 74
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 74

Glu Gly Leu Asn Arg Arg Val Ala Glu Asp Leu Asn Leu Gly Asn Leu
1               5                   10                  15

Asn Val Ser Ile
            20

<210> SEQ ID NO 75
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 75

Ala Glu Asp Leu Asn Leu Gly Asn Leu Asn Val Ser Ile Pro Trp Thr
1               5                   10                  15

His Lys Val

<210> SEQ ID NO 76
<211> LENGTH: 18
<212> TYPE: PRT
<213> ORGANISM: Artificial Sequence
<220> FEATURE:
<223> OTHER INFORMATION: HBV CONSENSUS SEQUENCE

```
<400> SEQUENCE: 76

Asn Leu Gly Asn Leu Asn Val Ser Ile Pro Trp Thr His Lys Val Gly
1               5                   10                  15

Asn Phe

<210> SEQ ID NO 77
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 77

Leu Asn Val Ser Ile Pro Trp Thr His Lys Val Gly Asn Phe Thr Gly
1               5                   10                  15

Leu Tyr Ser Ser
            20

<210> SEQ ID NO 78
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 78

Thr His Lys Val Gly Asn Phe Thr Gly Leu Tyr Ser Ser Thr Val Pro
1               5                   10                  15

Val Phe Asn Pro
            20

<210> SEQ ID NO 79
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 79

Gly Leu Tyr Ser Ser Thr Val Pro Val Phe Asn Pro Glu Trp Gln Thr
1               5                   10                  15

Pro Ser Phe

<210> SEQ ID NO 80
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 80

Lys Gln Gln Phe Val Gly Pro Leu Thr Val Asn Glu Lys Arg Arg Leu
1               5                   10                  15

Lys Leu Ile Met
            20

<210> SEQ ID NO 81
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 81
```

Leu Thr Val Asn Glu Lys Arg Arg Leu Lys Leu Ile Met Pro Ala Arg
1               5                   10                  15

Phe Tyr Pro Asn
            20

<210> SEQ ID NO 82
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 82

Arg Leu Lys Leu Ile Met Pro Ala Arg Phe Tyr Pro Asn Val Thr Lys
1               5                   10                  15

Tyr Leu Pro Leu
            20

<210> SEQ ID NO 83
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 83

Ala Arg Phe Tyr Pro Asn Val Thr Lys Tyr Leu Pro Leu Asp Lys Gly
1               5                   10                  15

Ile Lys Pro Tyr
            20

<210> SEQ ID NO 84
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 84

Thr Lys Tyr Leu Pro Leu Asp Lys Gly Ile Lys Pro Tyr Tyr Pro Glu
1               5                   10                  15

His Val Val

<210> SEQ ID NO 85
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 85

Asp Lys Gly Ile Lys Pro Tyr Tyr Pro Glu His Val Val Asn His Tyr
1               5                   10                  15

Phe Gln Thr Arg
            20

<210> SEQ ID NO 86
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 86

Tyr Pro Glu His Val Val Asn His Tyr Phe Gln Thr Arg His Tyr Leu
1               5                   10                  15

His Thr Leu

<210> SEQ ID NO 87
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 87

Asn His Tyr Phe Gln Thr Arg His Tyr Leu His Thr Leu Trp Lys Ala
1               5                   10                  15

Gly Ile Leu Tyr
            20

<210> SEQ ID NO 88
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 88

Arg His Tyr Leu His Thr Leu Trp Lys Ala Gly Ile Leu Tyr Lys Arg
1               5                   10                  15

Glu Thr Thr Arg
            20

<210> SEQ ID NO 89
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 89

Trp Lys Ala Gly Ile Leu Tyr Lys Arg Glu Thr Thr Arg Ser Ala Ser
1               5                   10                  15

Phe Cys Gly Ser
            20

<210> SEQ ID NO 90
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 90

Arg Glu Thr Thr Arg Ser Ala Ser Phe Cys Gly Ser Pro Tyr Ser Trp
1               5                   10                  15

Glu Gln Glu Leu
            20

<210> SEQ ID NO 91
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 91

```
Ser Phe Cys Gly Ser Pro Tyr Ser Trp Glu Gln Glu Leu Gln Ser Cys
1               5                   10                  15

Trp Trp Leu Gln
            20

<210> SEQ ID NO 92
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 92

Cys Thr Glu His Gly Glu His His Ile Arg Ile Pro Arg Thr Pro Ala
1               5                   10                  15

Arg Val

<210> SEQ ID NO 93
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 93

His His Ile Arg Ile Pro Arg Thr Pro Ala Arg Val Thr Gly Gly Val
1               5                   10                  15

Phe Leu Val

<210> SEQ ID NO 94
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 94

Arg Thr Pro Ala Arg Val Thr Gly Gly Val Phe Leu Val Asp Lys Asn
1               5                   10                  15

Pro His Asn

<210> SEQ ID NO 95
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 95

Thr Gly Gly Val Phe Leu Val Asp Lys Asn Pro His Asn Thr Thr Glu
1               5                   10                  15

Ser Arg Leu Val
            20

<210> SEQ ID NO 96
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 96

Asp Lys Asn Pro His Asn Thr Thr Glu Ser Arg Leu Val Val Asp Phe
```

Ser Gln Phe Ser
            20

<210> SEQ ID NO 97
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 97

Thr Glu Ser Arg Leu Val Val Asp Phe Ser Gln Phe Ser Arg Gly Asn
1               5                   10                  15

Thr Arg Val

<210> SEQ ID NO 98
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 98

Lys Phe Ala Val Pro Asn Leu Gln Ser Leu Thr Asn Leu Leu Ser Ser
1               5                   10                  15

Asn Leu Ser Trp
            20

<210> SEQ ID NO 99
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 99

Leu Gln Ser Leu Thr Asn Leu Leu Ser Ser Asn Leu Ser Trp Leu Ser
1               5                   10                  15

Leu Asp Val

<210> SEQ ID NO 100
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 100

Leu Leu Ser Ser Asn Leu Ser Trp Leu Ser Leu Asp Val Ser Ala Ala
1               5                   10                  15

Phe Tyr

<210> SEQ ID NO 101
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 101

Leu Ser Trp Leu Ser Leu Asp Val Ser Ala Ala Phe Tyr His Ile Pro
1               5                   10                  15

-continued

Leu His Pro Ala
            20

<210> SEQ ID NO 102
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 102

Val Ser Ala Ala Phe Tyr His Ile Pro Leu His Pro Ala Ala Met Pro
1               5                   10                  15

His Leu Leu Val
            20

<210> SEQ ID NO 103
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 103

Leu His Pro Ala Ala Met Pro His Leu Leu Val Gly Ser Ser Gly Leu
1               5                   10                  15

Ser Arg Tyr

<210> SEQ ID NO 104
<211> LENGTH: 22
<212> TYPE: PRT
<213> ORGANISM: Artificial Sequence
<220> FEATURE:
<223> OTHER INFORMATION: HBV CONSENSUS SEQUENCE

<400> SEQUENCE: 104

His Leu Leu Val Gly Ser Ser Gly Leu Ser Arg Tyr Val Ala Arg Leu
1               5                   10                  15

Ser Ser Asn Ser Arg Ile
            20

<210> SEQ ID NO 105
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 105

Gly Thr Met Gln Asn Leu His Asp Ser Cys Ser Arg Asn Leu Tyr Val
1               5                   10                  15

Ser Leu Met Leu
            20

<210> SEQ ID NO 106
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 106

Asp Ser Cys Ser Arg Asn Leu Tyr Val Ser Leu Met Leu Leu Tyr Lys
1               5                   10                  15

Thr Tyr Gly Arg
        20

<210> SEQ ID NO 107
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 107

Tyr Val Ser Leu Met Leu Leu Tyr Lys Thr Tyr Gly Arg Lys Leu His
1               5                   10                  15

Leu Tyr Ser His
        20

<210> SEQ ID NO 108
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 108

Tyr Lys Thr Tyr Gly Arg Lys Leu His Leu Tyr Ser His Pro Ile Ile
1               5                   10                  15

Leu Gly Phe Arg
        20

<210> SEQ ID NO 109
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 109

Lys Leu His Leu Tyr Ser His Pro Ile Ile Leu Gly Phe Arg Lys Ile
1               5                   10                  15

Pro Met Gly Val
        20

<210> SEQ ID NO 110
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 110

Pro Ile Ile Leu Gly Phe Arg Lys Ile Pro Met Gly Val Gly Leu Ser
1               5                   10                  15

Pro Phe Leu

<210> SEQ ID NO 111
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 111

Arg Lys Ile Pro Met Gly Val Gly Leu Ser Pro Phe Leu Leu Ala Gln
1               5                   10                  15

```
Phe Thr Ser Ala
            20

<210> SEQ ID NO 112
<211> LENGTH: 20
<212> TYPE: PRT
<213> ORGANISM: Artificial Sequence
<220> FEATURE:
<223> OTHER INFORMATION: HBV CONSENSUS SEQUENCE
<220> FEATURE:
<221> NAME/KEY: MISC_FEATURE
<222> LOCATION: (15)..(15)
<223> OTHER INFORMATION: C OR S

<400> SEQUENCE: 112

Gly Leu Ser Pro Phe Leu Leu Ala Gln Phe Thr Ser Ala Ile Xaa Ser
1               5                   10                  15

Val Val Arg Arg
            20

<210> SEQ ID NO 113
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 113

Leu Leu Ala Gln Phe Thr Ser Ala Ile Cys Ser Val Val Arg Arg Ala
1               5                   10                  15

Phe Pro His

<210> SEQ ID NO 114
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 114

Ser Ala Ile Cys Ser Val Val Arg Arg Ala Phe Pro His Cys Leu Ala
1               5                   10                  15

Phe Ser Tyr Met
            20

<210> SEQ ID NO 115
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 115

Arg Ala Phe Pro His Cys Leu Ala Phe Ser Tyr Met Asp Asp Val Val
1               5                   10                  15

Leu Gly Ala

<210> SEQ ID NO 116
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 116
```

```
Leu Ala Phe Ser Tyr Met Asp Asp Val Val Leu Gly Ala Lys Ser Val
1               5                   10                  15

Gln His Leu
```

<210> SEQ ID NO 117
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 117

```
Tyr Met Asp Asp Val Val Leu Gly Ala Lys Ser Val Gln His Leu Glu
1               5                   10                  15

Ser Leu Tyr
```

<210> SEQ ID NO 118
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 118

```
Leu Gly Ala Lys Ser Val Gln His Leu Glu Ser Leu Tyr Thr Ala Val
1               5                   10                  15

Thr Asn Phe Leu
            20
```

<210> SEQ ID NO 119
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 119

```
His Leu Glu Ser Leu Tyr Thr Ala Val Thr Asn Phe Leu Leu Ser Leu
1               5                   10                  15

Gly Ile His Leu
            20
```

<210> SEQ ID NO 120
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 120

```
Ala Val Thr Asn Phe Leu Leu Ser Leu Gly Ile His Leu Asn Pro Asn
1               5                   10                  15

Lys Thr Lys Arg
            20
```

<210> SEQ ID NO 121
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 121

```
Ser Leu Gly Ile His Leu Asn Pro Asn Lys Thr Lys Arg Trp Gly Tyr
```

```
                1               5                   10                  15

Ser Leu Asn Phe
            20

<210> SEQ ID NO 122
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 122

His Leu Asn Pro Asn Lys Thr Lys Arg Trp Gly Tyr Ser Leu Asn Phe
1               5                   10                  15

Met Gly Tyr Val
            20

<210> SEQ ID NO 123
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 123

Lys Arg Trp Gly Tyr Ser Leu Asn Phe Met Gly Tyr Val Ile Gly Ser
1               5                   10                  15

Trp Gly Thr Leu
            20

<210> SEQ ID NO 124
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 124

Lys Ile Lys Gln Cys Phe Arg Lys Leu Pro Val Asn Arg Pro Ile Asp
1               5                   10                  15

Trp Lys

<210> SEQ ID NO 125
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 125

Phe Arg Lys Leu Pro Val Asn Arg Pro Ile Asp Trp Lys Val Cys Gln
1               5                   10                  15

Arg Ile Val Gly
            20

<210> SEQ ID NO 126
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 126

Arg Pro Ile Asp Trp Lys Val Cys Gln Arg Ile Val Gly Leu Leu Gly
```

```
1               5                   10                  15

Phe Ala Ala

<210> SEQ ID NO 127
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 127

Val Cys Gln Arg Ile Val Gly Leu Leu Gly Phe Ala Ala Pro Phe Thr
1               5                   10                  15

Gln Cys Gly Tyr
            20

<210> SEQ ID NO 128
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 128

Gly Leu Leu Gly Phe Ala Ala Pro Phe Thr Gln Cys Gly Tyr Pro Ala
1               5                   10                  15

Leu Met Pro Leu
            20

<210> SEQ ID NO 129
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 129

Phe Thr Gln Cys Gly Tyr Pro Ala Leu Met Pro Leu Tyr Ala Cys Ile
1               5                   10                  15

Gln Ala Lys

<210> SEQ ID NO 130
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 130

Ala Leu Met Pro Leu Tyr Ala Cys Ile Gln Ala Lys Gln Ala Phe Thr
1               5                   10                  15

Phe Ser Pro Thr
            20

<210> SEQ ID NO 131
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 131

Ile Gln Ala Lys Gln Ala Phe Thr Phe Ser Pro Thr Tyr Lys Ala Phe
1               5                   10                  15
```

```
<210> SEQ ID NO 132
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 132

Phe Thr Phe Ser Pro Thr Tyr Lys Ala Phe Leu Cys Lys Gln Tyr Leu
1               5                   10                  15

Asn Leu Tyr

<210> SEQ ID NO 133
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 133

Tyr Lys Ala Phe Leu Cys Lys Gln Tyr Leu Asn Leu Tyr Pro Val Ala
1               5                   10                  15

Arg Gln Arg

<210> SEQ ID NO 134
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 134

Lys Gln Tyr Leu Asn Leu Tyr Pro Val Ala Arg Gln Arg Pro Gly Leu
1               5                   10                  15

Cys Gln Val

<210> SEQ ID NO 135
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 135

Tyr Pro Val Ala Arg Gln Arg Pro Gly Leu Cys Gln Val Phe Ala Asp
1               5                   10                  15

Ala Thr Pro Thr
            20

<210> SEQ ID NO 136
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 136

Gly Leu Cys Gln Val Phe Ala Asp Ala Thr Pro Thr Gly Trp Gly Leu
1               5                   10                  15

Ala Ile
```

<210> SEQ ID NO 137
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 137

Phe Ala Asp Ala Thr Pro Thr Gly Trp Gly Leu Ala Ile Gly His Gln
1               5                   10                  15

Arg Met Arg

<210> SEQ ID NO 138
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 138

Gly Trp Gly Leu Ala Ile Gly His Gln Arg Met Arg Gly Thr Phe Val
1               5                   10                  15

Ala Pro Leu

<210> SEQ ID NO 139
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 139

Gly His Gln Arg Met Arg Gly Thr Phe Val Ala Pro Leu Pro Ile His
1               5                   10                  15

Thr Ala Glu Leu
            20

<210> SEQ ID NO 140
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 140

Phe Val Ala Pro Leu Pro Ile His Thr Ala Glu Leu Leu Ala Ala Cys
1               5                   10                  15

Phe Ala Arg Ser
            20

<210> SEQ ID NO 141
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 141

His Thr Ala Glu Leu Leu Ala Ala Cys Phe Ala Arg Ser Arg Ser Gly
1               5                   10                  15

Ala Lys Leu Ile
            20

```
<210> SEQ ID NO 142
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 142

Ala Cys Phe Ala Arg Ser Arg Ser Gly Ala Lys Leu Ile Gly Thr Asp
1               5                   10                  15

Asn Ser Val Val
            20

<210> SEQ ID NO 143
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 143

Gly Ala Lys Leu Ile Gly Thr Asp Asn Ser Val Val Leu Ser Arg Lys
1               5                   10                  15

Tyr Thr Ser Phe
            20

<210> SEQ ID NO 144
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 144

Asp Asn Ser Val Val Leu Ser Arg Lys Tyr Thr Ser Phe Pro Trp Leu
1               5                   10                  15

Leu Gly Cys Ala
            20

<210> SEQ ID NO 145
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 145

Arg Lys Tyr Thr Ser Phe Pro Trp Leu Leu Gly Cys Ala Ala Asn Trp
1               5                   10                  15

Ile Leu

<210> SEQ ID NO 146
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 146

Phe Pro Trp Leu Leu Gly Cys Ala Ala Asn Trp Ile Leu Arg Gly Thr
1               5                   10                  15

Ser Phe Val

<210> SEQ ID NO 147
```

<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 147

Ala Ala Asn Trp Ile Leu Arg Gly Thr Ser Phe Val Tyr Val Pro Ser
1               5                   10                  15

Ala Leu Asn

<210> SEQ ID NO 148
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 148

Ile Leu Arg Gly Thr Ser Phe Val Tyr Val Pro Ser Ala Leu Asn Pro
1               5                   10                  15

Ala Asp Asp Pro Ser
            20

<210> SEQ ID NO 149
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 149

Tyr Val Pro Ser Ala Leu Asn Pro Ala Asp Asp Pro Ser Arg Gly Arg
1               5                   10                  15

Leu Gly Leu Tyr
            20

<210> SEQ ID NO 150
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 150

Pro Ala Asp Asp Pro Ser Arg Gly Arg Leu Gly Leu Tyr Arg Pro Leu
1               5                   10                  15

Leu Arg Leu

<210> SEQ ID NO 151
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 151

Arg Leu Gly Leu Tyr Arg Pro Leu Leu Arg Leu Pro Phe Arg Pro Thr
1               5                   10                  15

Thr Gly Arg

<210> SEQ ID NO 152
<211> LENGTH: 19
<212> TYPE: PRT

<213> ORGANISM: Artificial Sequence
<220> FEATURE:
<223> OTHER INFORMATION: HBV CONSENSUS SEQUENCE

<400> SEQUENCE: 152

Pro Leu Leu Arg Leu Pro Phe Arg Pro Thr Thr Gly Arg Thr Ser Leu
1               5                   10                  15

Tyr Ala Val

<210> SEQ ID NO 153
<211> LENGTH: 17
<212> TYPE: PRT
<213> ORGANISM: Artificial Sequence
<220> FEATURE:
<223> OTHER INFORMATION: HBV CONSENSUS SEQUENCE

<400> SEQUENCE: 153

Phe Arg Pro Thr Thr Gly Arg Thr Ser Leu Tyr Ala Val Ser Pro Ser
1               5                   10                  15

Val

<210> SEQ ID NO 154
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 154

Thr Thr Gly Arg Thr Ser Leu Tyr Ala Val Ser Pro Ser Val Pro Ser
1               5                   10                  15

His Leu

<210> SEQ ID NO 155
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 155

Ser Leu Tyr Ala Val Ser Pro Ser Val Pro Ser His Leu Pro Asp Arg
1               5                   10                  15

Val His Phe Ala
            20

<210> SEQ ID NO 156
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 156

Ser Val Pro Ser His Leu Pro Asp Arg Val His Phe Ala Ser Pro Leu
1               5                   10                  15

His Val Ala Trp Arg
            20

<210> SEQ ID NO 157
<211> LENGTH: 19
<212> TYPE: PRT
<213> ORGANISM: Artificial Sequence
<220> FEATURE:

```
<223> OTHER INFORMATION: HBV CONSENSUS SEQUENCE

<400> SEQUENCE: 157

Met Gln Leu Phe His Leu Cys Le

```
Ile Asp Pro Tyr Lys Glu Phe Gly Ala Ser Val Glu Leu Leu Ser Phe
1               5                   10                  15

Leu Pro Ser Asp
            20
```

<210> SEQ ID NO 163
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 163

```
Lys Glu Phe Gly Ala Ser Val Glu Leu Leu Ser Phe Leu Pro Ser Asp
1               5                   10                  15

Phe Phe Pro Ser Val
            20
```

<210> SEQ ID NO 164
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 164

```
Glu Leu Leu Ser Phe Leu Pro Ser Asp Phe Phe Pro Ser Val Arg Asp
1               5                   10                  15

Leu Leu
```

<210> SEQ ID NO 165
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 165

```
Phe Leu Pro Ser Asp Phe Phe Pro Ser Val Arg Asp Leu Leu Asp Thr
1               5                   10                  15

Ala Ser Ala Leu Tyr
            20
```

<210> SEQ ID NO 166
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 166

```
Ser Val Arg Asp Leu Leu Asp Thr Ala Ser Ala Leu Tyr Arg Glu Ala
1               5                   10                  15

Leu Glu Ser
```

<210> SEQ ID NO 167
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 167

Asp Thr Ala Ser Ala Leu Tyr Arg Glu Ala Leu Glu Ser Pro Glu His
1               5                   10                  15

Cys Ser Pro His
            20

<210> SEQ ID NO 168
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 168

Arg Glu Ala Leu Glu Ser Pro Glu His Cys Ser Pro His His Thr Ala
1               5                   10                  15

Leu Arg Gln Ala
            20

<210> SEQ ID NO 169
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 169

His Cys Ser Pro His His Thr Ala Leu Arg Gln Ala Ile Leu Cys Trp
1               5                   10                  15

Gly Glu Leu Met
            20

<210> SEQ ID NO 170
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 170

Ala Leu Arg Gln Ala Ile Leu Cys Trp Gly Glu Leu Met Thr Leu Ala
1               5                   10                  15

Thr Trp Val

<210> SEQ ID NO 171
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 171

Trp Gly Glu Leu Met Thr Leu Ala Thr Trp Val Gly Ser Asn Leu Glu
1               5                   10                  15

Asp Pro Ala Ser
            20

<210> SEQ ID NO 172
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 172

```
Ala Ser Arg Asp Leu Val Val Ser Tyr Val Asn Thr Asn Met Gly Leu
1               5                   10                  15

Lys Ile Arg

<210> SEQ ID NO 173
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 173

Ser Tyr Val Asn Thr Asn Met Gly Leu Lys Ile Arg Gln Leu Leu Trp
1               5                   10                  15

Phe His Ile Ser
            20

<210> SEQ ID NO 174
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 174

Gly Leu Lys Ile Arg Gln Leu Leu Trp Phe His Ile Ser Cys Leu Thr
1               5                   10                  15

Phe Gly Arg

<210> SEQ ID NO 175
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 175

Leu Leu Trp Phe His Ile Ser Cys Leu Thr Phe Gly Arg Glu Thr Val
1               5                   10                  15

Leu Glu Tyr Leu
            20

<210> SEQ ID NO 176
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 176

Cys Leu Thr Phe Gly Arg Glu Thr Val Leu Glu Tyr Leu Val Ser Phe
1               5                   10                  15

Gly Val Trp Ile
            20

<210> SEQ ID NO 177
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 177

Thr Val Leu Glu Tyr Leu Val Ser Phe Gly Val Trp Ile Arg Thr Pro
```

```
1               5                   10                  15
Pro Ala Tyr Arg
            20

<210> SEQ ID NO 178
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 178

Ser Phe Gly Val Trp Ile Arg Thr Pro Pro Ala Tyr Arg Pro Pro Asn
1               5                   10                  15
Ala Pro Ile Leu
            20

<210> SEQ ID NO 179
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 179

Thr Pro Pro Ala Tyr Arg Pro Pro Asn Ala Pro Ile Leu Ser Thr Leu
1               5                   10                  15
Pro Glu Thr Thr
            20

<210> SEQ ID NO 180
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 180

Pro Asn Ala Pro Ile Leu Ser Thr Leu Pro Glu Thr Thr Val Val Arg
1               5                   10                  15
Arg Arg Gly Arg
            20

<210> SEQ ID NO 181
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 181

Thr Leu Pro Glu Thr Thr Val Val Arg Arg Arg Gly Arg Ser Pro Arg
1               5                   10                  15
Arg Arg Thr

<210> SEQ ID NO 182
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 182

Val Val Arg Arg Arg Gly Arg Ser Pro Arg Arg Arg Thr Pro Ser Pro
```

```
                1               5                   10                  15

Arg Arg Arg Arg
            20

<210> SEQ ID NO 183
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 183

Ser Pro Arg Arg Arg Thr Pro Ser Pro Arg Arg Arg Arg Ser Gln Ser
1               5                   10                  15

Pro Arg Arg Arg
            20

<210> SEQ ID NO 184
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 184

Ser Pro Arg Arg Arg Arg Ser Gln Ser Pro Arg Arg Arg Ser Gln
1               5                   10                  15

Ser Arg Glu Ser
            20

<210> SEQ ID NO 185
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 185

His Leu Ser Leu Arg Gly Leu Pro Val Cys Ala Phe Ser Ser Ala Gly
1               5                   10                  15

Pro Cys Ala Leu
            20

<210> SEQ ID NO 186
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 186

Leu Pro Val Cys Ala Phe Ser Ser Ala Gly Pro Cys Ala Leu Arg Phe
1               5                   10                  15

Thr Ser Ala Arg
            20

<210> SEQ ID NO 187
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 187
```

```
Ser Ala Gly Pro Cys Ala Leu Arg Phe Thr Ser Ala Arg Arg Met Glu
1               5                   10                  15

Thr Thr Val
```

<210> SEQ ID NO 188
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 188

```
Leu Arg Phe Thr Ser Ala Arg Arg Met Glu Thr Thr Val Asn Ala His
1               5                   10                  15

Gln Ile Leu
```

<210> SEQ ID NO 189
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 189

```
Arg Arg Met Glu Thr Thr Val Asn Ala His Gln Ile Leu Pro Lys Val
1               5                   10                  15

Leu His Lys Arg
            20
```

<210> SEQ ID NO 190
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 190

```
Asn Ala His Gln Ile Leu Pro Lys Val Leu His Lys Arg Thr Leu Gly
1               5                   10                  15

Leu Ser Ala Met
            20
```

<210> SEQ ID NO 191
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 191

```
Lys Val Leu His Lys Arg Thr Leu Gly Leu Ser Ala Met Ser Thr Thr
1               5                   10                  15

Asp Leu Glu Ala
            20
```

<210> SEQ ID NO 192
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 192

```
Leu Gly Leu Ser Ala Met Ser Thr Thr Asp Leu Glu Ala Tyr Phe Lys
```

```
1               5                   10                  15

Asp Cys Val Phe
            20

<210> SEQ ID NO 193
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 193

Thr Thr Asp Leu Glu Ala Tyr Phe Lys Asp Cys Val Phe Lys Asp Trp
1               5                   10                  15

Glu Glu Leu

<210> SEQ ID NO 194
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 194

Tyr Phe Lys Asp Cys Val Phe Lys Asp Trp Glu Glu Leu Gly Glu Glu
1               5                   10                  15

Ile Arg Leu

<210> SEQ ID NO 195
<211> LENGTH: 18
<212> TYPE: PRT
<213> ORGANISM: Artificial Sequence
<220> FEATURE:
<223> OTHER INFORMATION: HBV CONSENSUS SEQUENCE

<400> SEQUENCE: 195

Phe Lys Asp Trp Glu Glu Leu Gly Glu Glu Ile Arg Leu Lys Val Phe
1               5                   10                  15

Val Leu

<210> SEQ ID NO 196
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 196

Glu Leu Gly Glu Glu Ile Arg Leu Lys Val Phe Val Leu Gly Gly Cys
1               5                   10                  15

Arg His Lys Leu
            20

<210> SEQ ID NO 197
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 197

Leu Lys Val Phe Val Leu Gly Gly Cys Arg His Lys Leu Val Cys Ser
1               5                   10                  15
```

Pro Ala Pro Cys
            20

<210> SEQ ID NO 198
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 198

Arg Gln Pro Thr Pro Ile Ser Pro Pro Leu Arg Asp Ser His Pro Gln
1               5                   10                  15

Ala Met Gln Trp
            20

<210> SEQ ID NO 199
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 199

Pro Pro Leu Arg Asp Ser His Pro Gln Ala Met Gln Trp Asn Ser Thr
1               5                   10                  15

Thr Phe His

<210> SEQ ID NO 200
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 200

His Pro Gln Ala Met Gln Trp Asn Ser Thr Thr Phe His Gln Ala Leu
1               5                   10                  15

Gln Asp Pro Arg
            20

<210> SEQ ID NO 201
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 201

Ser Thr Thr Phe His Gln Ala Leu Gln Asp Pro Arg Val Arg Gly Leu
1               5                   10                  15

Tyr Phe Pro Ala
            20

<210> SEQ ID NO 202
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 202

Leu Gln Asp Pro Arg Val Arg Gly Leu Tyr Phe Pro Ala Gly Gly Ser
1               5                   10                  15

Ser Ser Gly

<210> SEQ ID NO 203
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 203

Arg Gly Leu Tyr Phe Pro Ala Gly Gly Ser Ser Ser Gly Thr Val Asn
1               5                   10                  15

Pro Ala Pro Thr
            20

<210> SEQ ID NO 204
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 204

Pro Asn Met Glu Asn Ile Thr Ser Gly Phe Leu Gly Pro Leu Leu Val
1               5                   10                  15

Leu Gln Ala

<210> SEQ ID NO 205
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 205

Thr Ser Gly Phe Leu Gly Pro Leu Leu Val Leu Gln Ala Gly Phe Phe
1               5                   10                  15

Leu Leu Thr Lys
            20

<210> SEQ ID NO 206
<211> LENGTH: 17
<212> TYPE: PRT
<213> ORGANISM: Artificial Sequence
<220> FEATURE:
<223> OTHER INFORMATION: HBV CONSENSUS SEQUENCE

<400> SEQUENCE: 206

Leu Leu Val Leu Gln Ala Gly Phe Phe Leu Leu Thr Lys Ile Leu Thr
1               5                   10                  15

Ile

<210> SEQ ID NO 207
<211> LENGTH: 19
<212> TYPE: PRT
<213> ORGANISM: Artificial Sequence
<220> FEATURE:
<223> OTHER INFORMATION: HBV CONSENSUS SEQUENCE

<400> SEQUENCE: 207

Val Leu Gln Ala Gly Phe Phe Leu Leu Thr Lys Ile Leu Thr Ile Pro
1               5                   10                  15

Gln Ser Leu

```
<210> SEQ ID NO 208
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 208

Phe Leu Leu Thr Lys Ile Leu Thr Ile Pro Gln Ser Leu Asp Ser Trp
1               5                   10                  15

Trp Thr Ser Leu
            20

<210> SEQ ID NO 209
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 209

Thr Ile Pro Gln Ser Leu Asp Ser Trp Trp Thr Ser Leu Asn Phe Leu
1               5                   10                  15

Gly Gly Thr Pro Val
            20

<210> SEQ ID NO 210
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 210

Trp Trp Thr Ser Leu Asn Phe Leu Gly Gly Thr Pro Val Cys Leu Gly
1               5                   10                  15

Gln Asn Ser Gln
            20

<210> SEQ ID NO 211
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 211

Pro Gly Tyr Arg Trp Met Cys Leu Arg Arg Phe Ile Ile Phe Leu Phe
1               5                   10                  15

Ile Leu Leu Leu
            20

<210> SEQ ID NO 212
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 212

Leu Arg Arg Phe Ile Ile Phe Leu Phe Ile Leu Leu Leu Cys Leu Ile
1               5                   10                  15

Phe Leu Leu Val
            20
```

```
<210> SEQ ID NO 213
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 213

Phe Ile Leu Leu Leu Cys Leu Ile Phe Leu Leu Val Leu Leu Asp Tyr
1               5                   10                  15

Gln Gly Met Leu
            20

<210> SEQ ID NO 214
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 214

Ile Pro Ile Pro Ser Ser Trp Ala Phe Gly Lys Tyr Leu Trp Glu Trp
1               5                   10                  15

Ala Ser Ala Arg
            20

<210> SEQ ID NO 215
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 215

Ala Phe Gly Lys Tyr Leu Trp Glu Trp Ala Ser Ala Arg Phe Ser Trp
1               5                   10                  15

Leu Ser Leu Leu
            20

<210> SEQ ID NO 216
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 216

Glu Trp Ala Ser Ala Arg Phe Ser Trp Leu Ser Leu Leu Val Pro Phe
1               5                   10                  15

Val Gln Trp Phe
            20

<210> SEQ ID NO 217
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 217

Ser Trp Leu Ser Leu Leu Val Pro Phe Val Gln Trp Phe Val Gly Leu
1               5                   10                  15

Ser Pro Thr Val
```

```
                        20

<210> SEQ ID NO 218
<211> LENGTH: 20
<212> TYPE: PRT
<213> ORGANISM: Artificial Sequence
<220> FEATURE:
<223> OTHER INFORMATION: HBV CONSENSUS SEQUENCE

<400> SEQUENCE: 218

Pro Phe Val Gln Trp Phe Val Gly Leu Ser Pro Thr Val Trp Leu Ser
1               5                   10                  15

Val Ile Trp Met
            20

<210> SEQ ID NO 219
<211> LENGTH: 21
<212> TYPE: PRT
<213> ORGANISM: Artificial Sequence
<220> FEATURE:
<223> OTHER INFORMATION: HBV CONSENSUS SEQUENCE

<400> SEQUENCE: 219

Gly Leu Ser Pro Thr Val Trp Leu Ser Val Ile Trp Met Met Trp Tyr
1               5                   10                  15

Trp Gly Pro Ser Leu
            20

<210> SEQ ID NO 220
<211> LENGTH: 62
<212> TYPE: PRT
<213> ORGANISM: Artificial Sequence
<220> FEATURE:
<223> OTHER INFORMATION: HBV CONSENSUS SEQUENCE

<400> SEQUENCE: 220

Lys Phe Ala Val Pro Asn Leu Gln Ser Leu Thr Asn Leu Leu Ser Ser
1               5                   10                  15

Asn Leu Ser Trp Leu Ser Leu Asp Val Ser Ala Ala Phe Tyr His Ile
            20                  25                  30

Pro Leu His Pro Ala Ala Met Pro His Leu Leu Val Gly Ser Ser Gly
        35                  40                  45

Leu Ser Arg Tyr Val Ala Arg Leu Ser Ser Asn Ser Arg Ile
    50                  55                  60

<210> SEQ ID NO 221
<211> LENGTH: 33
<212> TYPE: PRT
<213> ORGANISM: Artificial Sequence
<220> FEATURE:
<223> OTHER INFORMATION: HBV CONSENSUS SEQUENCE

<400> SEQUENCE: 221

Gly Pro Leu Leu Val Leu Gln Ala Gly Phe Phe Leu Leu Thr Arg Ile
1               5                   10                  15

Leu Thr Ile Pro Gln Ser Leu Asp Ser Trp Trp Thr Ser Leu Asn Phe
            20                  25                  30

Leu

<210> SEQ ID NO 222
<211> LENGTH: 39
<212> TYPE: PRT
<213> ORGANISM: Artificial Sequence
```

-continued

```
<220> FEATURE:
<223> OTHER INFORMATION: HBV CONSENSUS SEQUENCE

<400> SEQUENCE: 222

Lys Lys Lys Gly Pro Leu Leu Val Leu Gln Ala Gly Phe Phe Leu Leu
1               5                   10                  15

Thr Arg Ile Leu Thr Ile Pro Gln Ser Leu Asp Ser Trp Trp Thr Ser
            20                  25                  30

Leu Asn Phe Leu Lys Lys Lys
            35
```

VACCINES AGAINST HEPATITIS B VIRUS

CROSS-REFERENCE TO RELATED APPLICATIONS

This application is a Divisional application of U.S. Ser. No. 14/655,041, which was filed 7 Jan. 2016 and is currently pending, which is a U.S. National stage application filed under 35 USC § 371 of International Application No. PCT/GB2013/053410, filed 20 Dec. 2013, which claims priority to and the benefit of Great Britain Patent Application No. GB 1223386.2 filed 24 Dec. 2012, the entire contents of which are incorporated herein by reference.

SEQUENCE LISTING

This application hereby incorporates by reference the material of the electronic Sequencing Listing filed concurrently herewith. The materials in the electronic Sequence Listing is submitted as a text (.txt) file entitled "IPF05.US2_Seqlist.txt" created on Sep. 23, 2019, which has a file size of 100,110 bytes, and is herein incorporated by reference in its entirety.

FIELD OF THE INVENTION

The present invention relates to an immunogenic HBV peptide composition and to the treatment of HBV using the composition.

BACKGROUND OF THE INVENTION

Hepatitis B virus (HBV) infection is a major cause of liver-related morbidity and mortality in Europe and worldwide. An estimated 650,000 individuals die each year from liver failure or hepatocellular carcinoma. Even though vaccination programs have led to declines in de novo HBV infections in many countries, chronic hepatitis B (CHB) is a rapidly growing problem in Europe due to immigration of HBV carriers from endemic areas.

From a conceptual standpoint, chronic HBV infection can be classified into three phases (or types of immune responses): immune tolerant, immune active and inactive chronic carrier. These distinct phases of chronic infection correspond with characteristic serologic patterns and correlate with the patient's immune response to HBV. In general, patients with persistent immune active chronic HBV infection receive HBV therapy.

Limited treatment options are available for chronic hepatitis B (CHB). Suppression of viral replication with antivirals such as interferon-alpha and nucleoside/nucleotide analogues (NUCs) is the only way to reduce morbidity and mortality from chronic HBV infection with the ultimate aim of improving survival. Nevertheless, the loss of serum HBsAg and development of anti-HBs antibodies (seroconversion) is the hallmark of a successful immunological response to HBV infection and the closest outcome to clinical cure. Only interferon-alpha has been able to induce significant HBsAg loss but in a relatively low proportion of patients (10%). Interferons have a high cost, a poor tolerability and some HBV genotypes remain poorly responsive to treatment.

Consequently, NUCs remain the main treatment strategies with five NUCs being approved in Europe to treat CHB. The most potent and preferred drugs, tenofovir and entecavir, have a very favorable side-effect profile and are able to induce HBV DNA suppression in almost all patients. However, life-long therapy is required for the majority of patients under most national and international guidelines. Only very few HBeAg-positive patients, and no HBeAg-negative patients, are able to clear HBsAg even after several years of NUC therapy. The long-term safety of NUC therapy is currently unknown. Therefore, concepts to enable a timely cessation of NUC therapy are urgently needed.

Therapeutic vaccination is a promising intervention for hepatitis B as a way to induce immune control over the disease. T-cell responses have been shown to be critical for clearance of acute HBV infection. However, therapeutic HBV vaccines based on HBsAg have failed to show benefit due to induced immune tolerance from high levels of circulating HBsAg, even under effective antiviral treatment.

SUMMARY OF THE INVENTION

The present inventors have identified regions of the HBV proteome that have a high degree of conservation between different HBV genotypes and that have unexpectedly better immunogenic properties compared to other similarly conserved regions of HBV proteins. In particular, the inventors have unexpectedly shown using an in vitro assay that peptide sequences within particular domains of HBV polymerase and HBV core protein are able to elicit a response in PBMC from chronically infected HBV patients infected with different HBV genotypes and/or from chronically infected HBV patients of different ethnicities. In particular, the inventors have surprisingly identified an immunodominant region in the terminal domain of HBV polymerase.

Accordingly, the present invention provides a pharmaceutical composition comprising at least two peptides of from 15 to 60 amino acids in length, selected from peptides comprising a sequence of at least 15 contiguous amino acids of one of the sequences shown in SEQ ID NOs: 1 to 4 or of a sequence having at least 80% identity to one of the sequences shown in SEQ ID NOs: 1 to 4, wherein each peptide comprises at least one CD8+ T-cell epitope and/or at least one CD4+ T-cell epitope and wherein each peptide elicits a response in peripheral blood mononuclear cells (PBMC) from at least one chronically infected HBV individual in an in vitro assay.

The composition may comprise at least one peptide comprising at least 15 amino acids of one of the sequences shown in SEQ ID NOs: 1 to 3 and at least one peptide comprising at least 15 amino acids of the sequence shown in SEQ ID NO: 4.

At least one of the peptides may comprise a sequence shown in one of SEQ ID NOs: 24 to 33, or a sequence having at least 80% identity to one of the sequences shown in SEQ ID NOs: 24 to 33. One or more of the peptides may comprise one or more amino acid(s) at the N-terminus and/or C-terminus to increase the net positive charge and/or to reduce hydrophobicity of the peptide. The composition may therefore comprise a peptide comprising a sequence shown in one of SEQ ID NOs: 34 to 38.

The composition may further comprise at least one peptide derived from HBV surface protein. The peptides derived from HBV surface protein may be of from 15 to 60 amino acids in length and comprise a sequence of at least 15 contiguous amino acids of the sequence shown in SEQ ID NO: 55 or of a sequence having at least 80% identity to at least 15 contiguous amino acids of the sequence shown in SEQ ID NO: 55, wherein the peptide comprises at least one CD8+ T-cell epitope and/or at least one CD4+ T-cell epitope and elicits a response in peripheral blood mononuclear cells (PBMC) from at least one chronically infected HBV individual in an in vitro assay.

The composition, wherein said composition is capable of eliciting an immune response in PBMC from at least two individuals of different ethnicities and from two individuals infected with different HBV genotypes.

The composition may be capable of eliciting an immune response: (a) in PBMC from two, three or all of: an individual infected with HBV genotype A, an individual infected with HBV genotype B, an individual infected with HBV genotype C and an individual infected with HBV genotype D; and/or in PBMC from two, three or all of: an Oriental or Indian individual infected with HBV, a Caucasian individual infected with HBV and an African or Arabic individual infected with HBV.

The peptides in a composition of the invention may be linked to a fluorocarbon vector. The composition may further comprise HBc, HBe, or HBs antigen and/or an adjuvant.

The invention provides the composition of the invention for use in the treatment or prevention of HBV infection, particularly for the treatment of HBeAg-negative patients or HBeAg-positive patients. The composition of the invention may be used in combination with: (i) interferon-alpha and/or nucleoside/ nucleotide analogues (NUCs); and/or (ii) anti-PD1 blocking antibodies, anti-CTLA4 blocking antibodies, anti-PD1L blocking antibodies, anti-LAG3 blocking antibodies, anti-TIM3 blocking antibodies and/or cyclophosphamide. Treatment with the composition may result in HBsAg loss or HBsAg seroconversion.

The invention also provides the composition of the invention for use in the treatment or prevention of end-stage liver disease or hepatocellular carcinoma or for use in the treatment or prevention of hepatitis D virus (HDV) infection.

A method of treating or preventing HBV infection, the method comprising administering to a subject in need thereof a therapeutically effective amount of a composition according to the invention, and the use of a composition according to the invention in the manufacture of a medicament for the treatment or prevention of HBV are also provided.

In addition, the invention provides a peptide of from 15 to 60 amino acids in length comprising at least 15 contiguous amino acids of the sequence shown in anyone of SEQ ID NOs: 1 to 4 or of a sequence having at least 80% identity to one of the sequences shown in SEQ ID NOs: 1 to 4, which peptide comprises at least one CD8+ T-cell epitope and/or at least one CD4+ T-cell epitope and is capable of eliciting a response in peripheral blood mononuclear cells (PBMC) from at least one chronically infected HBV individual in an in vitro assay. The peptide of may comprise at least 15 contiguous amino acids of the sequence shown in SEQ ID NO: 5, 6, 14 or 15.

The invention also provides a peptide comprising one of the sequences shown in SEQ ID NOs: 24 to 38, or a sequence having at least 80% identity to one of the sequences shown in SEQ ID NOs: 24 to 38.

The peptide of the invention may be covalently linked to a fluorocarbon vector.

BRIEF DESCRIPTION OF THE FIGURES

FIGS. 13A, 13B, 13C, 13D and 13E correspond to results obtained for groups of individuals infected by HBV genotypes A, B, C, D and non-A/B/C/D respectively. Following a 10 day culture with the nine unconjugated HBV peptides (NP113, NP151, NP277(K), NP376, NP753(K), NP797(K), NP856 (K), NP877 and NP1266(K)) (0.1 μg/peptide/mL), PBMC were restimulated in an 18 h IFNγ ELISpot assay with individual peptides at a concentration of 5 μg/ml. Results are expressed as cytokine-producing cells, as a percentage of parent CD3/CD4 or CD3/CD8 T cell populations. Stimulation in culture medium or PMA/ionomycin were used as negative and positive controls respectively and the gating strategy was based on negative control IFNγ production.

BRIEF DESCRIPTION OF THE SEQUENCE LISTING

Figure 1:
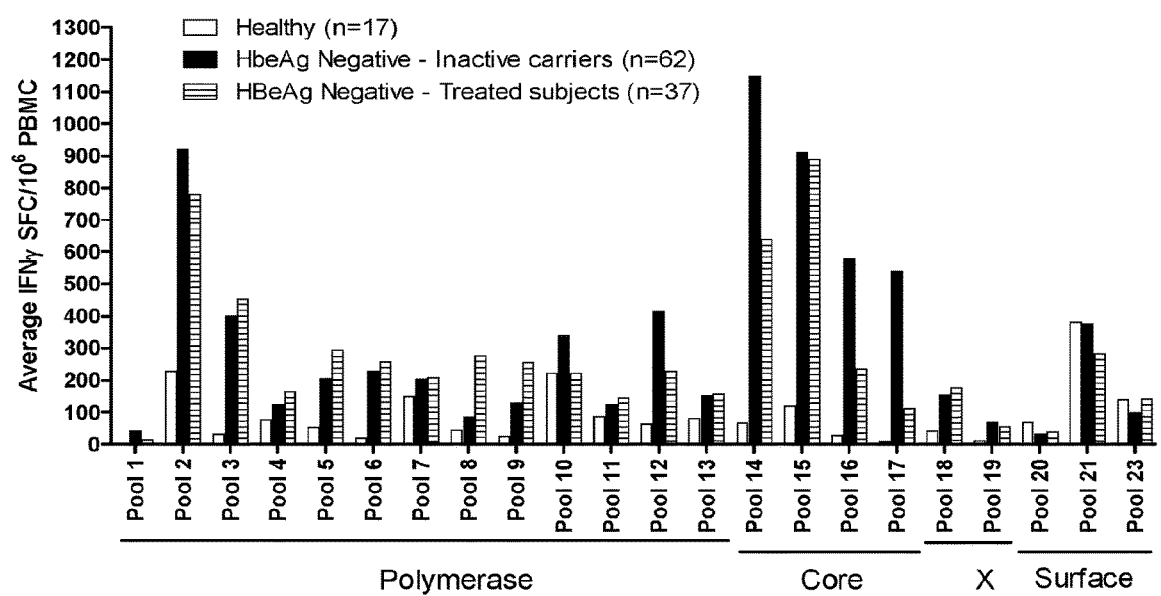
FIG. 1 is a comparison of IFNγ responses in chronic HBV-infected subjects in immune control phase or undergoing active treatment. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

SEQ ID NOs: 1 to 38 and 40 to 72 are the amino acid sequences of regions of the reference HBV sequence shown in SEQ ID NO: 39 of HBV polymerase as shown in Table 1 below.

| SEQ ID NO: | Reference in Examples | Region of virtual HBV proteome sequence | HBV protein |
|---|---|---|---|
| 1 | Pools 2/3 | 93-186 | polymerase |
| 2 | Pools 4 to 7 | 211-426 | polymerase |
| 3 | Pools 12 and 13 | 592-700 | polymerase |
| 4 | Pools 14 to 17 | 703-912 | core |
| 5 | Pool 2 | 93-145 | polymerase |
| 6 | Pool 3 | 133-186 | polymerase |
| 7 | Pool 5 + additional N-terminal residues | 260-326 | polymerase |
| 8 | Pool 6 | 332-384 | polymerase |
| 9 | Pools 6/7 | 332-426 | polymerase |
| 10 | Pools 14/15 | 703-812 | core |
| 11 | Pools 15/16 | 749-871 | core |
| 12 | Pools 16/17 | 811-912 | core |
| 13 | Pool 17 | 859-912 | core |
| 14 | Pool 25 | 93-132 | polymerase |
| 15 | Pool 26 | 133-171 | polymerase |
| 16 | Pool 28 + additional N-terminal residues | 260-301 | polymerase |
| 17 | Pool 30 | 332-378 | polymerase |
| 18 | Pool 31 | 359-398 | polymerase |
| 19 | Pool 35 | 626-663 | polymerase |
| 20 | Pool 38 | 738-775 | core |

-continued

| SEQ ID NO: | Reference in Examples | Region of virtual HBV proteome sequence | HBV protein |
|---|---|---|---|
| 21 | Pool 39/40 | 778-837 | core |
| 22 | Pool 42 | 838-878 | core |
| 23 | Pool 43 | 859-891 | core |
| 24 | P113 | 96-130 | polymerase |
| 25 | P151 | 134-168 | polymerase |
| 26 | P277 | 260-295 | polymerase |
| 27 | P360 | 342-378 | polymerase |
| 28 | P376 | 359-398 (C to S substitution at 393) | polymerase |
| 29 | P645 | 627-662 | polymerase |
| 30 | P753 | 738-770 (S to T substitution at 743) | core |
| 31 | P797 | 780-814 (C to S substitution at 793) | core |
| 32 | P856 | 839-873 | core |
| 33 | P877 | 860-890 | core |
| 34 | P277(K) | 260-293 + KKK | polymerase |
| 35 | P645(K) | KKK + 627-662 | core |
| 36 | P753(K) | KK + 738-770 (S to Tat 743) + KKK | core |
| 37 | P797(K) | 780-814 (C to S at 792) + KKK | core |
| 38 | P856(K) | 839-873 + KKK | core |
| 40 | Pool 1 | 25-79 | polymerase |
| 41 | Pool 4 | 211-261 | polymerase |
| 42 | Pool 7 | 372-426 | polymerase |
| 43 | Pool 8 | 414-465 | polymerase |
| 44 | Pool 9 | 473-531 | polymerase |
| 45 | Pool 10 | 520-569 | polymerase |
| 46 | Pool 11 | 557-604 | polymerase |
| 47 | Pool 12 | 592-650 | polymerase |
| 48 | Pool 13 | 638-700 | polymerase |
| 49 | Pool 14 | 703-762 | core |
| 50 | Pool 15 | 749-812 | core |
| 51 | Pool 16 | 811-871 | core |
| 52 | Pool 18 | 966-1017 | X |
| 53 | Pool 19 | 1005-1062 | X |
| 54 | Pool 20 | 1171-1224 | surface |
| 55 | Pool 21 | 1241-1296 | surface |
| 56 | Pool 22 | 1312-1346 | surface |
| 57 | Pool 23 | 1392-1447 | surface |
| 58 | Pool 24 | 31-79 | polymerase |
| 59 | Pool 27 | 223-261 | polymerase |
| 60 | Pool 28 | 265-301 | polymerase |
| 61 | Pool 29 | 289-326 | polymerase |
| 62 | Pool 32 | 404 440 | polymerase |
| 63 | Pool 33 | 428-465 | polymerase |
| 64 | Pool 34 | 557-597 | polymerase |
| 65 | Pool 36 | 645-685 | polymerase |
| 66 | Pool 37 | 659-700 | polymerase |
| 67 | Pool 39 | 778-812 | core |
| 68 | Pool 40 | 811-837 | core |
| 69 | Pool 41 | 811-850 | core |
| 70 | Pool 44 | 979-1024 | X |
| 71 | Pool 45 | 1247-1289 | surface |
| 72 | Pool 46 | 1399-1439 | surface |
| 220 | Pool 5 | 265-326 | polymerase |
| 221 | P1266 | 1252-1284 (K to R at 1266) | surface |
| 222 | P1266 | (K) KKK + 1252-1284 (K to R at 1266) + KKK | surface |

SEQ ID NO: 39 is a virtual HBV protein sequence built by linear coassembly of the terminal domain of polymerase (positions 1 to 181), the reverse transcriptase domain of polymerase (position 182 to 549) the RNase domain H of polymerase (position 550 to 702), the core protein (position 703 to 914), the X protein (position 915 to 1068) and the surface protein (positions 1069 to 1468). The proteome sequence was obtained from consensus of consensus sequences generated from genotype A, B, C and D consensus sequences. SEQ ID NOs: 73 to 219 are the amino acid sequences of short peptides within each of pools 1 to 46. SEQ ID NO: 220 is the amino acid sequence of pool 5.

DETAILED DESCRIPTION OF THE INVENTION

Peptide Composition

The present invention provides a composition comprising broadly immunogenic peptide sequences capable of eliciting multiepitopic CD4+ and CD8+ T-cell immune responses with broad applicability in terms of population coverage and HBV genotype coverage. The present invention provides a pharmaceutical composition comprising at least one peptide from 15 to 60 amino acids in length, wherein said peptide comprises a fragment of at least 15 contiguous amino acids of the terminal domain of HBV polymerase, reverse transcriptase domain of HBV polymerase, RNase H domain sequence of HBV polymerase or HBV core protein. The peptide is of from 15 to 60 amino acids in length and is selected from peptides comprising a sequence of at least 15 contiguous amino acids of one of the sequences shown in SEQ ID NOs: 1 to 4. The peptide comprises at least one CD8+ T-cell epitope and/or at least one CD4+ T-cell epitope. The peptide elicits a response in peripheral blood mononuclear cells (PBMC) from at least one chronically infected HBV individual in an in vitro assay.

The composition may comprise multiple peptides having the properties defined above. The composition may be capable of eliciting an immune response in peripheral blood mononuclear cells (PBMC) from at least two individuals of different ethnicities and/or from two individuals infected with different HBV genotypes.

Peptide Sequences

The composition of the invention may comprise one or more peptides comprising at least 15 contiguous amino acids, such as at least 20, 25, 29, 30, 31, 32, 33, 34 or 35 amino acids from one of SEQ ID NOs: 1 to 4. SEQ ID NOs: 1, 2 and 3 are HBV polymerase sequences. SEQ ID NO: 4 is an HBV core protein sequence.

These regions may be further subdivided so that a peptide present in the composition of the invention may comprise at least 15, 20, 25, 30, 32, 33, 34 or 35 amino acids from one of SEQ ID NOs: 5 to 13. Preferably, peptides from within these subregions contain sequences within one of SEQ ID NOs: 14 to 23.

Exemplary short peptides within SEQ ID NOs: 1 to 4 are shown in SEQ ID NOs: 80 to 117 and 142 to 184. Preferred exemplary short peptides are shown in SEQ ID NOs: 80 to 83, 86 to 89, 98 to 101, 105 to 112, 146 to 150, 163 to 166 and 169 to 181. A composition of the invention may comprise a peptide comprising one or more of these short sequences.

Particularly preferred peptides from these HBV polymerase sequences comprise one of the sequences shown in SEQ ID NOs: 24 to 29. SEQ ID NO: 24 is a preferred region of SEQ ID NOs: 1, 5 and 14. SEQ ID NO: 25 is a preferred region of SEQ ID NOs: 1, 6 and 15. SEQ ID NO: 26 is a preferred region of SEQ ID NOs: 2, 7 and 16. SEQ ID NOs: 27 is a preferred region of SEQ ID NOs: 2, 8 and 17. SEQ ID NO: 28 is a preferred region of SEQ ID NOs: 2, 9 and 18. SEQ ID NO: 29 is a preferred region of SEQ ID NOs: 3 and 19.

Particularly preferred peptides from the above HBV core protein sequence (SEQ ID NO: 4) comprise one of the sequences shown in SEQ ID NOs: 30 to 33. SEQ ID NO: 30 is a preferred region of SEQ ID NOs: 10 and 20. SEQ ID NO: 31 is a preferred region of SEQ ID NOs: 11 and 21. SEQ ID NO: 32 is a preferred region of SEQ ID Nos: 12 and 22. SEQ ID NO: 33 is a preferred region of SEQ ID NOs: 13 and 23.

Other preferred peptides are comprised within the sequences shown in SEQ ID NOs: 24 to 33 and include peptides comprising at least 20, such as 25, 29, 30, 31, 32, 33 or 34 contiguous amino acids from within one of these sequences.

The composition may further comprise at least one peptide of from 15 to 60 amino acids in length, wherein said peptide comprises a fragment of at least 15 contiguous amino acids of HBV surface protein. The HBV surface protein peptide is typically of from 15 to 60 amino acids in length and is selected from peptides comprising a sequence of at least 15 contiguous amino acids of the sequence shown in SEQ ID NO: 55.

The HBV surface protein peptide may comprise at least 15, 20, 25, 30, 32, 33, 34 or 35 amino acids from one of SEQ ID NOs: 55, and preferably from SEQ ID NO: 71.

Exemplary short peptides within SEQ ID NOs: 55 and 71 are shown in SEQ ID NOs: 204 to 210 and 205 to 209, respectively. A composition of the invention may comprise a peptide comprising one or more of these short sequences.

Particularly preferred peptides from these HBV surface protein sequences comprise one of the sequences shown in SEQ ID NOs: 221. SEQ ID NO: 221 is a preferred region of SEQ ID NOs: 55 and 71.

Still further peptides that may be included in compositions of the invention are peptides that comprise a sequence that comprises one or more, such as two, three or four, amino acid substitutions, additions or deletions, preferably substitutions, within one of the sequences shown in one of SEQ ID NOs: 1 to 33, 55, 71 and 221. One, two, three or more amino acids within the contiguous sequence may be substituted. Substitutions within the specified sequences include mutations to remove cysteine residues. For example, cysteine residues may be substituted by serine residues.

Typically such peptides will have a sequence identity of at least 80%, such as at least 85%, 90%, 95% or 98% to at least 15 or 20, such as 25, 29, 30, 31, 32, 33, 34, 35, 36, 37, 38, 39 or 40, contiguous amino acids within one of SEQ ID NOs: 1 to 33, 55, 71 and 221, or to the entire length of one of the sequences shown in SEQ ID NOs: 24 to 33 and 221 (for example, as determined using the BLAST program available at the National Center for Biotechnology Information (blast.ncbi.nlm.nih.gov/Blast.cgi)). Such peptides include sequences that match the amino acid sequence of HBV genotype A, B, C, D, E or F in the equivalent region of the HBV polymerase or core protein.

The peptides may comprise additional sequences, provided that their overall length does not exceed 60 amino acids. For example, the peptide may comprise at least 20, such as 25, 29, 30, 31, 32, 33, 34 or 35 contiguous amino acids from within one of the sequences shown in one of SEQ ID NOs: 1 to 33, 55, 71 and 221, preferably SEQ ID NOs: 24 to 33 and 221 and may have a length of from 15, 20 or 25 amino acids up to 30, 31, 32, 33, 34, 35, 36, 37, 38, 39, 40, 45, 50, 55 or 60 amino acids.

Thus, the peptide typically has a length of from 15 or 20 to 60 amino acids, such as from 25 to 50 amino acids, preferably from 30 to 40 amino acids, for example, 31, 32, 33, 34, 35, 36, 37, 38 or 39 amino acids.

The peptide may include additional sequences. The additional sequences may facilitate manufacture or formulation of the peptide or enhance stability of the peptide. For example, the peptide may comprise one or more additional amino acids, typically at the N-terminus and/or the C-terminus to enhance the net positive charge of the peptide and/or to reduce the hydrophobicity of the peptide. The net positive charge may be increased so that the peptide has an isoelectric point greater than or equal to 7.

In one aspect of the invention, one or more, such as two or three positively charged amino acids (arginine and/or lysine) are added to the N- and/or C-terminus of one or more of the peptides in the composition. For example, three lysine residues may be added to the N- and/or C-terminus of one or more of the peptides. Positive amino acids are typically added at the end(s) of peptides that have an overall hydrophobicity of more than 65%, a net charge of less than zero and/or include cluster of hydrophobic amino acids.

Particular examples of peptides that include N- and/or C-terminal lysine residues are shown in SEQ ID NOs: 34 to 38 and 222.

The peptide may comprise one or more epitope that is not present in a consensus HBV sequence. One such example is the use of fusion peptides where a promiscuous T helper epitope is covalently linked (optionally via a polypeptide linker or spacer) to the consensus sequence. As an example, the promiscuous T helper epitope can be the PADRE peptide, tetanus toxoid peptide (830-843) or influenza haemagglutinin, HA(307-319).

Where the peptide is linked to a fluorocarbon, the terminus of the peptide, such as the terminus that is not conjugated to the fluorocarbon, or other attachment, can be altered, for example to promote solubility of the fluorocarbon-peptide construct via the formation of micelles. To facilitate large-scale synthesis of the construct, the N- or C-terminal amino acid residues of the peptide can be modified. When the desired peptide is particularly sensitive to cleavage by peptidases, the normal peptide bond can be replaced by a non-cleavable peptide mimetic. Such bonds and methods of synthesis are well known in the art.

The peptide may be a native peptide. The peptide may be modified to increase longevity, such as half-life or persistence at the site of administration, of the peptide in vivo or to direct the peptide to antigen-presenting cells. For example, the immunogenic peptide can contain one or more non-naturally occurring amino acids and/or non-naturally occurring covalent bonds for covalently connecting adjacent amino acids. In certain embodiments, the non-standard, non-naturally occurring amino acids can also be incorporated into the immunogenic peptides provided that they do not interfere with the ability of the peptide to interact with MHC molecules and remain cross-reactive with T-cells recognising the natural sequences. Non-natural amino acids can be used to improve peptide resistance to protease or chemical stability. Examples of non-natural amino acids include D-amino acids and cysteine modifications.

The peptide may be coupled to a carrier, such as a protein carrier or a delivery vector. Suitable delivery vectors include lipopeptides, for example fatty acyl chains such as a monopalmitoyl chain, virosomes, liposomes and cell penetrating peptides, such as penetrating and transactivator of transcription (TAT).

One or more, and preferably all, of the HBV peptides in the composition of the invention are preferably covalently linked to a fluorocarbon vector.

Combinations of Peptides

A composition of the invention may comprise multiple peptides. Accordingly, the composition may comprise at least two, such as at least three, four, five, six, seven, eight, nine, ten or more peptides, each comprising a sequence of at least 15 contiguous amino acids of one of SEQ ID NOs: 1 to 4 as described above. The composition may additionally comprise a peptide comprising a sequence of at least 15 contiguous amino acids of SEQ ID NO: 55 as described above.

In one aspect, the composition may comprise at least one peptide comprising at least 15 amino acids of one of the sequences shown in SEQ ID NOs: 1 to 3 and at least 15 amino acids of the sequence shown in SEQ ID NO: 4, and optionally at least one peptide comprising at least 15 amino acids of one of the sequences shown in SEQ ID NO: 55. For example, the composition may comprise at least one peptide comprising at least 15 amino acids of one of the sequences shown in SEQ ID NOs: 24, 25, 26, 27, 28, 29 and 34 and at least 15 amino acids of one of the sequences shown in SEQ ID NOs: 30 to 33 and 35 to 38.

In another aspect, the composition may comprise at least one peptide comprising a sequence of at least 15 contiguous amino acids of one of SEQ ID NOs: 1 and/or 2 as described above and at least one peptide comprising a sequence of at least 15 contiguous amino acids of SEQ ID NO: 3 or 4 as described above. For example, the composition may comprise a peptide comprising a sequence of at least 15 contiguous amino acids of SEQ ID NO: 1 or 2 (or peptides comprising sequences of both SEQ ID NOs: 5 and 6) as described above and a peptide comprising at least 15 contiguous amino acids of anyone of SEQ ID NOs: 10 to 13 as described above. The invention may comprise peptides comprising a sequence of at least 15 contiguous amino acids of any two, three, four, five or all of SEQ ID NOs: 5, 6, 7, 8 and 9 as described above and/or may comprise peptides comprising a sequence of at least 15 contiguous amino acids of any two, three or all of SEQ ID NOs: 10 to 13 as described above.

A peptide present in a composition of the invention may consist of, or consist essentially of, one of the sequences shown in SEQ ID NOs: 24 to 38. A HBV surface protein peptide present in a composition of the invention may consist of, or consist essentially of, one of the sequences shown in SEQ ID NOs: 221 and 222. The invention thus provides a pharmaceutical composition comprising at least one peptide, such as two or more peptides that consist of, consist essentially of or comprise the amino acid sequence shown in one of SEQ ID NOs: 24 to 38, and optionally at least one peptide that consists of, consists essentially of or comprises the amino acid sequence shown in SEQ ID NOs: 221 or 222. The composition may comprise at least two, such as three, four, five, six, seven, eight, nine or ten peptides comprising the sequences shown in SEQ ID NOs: 24 to 33 and 221. In one embodiment, one or more of the peptides comprising one of SEQ ID NOs: 24 to 33 and 221 may comprise N- or C-terminal lysine residues. More particularly the peptides comprising SEQ ID NOs: 26, 29, 30, 31, 32 and 221 may have the sequences shown in SEQ ID NOs: 34 to 38 and 222, respectively.

For example, the composition may comprise at least two, such as three, four, five, six, seven, eight, nine or ten of the peptides comprising, consisting of, or consisting essentially of the sequences shown in SEQ ID NOs: 24, 25, 27, 28, 33, 34, 35, 36, 37 and 38, or at least two, such as three, four, five, six, seven or eight of the peptides comprising, consisting of, or consisting essentially of SEQ ID NOs: 24, 25, 28, 33, 34, 36, 37 and 38. Any possible combination of these peptides may be present in a composition of the invention. Preferred combinations include one or more, such as any two, any three, any four or all, of SEQ ID NOs: 24, 25, 28, 33 and 31/37, preferably SEQ ID NO: 24 and/or 25. For example, a combination of SEQ ID NO: 24 and 33 results in a composition containing epitopes that bind to seven class I alleles and seven class II alleles. The composition may further comprise a peptide comprising, consisting of, or consisting essentially of SEQ ID NO: 221 or 222.

For example, the composition may comprise eight peptides comprising the following sequences: SEQ ID NOs: 24, 25, 26, 28, 30, 31, 32 and 33, and optionally a ninth peptide comprising SEQ ID NO: 222.

One of the peptides, such as the peptide comprising SEQ ID NO: 28, may be substituted by a peptide comprising SEQ ID NO: 27 and/or one peptide may be substituted by a peptide comprising SEQ ID NO: 29. One or more of the peptides may be substituted with a shorter peptide as described above, for example a peptide having at least 20 contiguous amino acids of the substituted peptide or with a peptide having at least 80% identity to the amino acid sequence of the substituted peptide across its entire length.

Preferably, the composition comprises at least one peptide from HBV polymerase as described above, more preferably from the terminal domain of HBV polymerase. In a particularly preferred embodiment, the HBV polymerase peptide comprises at least one amino acid sequence within SEQ ID NO: 1, such as at least one sequence within SEQ ID NO: 5, 6, 14, 15, 24 or 25. For example, such peptides may comprise the amino acid sequence shown in one of SEQ ID NOs: 80, 81, 82, 83, 86, 87, 88, 89, 24 or 25.

HBV Genotypes

The combination of peptide sequences in the composition provides epitopes, preferably both CD8+ and CD4+ epitopes, present in multiple HBV genotypes. HBV genotypes include genotypes A, B, C, D, E and F. For example, the long peptides may comprise epitopes from at least two HBV genotypes, such as A and D (the most highly prevalent genotypes in Europe) or B and C (the most highly prevalent genotypes in Asia). More preferably, the composition comprises epitopes from at least three HBV genotypes, such as for example, A, B and C, A, B and D, A, C and D or B, C and D. Most preferably, the composition comprises epitopes from at least HBV genotypes A, B, C and D. In addition to including any combination of epitopes from any combination of one or more of genotypes A, B, C and D, the composition may comprise epitopes to genotypes E, F and/or G. This may be determined by any suitable means, for example by using an in vitro PBMC assay as described herein.

Thus, the present invention provides a composition capable of eliciting an immune response in PBMC from two, three, four or all of: an individual infected with HBV genotype A, an individual infected with HBV genotype B, an individual infected with HBV genotype C, an individual infected with HBV genotype D and an individual infected with another HBV genotype.

A composition of the invention that is capable of eliciting an immune response in two, three or all of: an individual infected with HBV genotype A, an individual infected with HBV genotype B, an individual infected with HBV genotype C and an individual infected with HBV genotype D may comprise at least one peptide selected from at least two, preferably three or all of the following groups:

(i) a peptide comprising at least 15 contiguous amino acids of SEQ ID NO: 14, 15, 20, 21, 67, 22 or 23;

(ii) a peptide comprising at least 15 contiguous amino acids of SEQ ID NO: 14, 17, 18, 21 or 67;

(iii) a peptide comprising at least 15 contiguous amino acids of SEQ ID NO: 14, 16, 60, 19, 20 or 22; and (iv) a peptide comprising at least 15 contiguous amino acids of SEQ ID NO: 14, 15, 20, 21, 67, 22 or 23.

The composition may further comprise a peptide comprising at least 15 contiguous amino acids of SEQ ID NO: 55 or SEQ ID NO: 71.

For example, such a composition may comprise a peptide selected from at least two, preferably three or all of the following groups:

(i) a peptide comprising at least 15 contiguous amino acids of SEQ ID NO: 20, 21, 67, 22 or 23;

(ii) a peptide comprising at least 15 contiguous amino acids of SEQ ID NO: 17 or 18;

(iii) a peptide comprising at least 15 contiguous amino acids of SEQ ID NO: 16, 60 or 19; and (iv) a peptide comprising at least 15 contiguous amino acids of SEQ ID NO: 14 or 15.

The composition may further comprise a peptide comprising at least 15 contiguous amino acids of SEQ ID NO: 55 or SEQ ID NO: 71.

Suitable peptides comprising at least 15 amino acids of the specified sequences are described in more detail herein and include, in particular, the peptides of SEQ ID NOs: 24 to 38 mentioned in Table 4 and the peptides of SEQ ID NOs: 221 and 222.

In one aspect, the composition of the invention elicits an in vitro response in peripheral blood mononuclear cells (PBMC) from at least one individual chronically infected with HBV genotype A, one individual chronically infected with HBV genotype B, one individual chronically infected with HBV genotype C and one individual chronically infected with HBV genotype D. This may be determined by any suitable method, such as a method described in the Examples herein. The individuals may be of the same or different ethnicities, preferably from at least two different ethnicities. The individuals may be of the same or different HLA subtypes, preferably at least two different HLA subtypes.

Ethnicities

The invention provides a composition capable of eliciting an immune response in individuals of at least two, such as three or more different ethnicities. This can be assessed using an in vitro PBMC assay as described in the Examples. The composition of the invention may be capable of eliciting an immune response in PBMC from two, three or all of: an Oriental or Indian individual infected with HBV, a Caucasian individual infected with HBV and an African or Arabic individual infected with HBV.

A composition of the invention that is capable of eliciting an immune response in two, three or all of: an Oriental or Indian individual infected with HBV, a Caucasian individual infected with HBV and an African or Arabic individual infected with HBV may comprise at least one peptide selected from at least two, preferably three or all of the following groups:

(i) a peptide comprising at least 15 contiguous amino acids of SEQ ID NO: 14, 16, 60, 17, 18, 20, 21, 67 or 22;
(ii) a peptide comprising at least 15 contiguous amino acids of SEQ ID NO: 14, 15, 19, 20, 22 or 23; and
(iii) a peptide comprising at least 15 contiguous amino acids of SEQ ID NO: 14, 15, 20, 21, 67, 22 or 23.

The composition may further comprise a peptide comprising at least 15 contiguous amino acids of SEQ ID NO: 55 or SEQ ID NO: 71.

For example, such a composition may comprise a peptide selected from at least two, preferably three or all of the following groups:
(i) a peptide comprising at least 15 contiguous amino acids of SEQ ID NO: 16, 60, 17, 18;
(ii) a peptide comprising at least 15 contiguous amino acids of SEQ ID NO: 14, 15 or 19; and
(iii) a peptide comprising at least 15 contiguous amino acids of SEQ ID NO: 14, 15, 20, 21, 22 or 23.

The composition may further comprise a peptide comprising at least 15 contiguous amino acids of SEQ ID NO: 55 or SEQ ID NO: 71.

Suitable peptides comprising at least 15 amino acids of the specified sequences are described in more detail herein and include, in particular, the peptides of SEQ ID NOs: 24 to 38 mentioned in Table 4 and the peptides of SEQ ID NOs: 221 and 222.

Epitopes

HLA class I and class II molecules are polymorphic and their frequency varies between ethnic groups. Most of the polymorphism is located in the peptide-binding region, and as a result each variant is believed to bind a unique repertoire of peptide ligands. HLA polymorphism represents a major challenge for vaccine designers since HLA polymorphism is the basis for differential peptide binding. Moreover, specific HLA alleles are expressed at dramatically different frequencies in different ethnicities.

Despite such polymorphisms, HLA molecules bind overlapping set of peptides, and therefore, may be grouped accordingly into supertypes (Lund et al (2004) Immunogenetics 55(12):797-810, Sette et al (1999) Immunogenetics 50(3-4):201-212). A supertype is defined as a family of different HLA molecules having similar peptide binding repertoire and consequently sharing overlapping sets of peptides. In other words, a peptide that binds to an HLA allele belonging to a given supertype is likely to present a binding activity to the other supertype members.

Binding capacity of the peptides for different HLA class II alleles can be determined using a heterologous competitive assay using a specific biotinylated tracer peptide for each HLA class II allele as described in Texier et al (2000) J Immunol 164:3177-3184, Texier et al (2001) Eur J Immunol 31: 1837-1846 and Castelli et al (2002) J Immunol 169:6928-6934.

The following nine HLA class II alleles represent major supertypes or HLA clusters based on sequences analysis and binding-motif specificities as described in Lund et al (2004) Immunogenetics 55(12):797-810 and Greenbaum et al (2011) Immunogenetics 63(6):325-35: HLA-DR1 (α1*01:01; β1*01:01), HLA-DR3 (α1*01:01; β1*03:01), HLA-DR4 (α1*01:01; β1*04:01), HLA-DR7 (α1*01:01; β1*07:01), HLA-DR11 (α1*01:01; β1*11:01), HLA-DR13 (α1*01:01; β1*13:01), HLA-DR15 (α1*01:01; β1*15:01), HLA-DR51 (α1*01:01; β5*01:01) and HLA-DP4 (α1*01:03; β1*04:01). These alleles have a high prevalence across different ethnicities (see Wilson et al (2001) J Virol. 75(9): 4195¬4207).

A peptide present in a composition of the invention typically binds to at least two, preferably at least three, of the nine major HLA class II alleles, such as to at least two, preferably at least three, of the seven HLA class II alleles described in Example 10. One or more of the peptides present in the composition may bind to at least four, five, six, seven, eight or all of the nine major HLA class II alleles or to at least four, five, six or all of the seven HLA class II alleles described in Example 10. The composition of the invention preferably comprises peptides that can bind to at least seven, at least eight or all nine of the major HLA class II alleles described above, such as to all of the seven HLA class II alleles described in Example 10.

The number of HLA class I binding registers contained in each peptide may be determined by determining the ability of the peptide to bind to a range of frequently occurring HLA class I molecules. HLA class I binding may be measured using the ProImmune REVEAL® MHC-peptide Binding Assay (ProImmune Ltd, Oxford, UK). The REVEAL™ MHC peptide-binding assay measures the ability of each peptide to stabilize the ternary MHC-peptide complex for HLA-A*0101, HLA-A*0201, HLA¬A*0301, HLA-A*2402, HLA-B*0702, HLA-B*0801, HLA-B*3501 representative of main HLA class I supertypes. Each tested peptide is given a score relative to a pass/fail control peptide and also compared to a positive control peptide.

HLA class I molecules bind short peptides having length varying from 8 to 11 amino acids. In theory, 102 short peptides (27×8-mers, 26×9-mers, 25×10-mers & 24×11-mers) could be derived from a 35-mer peptide sequences. In order to limit the number of peptides to be tested, binding assays can be conducted using only nonamer peptides (the most frequent length for HLA class I binding peptides) with a good prediction score based on publically available algorithms.

The following HLA class I alleles are highly represented in human populations and (2) they belong to well-defined HLA supertypes (http://bioinformatics.nmdp.org/): HLA-A*0101, HLA-A*0201, HLA-A*0301, HLA-A*2402, HLA-B*0702, HLA¬B*0801, HLA-B*3501 and HLA-A*1101.

A peptide present in the composition of the invention typically comprises shorter peptides that bind to at least one, preferably at least two or at least three of these HLA class I alleles, such as to the first seven class I alleles listed above and preferably to the seven HLA class I alleles mentioned in Example 9. One or more of the peptides present in the composition may comprise shorter peptides that bind to at least four, five, six or all of the seven HLA class I alleles. The composition of the invention preferably comprises peptides that comprise shorter peptides that can bind to at least five, at least six or all seven of the HLA class I alleles described above.

A pharmaceutical composition of the invention typically comprises one or more peptides comprising one or more T-cell epitopes that bind to different MHC alleles to give broad population coverage. The composition may comprise peptides known or predicted to contain one or more MHC binding motif related to highly frequent MHC alleles in a specific ethnic group or across multiple ethnic groups. The composition may comprise one or more promiscuous CD4+ and CD8+ T-cell epitopes that bind to more than one allelic variant. The combination of peptide sequences in the composition provides T-cell epitopes that bind to different HLA subtypes.

In one aspect, the composition of the invention elicits a response in vitro in peripheral blood mononuclear cells (PBMC) from at least two individuals with different HLA subtypes. The composition may elicit an immune response in at least three, four, five, six or seven individuals each having a different HLA genotype, who may be Individuals of different ethnicities.

Fluorocarbon

The fluorocarbon can comprise one or more chains derived from perfluorocarbon or mixed fluorocarbon/hydrocarbon radicals, and may be saturated or unsaturated, each chain having from 3 to 30 carbon atoms. Thus, the chains in the fluorocarbon attachment are typically saturated or unsaturated, preferably saturated. The chains in the fluorocarbon attachment may be linear or branched, but preferably are linear. Each chain typically has from 3 to 30 carbon atoms, from 5 to 25 carbon atoms, or from 8 to 20 carbon atoms. In order to covalently link the fluorocarbon vector to the peptide, a reactive group, or ligand, for example —CO—, —NH—, S, 0 or any other suitable group is included in the vector. The use of such ligands for achieving covalent linkages is well known in the art. The reactive group may be located at any position on the fluorocarbon vector.

Coupling of the fluorocarbon vector to the peptide may be achieved through functional groups such as —OH, —SH, —COOH and —NH$_2$, naturally present or introduced onto any site of the peptide. Examples of such linkages include amide, hydrazone, disulphide, thioether and oxime bonds.

Optionally, a spacer element (peptidic or non-peptidic) can be incorporated to permit cleavage of the peptide from the fluorocarbon element for processing within an antigen-presenting cell and to optimize steric presentation of the peptide. The spacer can also be incorporated to assist in the synthesis of the molecule and to improve its stability and/or solubility. Examples of spacers include polyethylene glycol (PEG) or amino acids such as lysine or arginine that may be cleaved by proteolytic enzymes.

In one embodiment, the fluorocarbon-linked peptide can have the chemical structure $C_mF_n$—$C_yH_x$-(Sp)-R or derivatives thereof, where m=3 to 30, n≤2m+1, y=0 to 15, x≤2y, (m+y)=3 to 30 and Sp is an optional chemical spacer moiety and R is an immunogenic peptide. Typically m and n satisfy the relationship 2m−1≤n≤2m+1, and preferably n=2m+1. Typically x and y satisfy the relationship 2y−2≤x≤2y, and preferably x=2y. Preferably the $C_mF_n$—$C_yH_x$ moiety is linear.

It is preferred that m is from 5 to 15, more preferably from 8 to 12. It is also preferred that y is from 0 to 8, more preferably from 0 to 6 or 0 to 4. It is preferred that the $C_mF_n$—$C_yH_x$ moiety is saturated (i.e., n=2m+1 and x=2y) and linear, and that m=8 to 12 and y=0 to 6 or 0 to 4.

In a particular example, the fluorocarbon vector is derived from 2H, 2H, 3H, 3H-perfluoroundecanoic acid of the following formula:

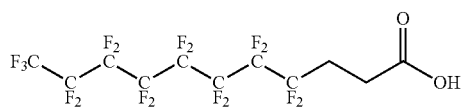

Thus, a preferred fluorocarbon attachment is the linear saturated moiety $C_8F_{17}(CH_2)_2$— which is derived from $C_8F_{17}(CH_2)_2COOH$.

Further examples of fluorocarbon attachments have the following formulae: $C_6F_{13}(CH_2)_2$—, $C_7F_{15}(CH_2)_2$—, $C_9F_{19}(CH_2)_2$—, $C_{10}F_{21}(CH_2)_2$—, $C_5F_{11}(CH_2)_3$—, $C_6F_{13}(CH_2)_3$—, $C_7F_{15}(CH_2)_3$—, $C_8F_{17}(CH_2)_3$— and $C_9F_{19}(CH_2)_3$— which are derived from $C_6F_{13}(CH_2)_2COOH$, $C_7F_{15}(CH_2)_2COOH$, $C_9F_{19}(CH_2)_2COOH$, $C_{10}F_{21}(CH_2)_2COOH$, $C_5F_{11}(CH_2)_3COOH$, $C_6F_{13}(CH_2)_3COOH$, $C_7F_{15}(CH_2)_3COOH$, $C_8F_{17}(CH_2)_3COOH$ and $C_9F_{19}(CH_2)_3COOH$ respectively. Preferred examples of suitable structures for the fluorocarbon vector-antigen constructs have the formula:

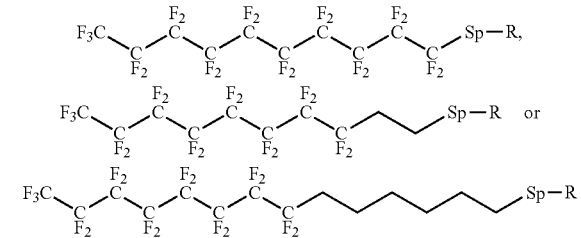

in which Sp and R are as defined above. In certain embodiments Sp is derived from a lysine residue and has the formula —CONH—$(CH_2)_4$—CH(NH$_2$)—CO—. Preferably R is any one of SEQ ID NOs: 1 to 14, preferably R is anyone of SEQ ID NOs: 1 to 6. The amino group of the N-terminal amino acid of each peptide, for example, SEQ ID NO: 1, 2, 3, 4, 5 or 6, forms an amide linkage with the C-terminal carboxy group of the spacer of formula —CONH—$(CH_2)_4$—CH(NH$_2$)—CO—.

In the context of the current invention, the fluorocarbon attachment may be modified such that the resulting compound is still capable of delivering the peptide to antigen presenting cells. Thus, for example, a number of the fluorine atoms may be replaced with other halogen atoms such as chlorine, bromine or iodine. In addition, it is possible to replace a number of the fluorine atoms with methyl groups and still retain the properties of the molecule described herein.

The peptides may be linked to the fluorocarbon vector via a spacer moiety. The spacer moiety is preferably a lysine residue. This spacer residue may be present in addition to any terminal lysine residues as described above, so that the peptide may, for example, have a total of four N-terminal lysine residues. Accordingly, the preferred formulation of the invention may comprise fluorocarbon-linked peptides in which the peptides have a C-terminal or N-terminal lysine residue, preferably an N-terminal lysine residue. The terminal lysine in the peptides is preferably linked to a fluorocarbon having the formula $C_8F_{17}(CH_2)_3COOH$. The fluorocarbon is preferably coupled to the epsilon chain of the N-terminal lysine residue.

It is contemplated that the pharmaceutical compositions described herein comprise at least 1, 2, 3, 4, 5, 6, 7, 8, 9 or 10 or more immunogenic peptides optionally each covalently linked to its own fluorocarbon vector.

Peptides

The present invention also provides a peptide that is useful in a composition of the invention. The peptide may be anyone of the peptides described above. In particular, the invention provides a peptide of up to 40, 50 or 60 amino acids in length comprising one of the sequences shown in SEQ ID NOs: 24 to 33 and 221 or a sequence that is at least 80% identical, such as at least 85%, 90%, 95% or 98% identical, to one of the sequences shown in SEQ ID NOs: 24 to 33 and 221. The peptide may include additional amino acids as described above. In one particular embodiment, the invention provides a peptide having the sequence shown in one of SEQ ID NOs: 34 to 38 and 222. Particularly preferred peptides of the invention comprise, consist essentially of, or consist of the sequences shown in SEQ ID NOs: 24, 25, 28, 30, 31, 32, 33, 34, 36, 37 and 38.

The invention also provides highly conserved immunogenic peptides from the terminal domain of HBV polymerase. These peptides may be any of the HBV polymerase peptides described above with reference to the compositions of the invention. Such peptides are typically from 15 to 60 amino acids in length comprise at least 15 contiguous amino acids of SEQ ID NO: 1 or 2 and elicit an immune response in vitro in PBMC from at least one individual chronically infected with HBV.

The peptide may be coupled to a carrier as described above. In one preferred aspect, the peptide of the invention is covalently linked to a fluorocarbon vector. The fluorocarbon vector may be as described above.

Other Components

The composition of the invention may comprise an additional immunogen. The immunogen may be a B-cell antigen. The B-cell antigen can serve to stimulate an antibody response to HBV. A pharmaceutical composition of the invention can, for example, comprise one or more fluorocarbon-linked peptides, which can stimulate a T-cell response, and a B-cell antigen.

Suitable immunogens that act as B-cell antigens include protein antigens such as hepatitis B surface antigen (HBsAg) or hepatitis B core antigen (HBcAg or HBeAg)

In one aspect, the present invention provides a composition comprising two or more peptides, such as fluorocarbon-linked peptides, further comprising an adjuvant and/or optionally a pharmaceutically acceptable carrier or excipient. The excipient may be a stabilizer or bulking agent necessary for efficient lyophilisation. Examples include sorbitol, mannitol, polyvinylpyrrolidone and mixtures thereof, preferably mannitol. Other excipients that may be present include preservatives such as antioxidants, lubricants, cryopreservatives and binders well known in the art.

An adjuvant is an agent that is able to modulate the immune response directed to a co-administered antigen while having few if any direct effects when given on its own. Such adjuvants may be capable of potentiating the immune response in terms of magnitude and/or cytokine profile. Examples of adjuvants include: natural or synthetically derived refinements of natural components of bacteria such as Freund's adjuvant & its derivatives, muramyldipeptide (MDP) derivatives, CpG, monophosphoryllipid A; other known adjuvant or potentiating agents such as saponins, aluminium salts and cytokines; oil in water adjuvants, water-in-oil adjuvants, immunostimulating complex (ISCOMs), liposomes, formulated nano and microparticles; bacterial toxins and toxoids; inulin, particularly gamma inulin; and TLR agonists.

Preferably, the adjuvant may be selected from the group consisting of: Peptidoglycan (such as TDM, MDP, muramyl dipeptide, Murabutide); alum solution (such as aluminium hydroxide, ADJUMER™ (polyphosphazene) or aluminium phosphate gel); glucans; algammulin; surfactants (such as squalane, Tween 80, Pluronic or squalene); calcium phosphate gel; bacterial toxins or toxoids (such as cholera holotoxin, cholera-toxin-Al-protein-A-D-fragment fusion protein, sub-unit B of the cholera toxin, or block copolymers); cytokine-containing liposomes; water-in-oil adjuvants (such as Freund's complete adjuvant, Freund's incomplete adjuvant or Montanide such as ISA 51 or ISA 720); oil-in-water adjuvants (such as MF-59); inulin-based adjuvants; cytokines (such as interferon-gamma; interleukin-1beta; interleukin-2; interleukin-7 or interleukin-12); ISCOMs (such as iscomatrix); microspheres and microparticles of any composition; and Toll-like receptor agonists (such as CpG, ligands of human TLR 1-10, ligands of murine TLR 1-13, ISS-1018, IC31, Imidazoquinolines, Poly (I:C), Monophosphoryllipid A, Ribi529, cholera toxin, heat-labile toxin, Pam3Cys or Flagellin).

Preparation of Pharmaceutical Compositions

The pharmaceutical compositions of the invention can be prepared by solubilising at least one peptide, such as a fluorocarbon-linked peptide, in acetic acid or in other solvents as a first step in formulating a pharmaceutical product. Examples of other solvents that may be used to disperse one or more of the fluorocarbon-linked peptides in the blend include phosphate buffered saline (PBS), propan-2-01, tert-butanol, acetone and other organic solvents. Approaches for solubilising fluorocarbon vector-peptide conjugates are described in WO2012/090002.

The peptide or fluorocarbon-linked peptide used as a starting material is typically desiccated. Peptides and fluorocarbon-linked peptides that comprise peptides shorter than 20 amino acids and/or that have fewer than 50% hydrophobic residues can be solubilised in a solvent other than acetic acid. Acetic acid is typically used where the peptide has more than 20 amino acids and/or has more than 50% hydrophobic residues.

The concentration of fluorocarbon-linked peptide in the solution typically is from about 0.1 mM to about 10 mM, such as about 0.5 mM, 1 mM, 2 mM, 2.5 mM or 5 mM. An example of a suitable concentration is about 10 mg/mL.

The input components may be blended homogenously together to the desired ratios with any aggregates dispersed, rendered sterile and presented in a suitable format for administration. Such examples could include the introduction of a vortexing and/or sonication post-blending or post-dilution stage to facilitate solubilisation. Other permutations of the manufacturing process flow could include sterile filtration being performed at an earlier stage of the process or the omission of lyophilisation to permit a liquid final presentation.

Where the different peptides or fluorocarbon-linked peptides are solubilised separately, for example in different solvents or in different concentrations of acetic acid, the solubilised peptides or fluorocarbon-linked peptides are blended to create a mixture of peptides or fluorocarbon-linked peptides.

The optional adjuvant and/or one or more pharmaceutically acceptable excipients can also be added to the solubilised peptide/fluorocarbon-linked peptide or mixture of peptides/fluorocarbon-linked peptides. Typically, the solubilised fluorocarbon-linked peptides are mixed with the excipient and/or adjuvant.

After solubilisation and blending the solution of fluorocarbon-linked peptide(s) may be diluted. For example, the blend may be diluted in water.

The solution containing the peptides or fluorocarbon-linked peptides is preferably sterilised. Sterilisation is particularly preferred where the formulation is intended for systemic use. Any suitable means of sterilisation may be used, such as UV sterilisation or filter sterilisation. Preferably, filter sterilisation is used. Sterile filtration may include a 0.45 µm filter followed by a 0.22 µm sterilizing grade filter train.

Sterilisation may be carried out before or after addition of any excipients and/or adjuvants.

The composition of the invention may be in dried, such as lyophilized, form. The composition of the invention may be an aqueous solution, for example an aqueous solution formed by dissolving a lyophilisate or other dried formulation in an aqueous medium. The aqueous solution is typically pH neutral.

Drying the formulation facilitates long-term storage. Any suitable drying method may be used. Lyophilisation is preferred but other suitable drying methods may be used, such as vacuum drying, spray-drying, spray freeze-drying or fluid bed drying. The drying procedure can result in the formation of an amorphous cake within which the peptides or fluorocarbon-linked peptides are incorporated.

For long-term storage, the sterile composition may be lyophilized Lyophilisation can be achieved by freeze-drying. Freeze-drying typically includes freezing and then drying. For example, the fluorocarbon-linked peptide mixture may be frozen for 2 hours at −80° C. and freeze-dried in a freeze drying machine for 24 hours.

Pharmaceutically acceptable compositions of the invention may be solid compositions. The fluorocarbon-linked peptide composition may be obtained in a dry powder form. A cake resulting from lyophilisation can be milled into powder form. A solid composition according to the invention thus may take the form of free-flowing particles. The solid composition typically is provided as a powder in a sealed vial, ampoule or syringe. If for inhalation, the powder can be provided in a dry powder inhaler. The solid matrix can alternatively be provided as a patch. A powder may be compressed into tablet form.

The dried, for example, lyophilized, peptide or fluorocarbon-linked peptide composition may be reconstituted prior to administration. As used herein, the term "reconstitution" is understood to mean dissolution of the dried vaccine product prior to use. Following drying, such as lyophilisation, the immunogenic peptide, for example, the fluorocarbon-linked peptide product, preferably is reconstituted to form an isotonic, pH neutral, homogeneous suspension. The formulation is typically reconstituted in the aqueous phase, for example by adding Water for Injection, histidine buffer solution (such as 28 mM L-histidine buffer), sodium bicarbonate, Tris-HCl or phosphate buffered saline (PBS). The reconstituted formulation is typically dispensed into sterile containers, such as vials, syringes or any other suitable format for storage or administration.

The composition may be stored in a container, such as a sterile vial or syringe, prior to use.

Medical Uses

The invention provides the composition of the invention for use in the treatment of the human or animal body by therapy. In particular, the composition of the invention is provided for use in a method of treating or preventing HBV infection. The composition of the invention elicits an immune response that may also be useful in HBV prophylaxis. The composition of the invention is preferably for use as a therapeutic vaccine to treat individuals infected with HBV. The composition of the invention is particularly useful in the treatment of patients with persistent chronic HBV infection, but may also be used to treat immune tolerant patients or inactive chronic carriers.

The present invention provides a therapeutic vaccine as a disruptive technology for the treatment of chronic HBV (CHB). The compositions of the invention enhance antiviral T-cell responses leading to spontaneous immune control of HBV infection. This allows cessation of antiviral NUC therapy and could potentially also lead to serological cure of HBV infection. HBsAg decline is used as a predictor of long term improved clinical outcome. HBsAg levels can be linked to the number of HBV infected hepatocytes and are determined by transcriptional activity of intrahepatic cccDNA controlled by various cytokines. Treatment using a composition of the invention may lead to HBsAg loss or HBsAg seroconversion.

The peptides and compositions of the invention are particularly useful in treating NUC-treated CHB patients. The peptides also represent an affordable treatment for HBeAg-positive patients in developing countries who may not be able to afford long-term NUC treatment. Vaccination of NUC-treated, HBV-DNA suppressed, HBeAg-negative patients in particular with the peptide compositions of the invention facilitates and accelerates HBsAg clearance. HBeAg-positive patients may also be treated. The compositions of the invention may also be used to treat inactive carriers of HBV.

Hepatitis B virus (HBV) infection is a major cause of liver-related morbidity and mortality. The compositions of the invention are provided for use in the treatment of liver failure, end-stage liver disease and hepatocellular carcinoma.

The compositions of the invention are useful in the vaccination of patients with hepatitis delta (HDV), the most severe form of viral hepatitis, for whom no approved therapy is available and which only occurs as a co-infection in HBsAg-positive individuals.

The invention also provides the use of the pharmaceutical composition of the invention in the manufacture of a medicament for treating or preventing HBV infection, particularly CHB, for treating or preventing liver failure, end-stage liver disease or hepatocellular carcinoma, or for treating or preventing HDV.

Similarly, the invention provides a method of treating or preventing HBV infection in a subject in need thereof, said method comprising administering to said subject a prophylactic or therapeutic amount of a composition of the present invention.

The composition of the invention may be administered in combination with a second therapeutic or prophylactic agent. For example, the second agent may comprise a further immunogen (such as a globular antigen or a recombinant or naturally occurring antigen), to further stimulate an immune response, for example to stimulate a humoral immune response where the fluorocarbon-linked peptide stimulates a cellular immune response, to HBV. It is understood that the second agent can be a B-cell antigen. Suitable B-cell antigens include HBsAg, HBcAg and HBeAg.

In a preferred embodiment, the second agent is an agent known for use in an existing HBV therapeutic treatment. The existing HBV therapeutic agent may be an interferon, such as interferon-alpha, or NUC, such as entecavir and tenofovir. The HBV therapeutic treatment may be a treatment that blocks suppressive cell types. Agents useful in such blocking treatments include anti-PD1 blocking antibodies, anti-PD1L blocking antibodies, anti-LAG3 blocking antibodies, anti-TIM3 blocking antibodies, anti-CTLA4 blocking antibodies and cyclophosphamide.

Where a second therapeutic agent or prophylactic agent is used in conjunction with a composition of the invention, administration may be contemporaneous or separated by time. The composition of the invention may be administered before, together with or after the second therapeutic agent.

Compositions of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In a preferred embodiment, the compositions are administered intramuscularly.

The composition can be administered to a subject in an amount that is compatible with the dosage composition and that will be prophylactically and/or therapeutically effective. The administration of the composition of the invention may be for either "prophylactic" or "therapeutic" purpose. As used herein, the term "therapeutic" or "treatment" includes anyone or more of the following: the prevention of infection or reinfection; the reduction or elimination of symptoms; and the reduction or complete elimination of a pathogen. Treatment may be effected prophylactically (prior to infection) or therapeutically (following infection).

The choice of carrier, if required, is frequently a function of the route of delivery of the composition. Within this invention, compositions may be formulated for any suitable route and means of administration. Pharmaceutically acceptable carriers or diluents include those used in compositions suitable for oral, ocular, rectal, nasal, topical (including buccal and sublingual), vaginal or parenteral (including subcutaneous, intramuscular, intravenous, intradermal, transdermal) administration.

The composition may be administered in any suitable form, for example as a liquid, solid or aerosol. For example, oral formulations may take the form of emulsions, syrups or solutions or tablets or capsules, which may be enterically coated to protect the active component from degradation in the stomach. Nasal formulations may be sprays or solutions. Transdermal formulations can be adapted for their particular delivery system and may comprise patches. Formulations for injection may be solutions or suspensions in distilled water or another pharmaceutically acceptable solvent or suspending agent.

The appropriate dosage of the prophylactic or therapeutic vaccine to be administered to a patient will be determined in the clinic. However, as a guide, a suitable human dose, which may be dependent upon the preferred route of administration, may be from 1 to 1000 µg, such as about 100 µg, 200 µg or 500 µg. Multiple doses may be required to achieve an immunological or clinical effect, which, if required, will be typically administered between 2 to 12 weeks apart. Where boosting of the immune response over longer periods is required, repeat doses 1 month to 5 years apart may be applied.

The following Examples illustrate the invention.

Example 1: Assessment of Ex Vivo Immunogenicity of HBV-Derived Short Peptide Pools in Human PBMC Methods and Materials
Populations
HBV-Infected Subjects Ninety-nine subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria:

Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Healthy Control Subjects

Cryopreserved PBMC from 17 subjects were obtained from CTL Technologies. These subjects conformed to the following criteria: Good general health, Unvaccinated to HBV, HBV surface antigen-negative, HBV core antibody-negative, HIV-negative and HCV-negative Short-Term Culture of PBMC One vial of PBMC from each subject (containing $1 \times 10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1 \times 10^6$ cells/mL for a total of 11 days. Cells were stimulated with a peptide pool containing 144 overlapping HBV-derived short peptides (SEQ ID NOs: 73 to 210 and SEQ ID NOs: 214 to 219), ranging in length from 15-20 amino acids and in overlap from 10 to 13 amino acids, at a final concentration of 0.1 µg/peptide/mL On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ ELISpot assay or intracellular cytokine staining Human IFNγ ELISpot Assay Ninety-six well multiscreen PVDF filter plates (Millipore) were coated overnight at 4° C. with 1000 (1:80) of anti-human IFNγ capture mAb (R&D Systems). Plates were then blocked with PBS supplemented with 1% BSA and 5% sucrose for 2 h at 4° C. Cells were plated in triplicate wells at $5 \times 10^4$ PBMC/well. Final antigen concentrations used were: 22 HBV-derived short peptide pools (see below; note pool 22 could not be prepared as peptides with SEQ ID NOs: 212 and 213 could not be dispersed due to insolubility) and HIV-3 35-mer negative peptide control: 5 µg/peptide/mL; PHA positive control: 1 µg/mL. ELISpot plates were incubated for 18 h at 37° C., 5% $CO_2$ in a humidified environment. Plates were then washed and incubated with 100 µl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

TABLE 2

Identification of peptides in pools 1 to 23

| Pool | SEQ ID NOs. of short peptides in pool |
|---|---|
| 1 | 73, 74, 75, 76, 77, 78, 79 |
| 2 | 80, 81, 82, 83, 84, 85 |
| 3 | 86, 87, 88, 89, 90, 91 |
| 4 | 92, 93, 94, 95, 96, 97 |
| 5 | 98, 99, 100, 101, 102, 103, 104 |
| 6 | 105, 106, 107, 108, 109, 110 |
| 7 | 111, 112, 113, 114, 115, 116, 117 |

TABLE 2-continued

Identification of peptides in pools 1 to 23

| Pool | SEQ ID NOs. of short peptides in pool |
|---|---|
| 8 | 118, 119, 120, 121, 122, 123 |
| 9 | 124, 125, 126, 127, 128, 129, 130 |
| 10 | 131, 132, 133, 134, 135, 136 |
| 11 | 137, 138, 139, 140, 141 |
| 12 | 142, 143, 144, 145, 146, 147, 148 |
| 13 | 149, 150, 151, 152, 153, 154, 155, 156 |
| 14 | 157, 158, 159, 160, 161, 162, 163, 164 |
| 15 | 165, 166, 167, 168, 169, 170, 171 |
| 16 | 172, 173, 174, 175, 176, 177, 178 |
| 17 | 179, 180, 181, 182, 183, 184 |
| 18 | 185, 186, 187, 188, 189, 190 |
| 19 | 191, 192, 193, 194, 195, 196, 197 |
| 20 | 198, 199, 200, 201, 202, 203 |
| 21 | 204, 205, 206, 207, 208, 209, 210 |
| 22 | 211, 212, 213 |
| 23 | 214, 215, 216, 217, 218, 219 |

Intracellular cytokine staining assay Cells were plated in a 96 well round bottom plate at $5 \times 10^5$ PBMC/well with stimulation from HBV-derived peptide pools at final concentrations of 5 µg/peptide/mL. The plate was incubated at 37° C. in a 5% $CO_2$ incubator for 20 h. For the final 3 h of the assay, PMA/Ionomycin was added to respective wells and Golgi plug was added to all wells. The cells were harvested and washed with PBS+0.1% BSA (wash buffer) and stained with anti-CD3, anti-CD4 and anti-CD8 (BD Biosciences) for 30 minutes at 4° C. After another wash, the cells were fixed and permeabilised with 100 µL of BD Cytofix/Cytoperm solution for 20 minutes at 4° C., followed by two washes with 1×BD Perm/Wash solution. Finally, cells were stained with ant-IL-2-FITC, anti-IFNγ-PE and anti-TNFα PerCP-Cy5.5 (BD Biosciences) for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

The initial step in identifying regions of interest in the HBV proteome was the comparison of IFNγ ELISpot responses of PBMC from HBV-uninfected, unvaccinated healthy subjects with those from chronic HBV-infected HBeAg negative-inactive carrier subjects in sustained control phase of the disease and chronic HBV-infected HBeAg negative subjects under treatment. Following short-term culture with a library of overlapping short peptides (15-20 mers overlapping by 10-13 amino acids), representing approximately 70% of the HBV proteome, PBMC were restimulated overnight with pools of these short peptides representing specific regions of interest within the HBV polymerase, core, X and surface antigens respectively. IFNγ responses to these peptide pools were then assessed using a human IFNγ ELISpot assay.

Pools representing a number of antigenic regions were found to stimulate IFNγ responses which were specific to the chronic HBV subjects. Specifically, stimulation with pools representing terminal regions of the HBV polymerase (pool 2 & pool 3) and regions of the HBV core (pools 14-17) resulted in the greatest magnitude and population coverage of IFNγ responses in the HBV-infected subjects (FIG. 1). To a lesser extent, pools 4 to 9 and pools 11 to 13 also tend to promote HBV-specific T-cell responses.

Figure 2:
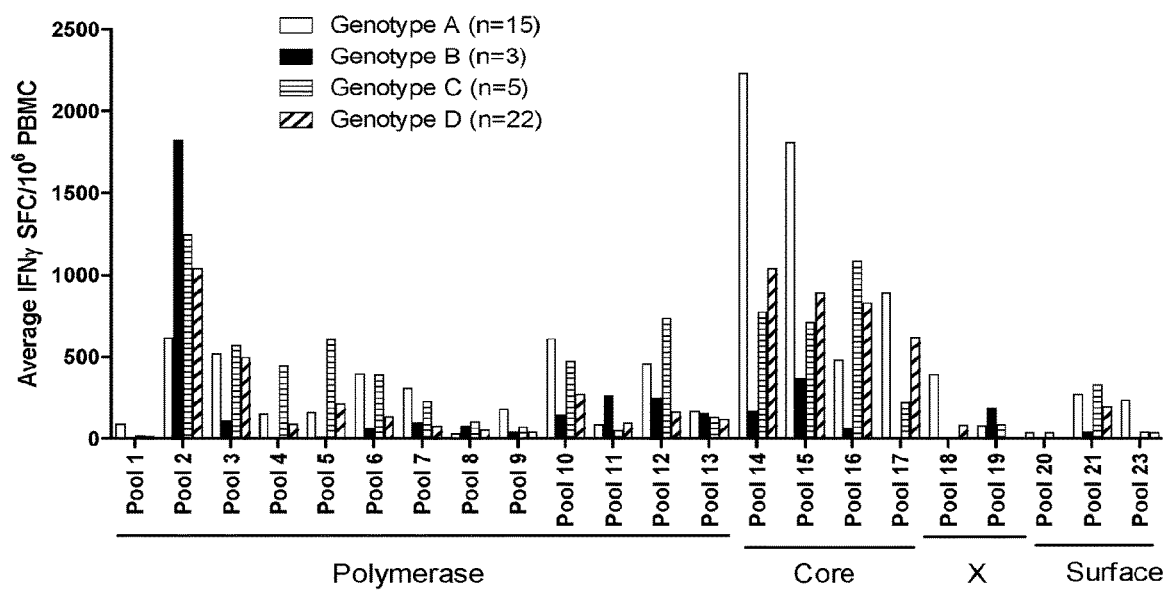
FIG. 2 shows the specificity of IFNγ responses to HBV-derived short peptide pools in HBV-infected subjects grouped by infecting HBV genotypes. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

In order to establish the role of the infecting HBV genotype on the nature of HBV-specific responses to short peptide pools, infecting HBV genotype was determined for each subject. This was determined by means of HBV surface antigen epitope assessment in plasma samples. IFNγ responses of PBMC from both immune control and treated HBV-infected subjects were subsequently grouped according to HBV genotypes A, B, C and D. Some subjects were not classified into these genotypes due to the sensitivity limitations of the assay and possible rare sera being assessed. These subjects were therefore not included in this assessment. Response profiles between the four genotypes showed similarities in that the regions showing the greatest magnitude of IFNγ responses were generally in the terminal polymerase and core regions of the HBV proteome (FIG. 2). Pools 2, 3, 10, 12, 14, 15, 16 and 17 appear to provide responses against multiple genotypes.

Figure 3:
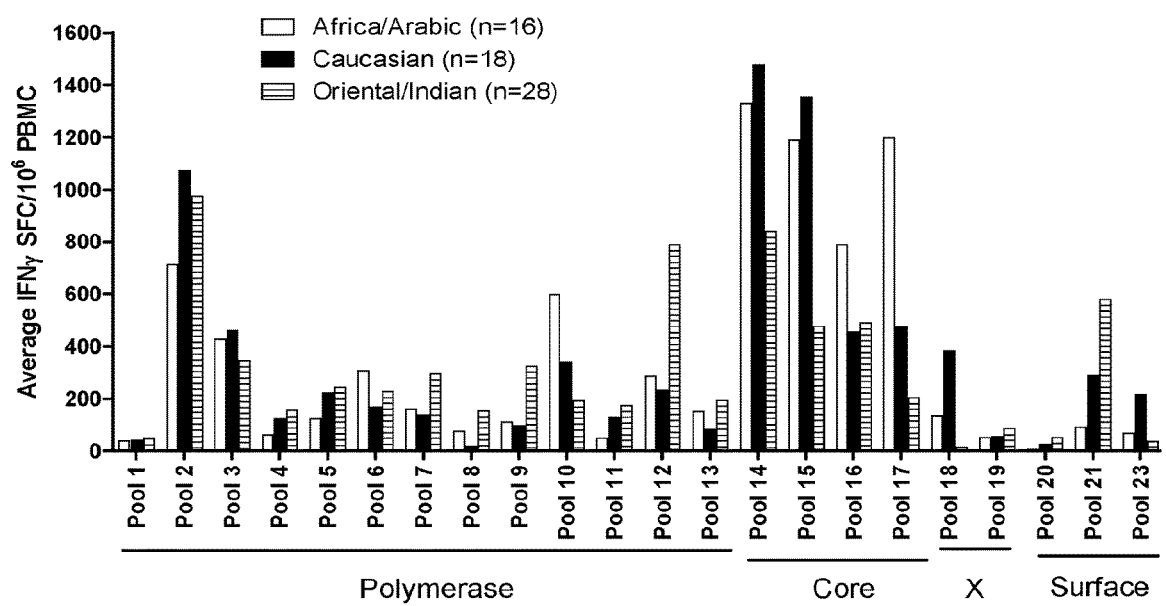
FIG. 3 shows IFNγ responses to HBV-derived short peptide pools in chronic HBV-infected subjects grouped by ethnic background. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

In order to establish the role of the genetic background of the host subject on the nature of HBV-specific responses to short peptide pools, subjects in the study were grouped according their ethnicity. IFNγ responses of PBMC from both immune control and treated HBV-infected subjects were subsequently compared in three broad ethnic groups, namely African/Arabic, Caucasian and Oriental/Indian. Responses profiles between the ethnic groups showed similarities again through the greatest magnitude of IFNγ response, with associated high population coverage, being found against pools from the terminal polymerase and core regions of the HBV proteome (FIG. 3). The Caucasian group appeared to differ slightly from the other two ethnic groups in that the average magnitude of responses to a number of pools were found to be highest in the treated group of subjects, when compared to those under immune control. Pools 2, 3, 10, 14, 15, 16, 17 and 21 tend to promote responses in multiple ethnic groups.

Figure 4:
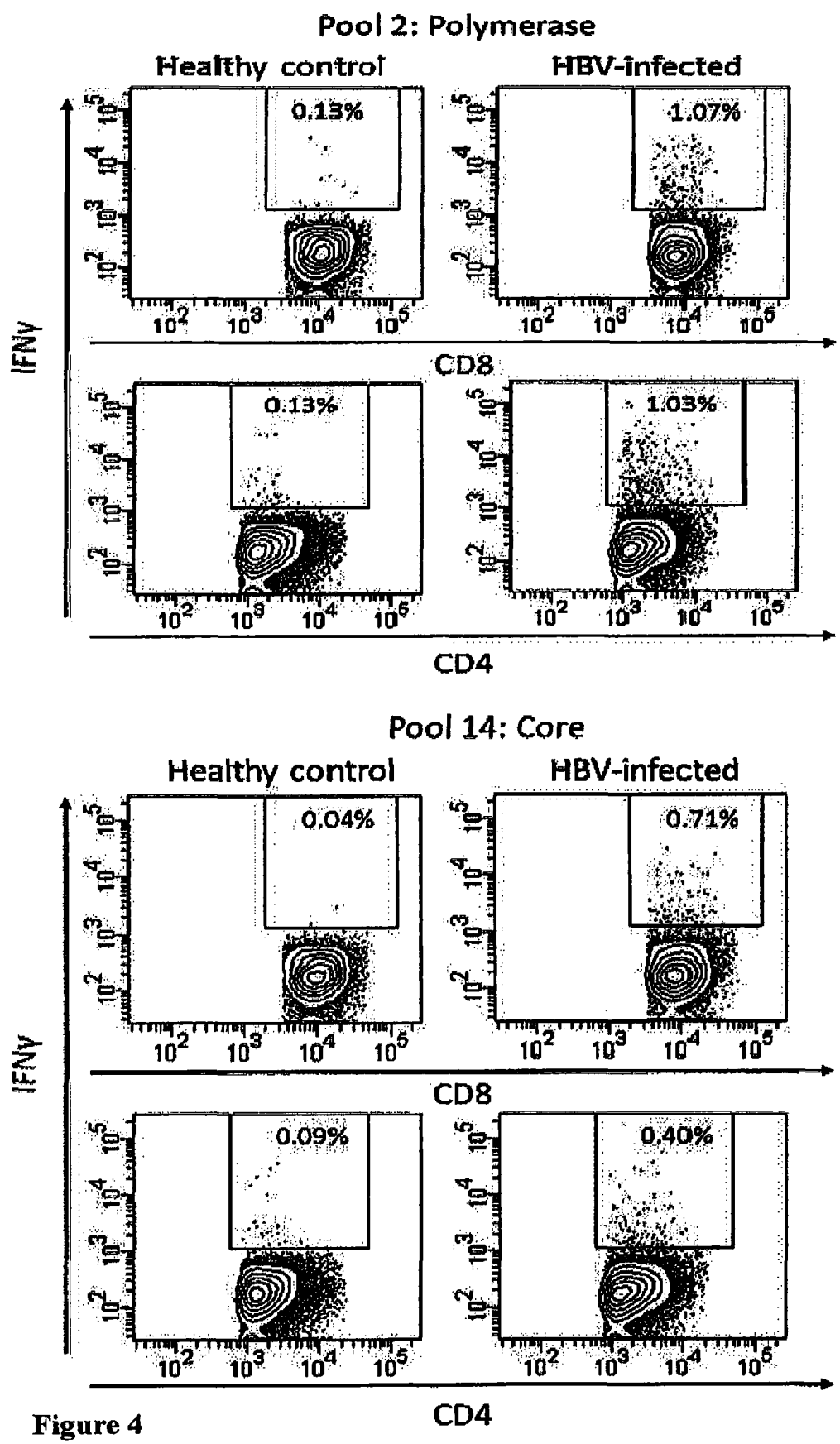
FIG. 4 shows representative dot plots of CD4 and CD8 T-cell IFNγ production in PBMC from chronic HBV and healthy control subjects following stimulation with HBV polymerase- and core-derived short peptide pools. PBMC from subjects were stimulated for 10 days with a short peptide pool library (0.1 μg/peptide/mL), followed by overnight stimulation (5 μg/peptide/mL) with HBV derived short peptide pool 2 or 14, representing regions of the HBV polymerase and core respectively. Results are expressed as IFNγ-producing cells, as a percentage of parent CD3/CD4 or CD3/CD8 T-cell populations. Stimulation in culture medium or PMA/ionomycin were used as negative and positive controls respectively and the gating strategy was based on negative control IFNγ production.

Finally, in order to further describe the type of IFNγ responses by PBMC to the short peptide pools, short-term cultured cells were restimulated overnight for intracellular cytokine staining Cells were then assessed for CD3, CD4, CD8 and IFNγ expression by flow cytometry. A comparison was made of IFNγ responses to the short peptide pools 2 and 14 in PBMC from healthy and chronic HBV-infected subjects (FIG. 4). These were two of the peptide pools which elicited the strongest HBV-specific responses in the IFNγ ELISpot assay. Consistent with the IFNγ ELISpot assay, increased IFNγ expression was found specifically in PBMC from chronic HBV-infected subjects. Moreover, this was found to be a dual CD4 and CD8 T-cell response.

Example 2: Assessment of Ex Vivo Immunogenicity of HBV-Derived Densigen-Associated Short Peptide Pools in Human PBMC Methods and Materials
Populations
HBV-Infected Subjects 104 subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria: Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Healthy Control Subjects

Cryopreserved PBMC from 17 subjects were obtained from CTL Technologies. These subjects conformed to the following criteria: Good general health, Unvaccinated to HBV, HBV surface antigen-negative, HBV core antibody-negative, HIV-negative and HCV-negative Short-Term Culture of PBMC One vial of PBMC from each subject (containing $1\times10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1\times10^6$ cells/mL for a total of 11 days. Cells were stimulated with a peptide pool containing 144 overlapping HBV-derived short peptides (SEQ ID NO: 73 to 210 and SEQ ID NO: 142 to 147), ranging in length from 15-20 amino acids and in overlap from 10 to 13 amino acids, at a final concentration of 0.1 µg/peptide/mL. On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ ELISpot assay or intracellular cytokine staining Human IFNγ ELISpot Assay 96 well multiscreen PVDF filter plates (Millipore) were coated overnight at 4° C. with 100 µl (1:80) of anti-human IFNγ capture mAb (R&D Systems). Plates were then blocked with PBS supplemented with 1% BSA and 5% sucrose for 2 h at 4° C. Cells were plated in triplicate wells at $5\times10^4$ PBMC/well. Final antigen concentrations used were: 23 HBV-derived Densigen-associated short peptide pools (see below): 5 µg/peptide/mL; CEF peptide pool positive control: 1 µg/peptide/mL; PHA positive control: 1 µg/mL. ELISpot plates were incubated for 18 h at 37° C., 5% CO2 in a humidified environment. Plates were then washed and incubated with 100 µl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

TABLE 3

Identification of peptides in pools 24 to 46

| Pool | SEQ ID NOs. of short peptides in pool |
|---|---|
| 24 | 74, 75, 76, 77, 78, 79 |
| 25 | 80, 81, 82, 83 |
| 26 | 86, 87, 88, 89 |
| 27 | 94, 95, 96, 97 |
| 28 | 98, 99, 100, 101 |
| 29 | 102, 103, 104 |
| 30 | 105, 106, 107, 108, 109 |
| 31 | 109, 110, 111, 112 |
| 32 | 116, 117, 118, 119 |
| 33 | 120, 121, 122, 123 |
| 34 | 137, 138, 139, 140, |
| 35 | 146, 147, 148, 149, 150 |
| 36 | 150, 151, 152, 153, 154 |
| 37 | 152, 153, 154, 155, 156 |
| 38 | 163, 164, 165, 166 |
| 39 | 169, 170, 171 |
| 40 | 172, 173 |
| 41 | 172, 173, 174, 175 |
| 42 | 176, 177, 178, 179 |
| 43 | 179, 180, 181 |
| 44 | 187, 188, 189, 190, 191 |
| 45 | 204, 205, 206, 207, 208, 209 |
| 46 | 215, 216, 217, 218 |

Intracellular Cytokine Staining (ICS) Assay

Cells were plated in a 96 well round bottom plate at $5\times10^5$ PBMC/well with stimulation from HBV-derived peptide pools at final concentrations of 5 µg/peptide/mL. The plate was incubated at 37° C. in a 5% $CO_2$ incubator for 20 h. For the final 3 h of the assay, PMA/Ionomycin was added to respective wells and Golgi plug was added to all wells. The cells were harvested and washed with PBS+0.1% BSA (wash buffer) and stained with anti-CD3, anti-CD4 and anti-CD8 (BD Biosciences) for 30 minutes at 4° C. After another wash, the cells were fixed and permeabilised with 100 µL of BD Cytofix/Cytoperm solution for 20 minutes at 4° C., followed by two washes with 1× BD Perm/Wash solution. Finally, cells were stained with ant-IL-2-FITC, anti-IFNγ-PE and anti-TNFα PerCP-Cy5.5 (BD Biosciences) for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

Subsequent to screening of responses to HBV-derived short peptide pools, 35-40 mer regions of interest were identified. These regions were further assessed with a view to using 35-40 mer peptides in a vaccine. Further assessment involved redesign of short peptide pools previously used for restimulation following short-term culture. Terminal short peptides extending beyond the 35-40 mer regions of interest were removed from pools in order to more accurately reflect the peptides that would be used in a vaccine. Following short-term culture with the peptide library, as before, these short peptide pools were then used for restimulation in human IFNγ ELISpot and ICS assays.

Figure 5:
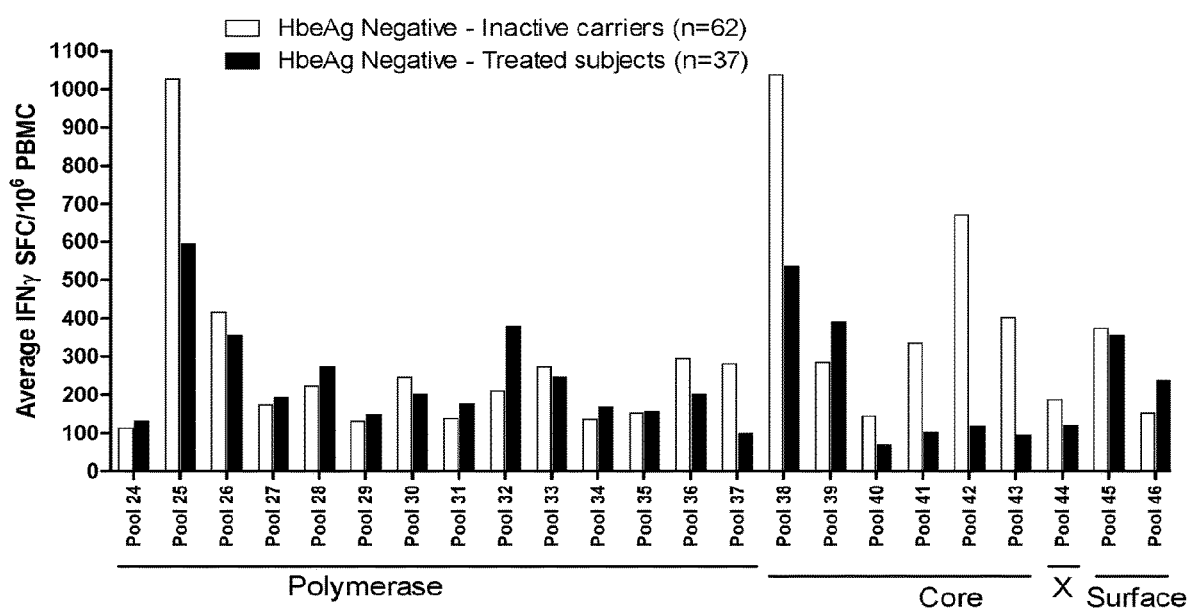
FIG. 5 is a comparison of IFNγ responses to HBV-derived short peptide pools representing 35-40 mer peptides in PBMC from healthy subjects and chronic HBV-infected HBeAg-negative subjects in immune control phase or undergoing active treatment. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 24 to 46 of the overlapping peptides, each representing 35-40 mer regions of the HBV proteome.

Restimulation with pools 24 to 46 indicated dominant HBV-specific T-cell responses to regions from terminal polymerase (pool 25 and pool 26) and core (pools 38 and 39 and pool 41 to 43) regions of the HBV proteome (FIG. 5).

An HBV-specific response was also found following stimulation with the surface region pool 45. Regions of polymerase corresponding to pool 28, pool 32, pool 33, pool 36 and pool 37 also gave a significant T-cell response.

Figure 6:
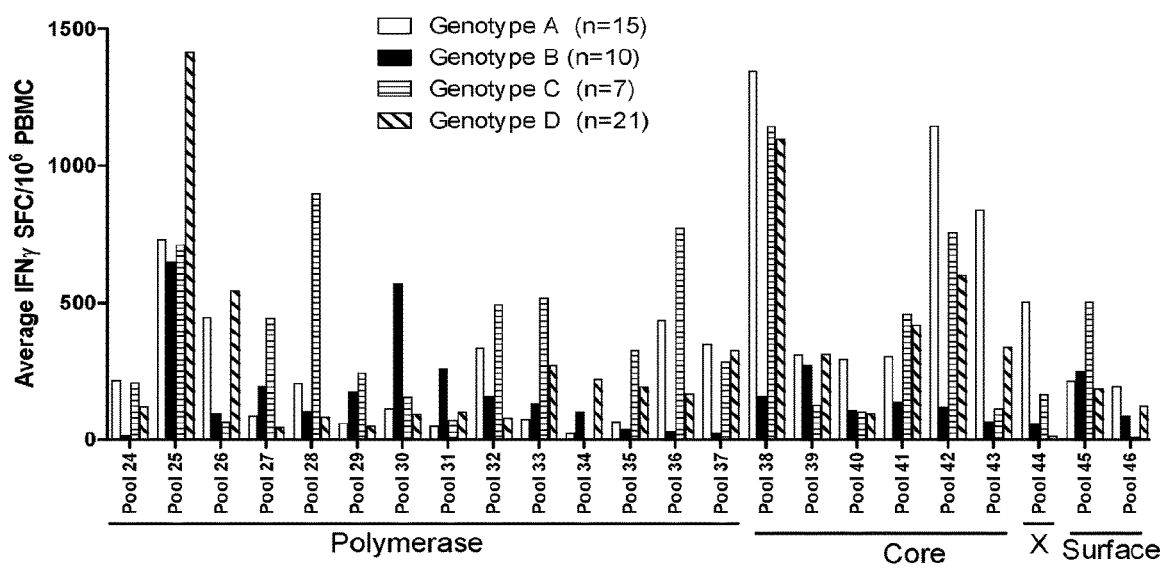
FIG. 6 shows the specificity of IFNγ responses to HBV-derived short peptide pools representing 35-40 mer peptides in HBV-infected subjects grouped by infecting HBV genotype. Following a 10 day culture with an HBV-derived overlapping short peptide pool library (0.1 μg/peptide/mL), PBMC were restimulated in an 18 h IFNγ ELISpot assay with one of pools 24 to 46 of the overlapping peptides, each representing specific regions of the HBV proteome.

IFNγ ELISpot responses to pools 24 to 46 were grouped according to infecting HBV genotype (FIG. 6). Pool 27, 28, 29, 32, 35, 36 each give a predominant responses against genotype C. Pools 25 and 26 give a predominant response against genotype D. Pools 30 and 31 give a predominant response against genotype B. Pools 38, 42, 43 and 44 give a predominant response against genotype A. Some pools tend to promote responses against more than one genotype: two genotypes for pools 26, 32, 33, 36 and 43, three genotypes for pools 37, 38, 41 and 42 or even four genotypes for pool 25.

Figure 7:
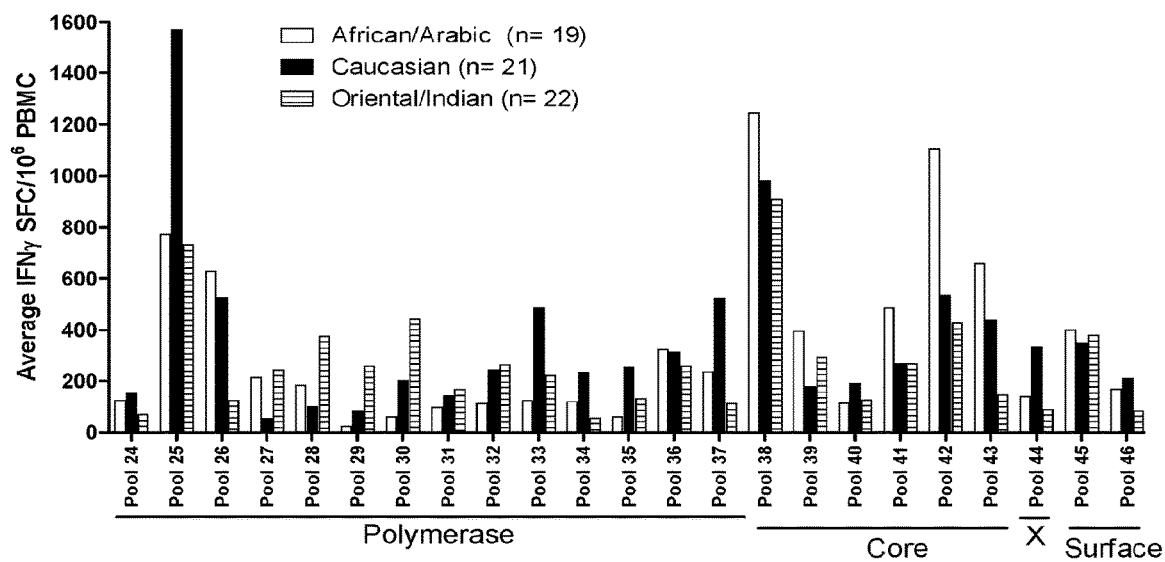
FIG. 7 shows IFNγ responses to HBV-derived short peptide pools representing 35-40 mer peptides in chronic HBeAg-negative HBV-infected subjects grouped by ethnic background. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 24 to 46 of the overlapping peptides, each representing 35-40 mer regions of the HBV proteome.

IFNγ ELISpot responses to pools 24 to 46 were grouped according to infecting HBV genotype (FIG. 7). Pools 28, 29 and 30 give a predominant response in Oriental/Indian ethnicities. Pools 25, 33, 34, 35 and 37 give a predominant responses in Caucasian. Pools 38, 39, 41, 42 and 43 give a predominant response in African/Arabic ethnicities. Some pools tend to promote responses in more than one ethnic group: two ethnic groups for each of pools 26, 39 and 43 or three ethnic groups for each of pools 25, 38 and 42. The results are summarised in Table 4 below.

TABLE 4

Summary of predominant responses of peptides from selected regions of the HBV proteome against different HBV genotypes (A, B, C and D) and in patients of different ethnicities (OI = Oriental/Indian, C = Caucasian, AA = African/Arabic). Where a region elicits an immune response against multiple HBV genotypes or multiple ethnicities, the predominant response is indicated in bold.

| HBV proteome region | Terminal domain of polymerase | | Reverse transcriptase domain of polymerase | | | RNaseH domain of polymerase | Core protein | | | |
|---|---|---|---|---|---|---|---|---|---|---|
| Pool No. | 25 | 26 | 28 | 30 | 31 | 35 | 38 | 39 | 42 | 43 |
| Peptide | P113 | P151 | P277 | P360 | P376 | P645 | P753 | P797 | P856 | P877 |
| SEQ ID | 14 | 15 | 16 | 17 | 18 | 19 | 20 | 21 | 22 | 23 |
|  | 24 | 25 | 60 | 27 | 28 | 29 | 30 | 67 | 32 | 33 |
|  |  |  | 26 |  |  | 35 | 36 | 31 | 38 |  |
|  |  |  | 34 |  |  |  |  | 37 |  |  |
| Genotype | A B C D | A D | C | B | B | C | A C D | A B D | A C D | A D |
| Ethnicity | OI C AA | C AA | OI | OI | OI | C | OI C AA | OI AA | OI C AA | C AA |

Figure 8:
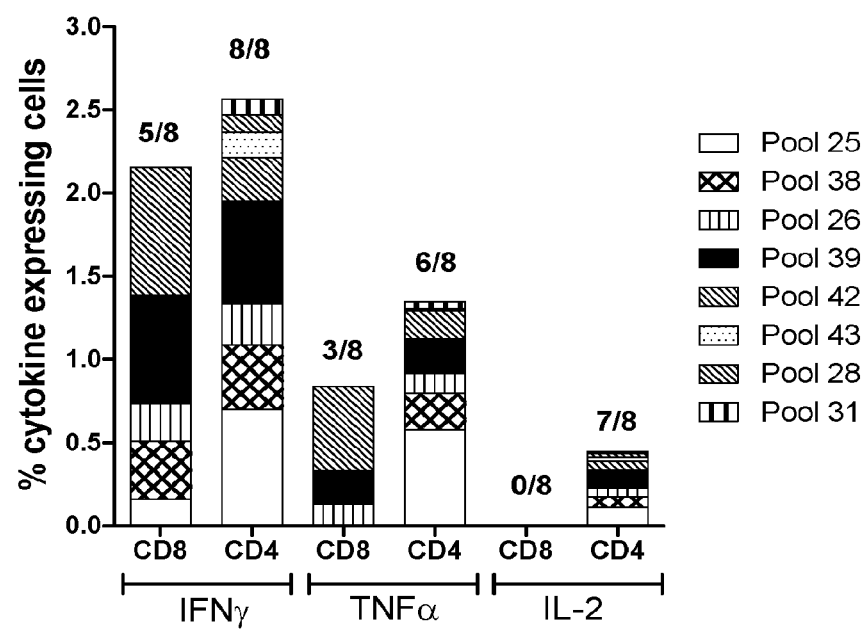
FIG. 8 is a summary of cytokine responses by PBMC from HBV-infected subjects to individual short peptide pools representing 35-40 mer peptides. Following a 10 day short-term culture with an HBV-derived short peptide pool library, PBMC from chronic HBeAg-negative HBV-infected subjects (n=7-14) were cultured overnight with one of HBV peptide pools 25, 38, 26, 39, 42, 43, 28 and 31 (representing peptides P113, P753, P151, P797, P856, P877, P277 and P376) at a final concentration of 5 μg/peptide/mL. Cells were stained for extracellular expression of CD3, CD4 and CD8, followed by intracellular expression of IFNγ, IL-2 and TNFα. Cells were assessed by flow cytometry. Cytokine expression was normalized to media negative controls for each subject. Data represents mean expression for each cytokine assessed. Breadth of responses are shown above each stacked bar.

Eight pools were selected for further analysis of T-cell responses by intracellular cytokine staining PBMC from between 7 and 14 subjects (depending on the number of cells available following the IFNγ ELISpot assay) were stimulated overnight with the one of the eight pools and cells were stained for surface CD3, CD4 and CD8 expression, together with intracellular IFNγ, TNFα and IL-2 expression (FIG. 8). IFNγ expression was found in both CD8 and CD4 T-cell populations, with a respective breadth of response to 5/8 and 8/8 of the peptide pools assessed. Similarly, TNFα expression was found in both CD8 and CD4 T-cells populations with a breadth of peptide pool response of 3/8 and 6/8 respectively. CD8 T-cells were found to express no IL-2 following peptide pool stimulation, yet CD4 T-cells expressed IL-2 following stimulation with 7 of the 8 pools.

Example 3: Construction of Fluorocarbon-Linked HBV Peptides

Peptides having the amino acid sequences shown in SEQ ID NOs: 24, 25, 28, 33, 34, 36, 37 and 38 and 222 were synthesised by FMOC (fluorenylmethyloxycarbonyl chloride) solid-phase synthesis. The fluorocarbon chain ($C_8F_{17}(CH_2)_2COOH$) was then incorporated on the epsilon-chain of an additional N-terminal lysine of each peptide to derive the fluorocarbon-linked peptide. Purified fluorocarbon-linked peptides or unmodified peptides were obtained through cleavage in the presence of trifluoroacetic acid (TFA) and a final purification by reverse phase-high performance liquid chromatography (RP-HPLC). All preparations had a purity of 90% or greater.

FA-P113:
(SEQ ID NO: 24)
K(FA)-VGPLTVNEKRRLKLIMPARFYPNVTKYLPLDKGIK-NH2;

FA-P151:
(SEQ ID NO: 25)
K(FA)-PEHVVNHYFQTRHYLHTLWKAGILYKRETTRSASF-NH2;

FA-P376:
(SEQ ID NO: 28)
K(FA)-KLHLYSHPIILGFRKIPMGVGLSPFLLAQFTSAISSVVRR-NH2;

FA-753(K):
(SEQ ID NO: 36)
K(FA)-KKKEFGATVELLSFLPSDFFPSVRDLLDTASALYRKKK-NH2;

-continued

FA-P856(K):
(SEQ ID NO: 38)
K(FA)-LTFGRETVLEYLVSFGVWIRTPPAYRPPNAPILSTKKK-NH2;

FA-P877:
(SEQ ID NO: 33)
K(FA)-PPAYRPPNAPILSTLPETTVVRRRGRSPRRR-NH2;

FA-P277(K):
(SEQ ID NO: 34)
K(FA)-RVSWPKFAVPNLQSLTNLLSSNLSWLSLDVSAAFYHKKK-NH2;

FA-P797(K):
(SEQ ID NO: 37)
K(FA)-SPHHTALRQAILSWGELMTLATWVGSNLEDPASRDKKK-NH2;

FA-P1266(K):
(SEQ ID NO: 222)
K(FA)-KKKGPLLVLQAGFFLLTRILTIPQSLDSW WTSLNFLKKK-NH2.

Example 4: Long HBV Peptide Formulation

A vaccine candidate, FP02.1, composed of the nine fluorocarbon-conjugated HBV-derived peptides prepared as described in Example 3 were formulated as described below. Conditions for peptide solubilization are described in Table 5. Briefly, each of the nine fluorocarbon-conjugated peptides was weighed in a 5 ml glass vial. Each peptide was then solubilised with 2 to 12% acetic acid in water solutions to achieve a peptide concentration of 10 mg. Peptide solutions (3.9 ml for each peptide) were blended in a 150 ml sterile container before 3.9 ml of 10% acetic acid solution in water was added. After stirring with a magnetic stirrer for 2 minutes, 39 mL of 9.0% mannitol in water solution was added. After stirring with a magnetic stirrer for a further 2 minutes, the solution was filtered using a 0.22 μm 33 mm Millex filter. 1.2 mL of the filtered solution was dispatched into autoclaved 2 ml glass vials. Filtration recovery measured by RP-HPLC was >95%. The vials were frozen at −80° C. for one hour. The samples were then freeze-dried for 36 hours. Freeze drying ventilation was performed under nitrogen and vial stoppering was carried out at a pressure between 400 and 600 mbar. The amount of peptide was 600 μg per peptide per vial; upon reconstitution with 1.2 mL, the final concentration was 500 μg/peptide/ml.

TABLE 5

Solubilisation conditions for preparation of FP02.1

| Peptide | Gross mass (mg) | Peptide content (%) | Net Mass (mg) | Targeted Concentration (mg/ml) | Acetic acid (%) | Volume added |
|---|---|---|---|---|---|---|
| FA-P113 | 46.54 | 86.8 | 40.40 | 20 | 2 | 4.040 |
| FA-P151 | 45.87 | 88.0 | 40.37 | 20 | 12 | 4.036 |
| FA-P277(K) | 49.76 | 81.8 | 40.70 | 20 | 4 | 4.170 |
| FA-P376 | 47.62 | 85.3 | 40.62 | 20 | 2 | 4.062 |
| FA-P797(K) | 44.69 | 92.0 | 41.11 | 20 | 2 | 4.112 |
| FA-P877 | 49.25 | 81.9 | 40.34 | 20 | 2 | 4.034 |
| FA-P753(K) | 47.47 | 85.1 | 40.40 | 20 | 2 | 4.040 |
| FA-P1266(K) | 45.82 | 86.4 | 40.45 | 20 | 2 | 4.046 |
| FA-P856(K) | 47.02 | 86.8 | 40.81 | 20 | 2 | 4.082 |

Example 5: Preferred HBV Peptides and Mixtures are Immunogenic in Chronic HBV Carriers Irrespective of the Disease Stage, the Genotype of the HBV Virus and 5 the Ethnicity of the Subjects Methods and Materials
Populations 40 subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria: Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Short-Term Culture of PBMC

One vial of PBMC from each subject (containing $1 \times 10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1 \times 10^6$ cells/mL for a total of 11 days. Cells were stimulated with a mixture of the nine HBV-derived long peptides described in Example 3.

Each peptide was used at a final concentration of 1 μg/peptide/mL. On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ (interferon-gamma) ELISpot assay or intracellular cytokine staining.

Human IFNγ ELISpot Assay 96 well multiscreen PVDF filter plates (Millipore) were coated overnight at 4° C. with 100 μl (1:80) of anti-human IFNγ capture mAb (R&D Systems). Plates were then blocked with PBS supplemented with 1% BSA and 5% sucrose for 2 h at 4° C. Cells from short term cultures were plated in triplicate wells at 5×104 PBMC/well. Final antigen concentrations used were: 5 μg/mL for each individual peptides; PHA positive control: 1 μg/mL. ELISpot plates were incubated for 18 h at 37° C., 5% $CO_2$ in a humidified environment. Plates were then washed and incubated with 100 μl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

Intracellular Cytokine Staining Assay (i) Cells from short-term culture were plated in a 96 well round bottom plate at 5×105 PBMC/well with stimulation from 9 HBV-derived long peptides (NP113, NP151, NP277 (K), NP376, NP753(K), NP797(K), NP856(K), NP877 and NP1266(K)) at final concentrations of 5 μg/mL. The plate was incubated at 37° C. in a 5% $CO_2$ incubator for 20 h. For the final 3 h of the assay, PMA/Ionomycin was added to respective wells and Golgi plug was added to all wells. The cells were harvested and washed with PBS+% BSA (wash buffer) and stained with anti-CD3, anti-CD4 and anti-CD8 (BD Biosciences) for 30 minutes at 4° C. After another wash, the cells were fixed and permeabilised with 100 μL of BD Cytofix/Cytoperm solution for 20 minutes at 4° C., followed by two washes with 1×BD Perm/Wash solution. Finally, cells were stained with ant-IL-2-FITC, anti-IFNγ-PE and anti-TNFα PerCP-Cy5.5 (BD Biosciences for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

Figure 9:
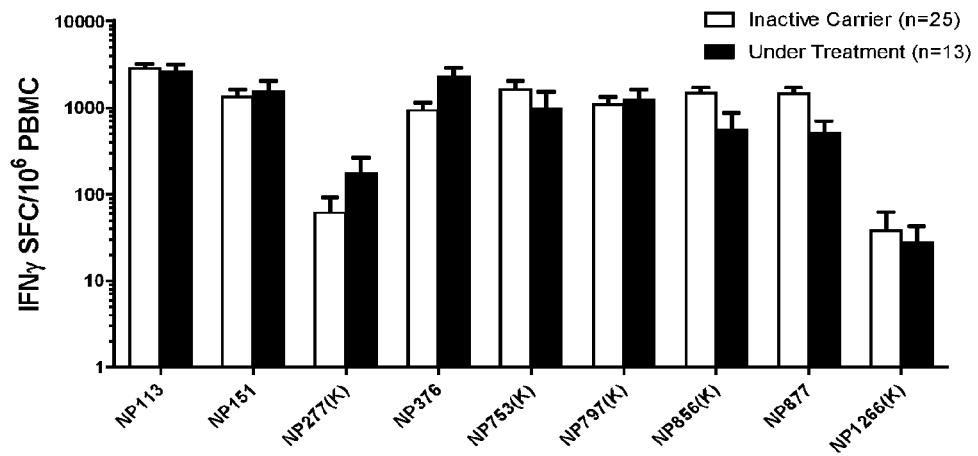
FIG. 9 shows the number of IFNγ spot forming cells (mean values) measured in PBMCs from chronic HBV-infected (either HBeAg-negative inactive carriers or HBeAg-negative treated subjects). Following a 10 day culture with the nine unconjugated HBV peptides (NP113, NP151, NP277(K), NP376, NP753(K), NP797(K), NP856 (K), NP877 and NP1266(K)) (0.1 μg/peptide/mL), PBMC were restimulated in an 18 h IFNγ ELISpot assay with individual peptides at a concentration of 511 g/ml.
Figure 10:
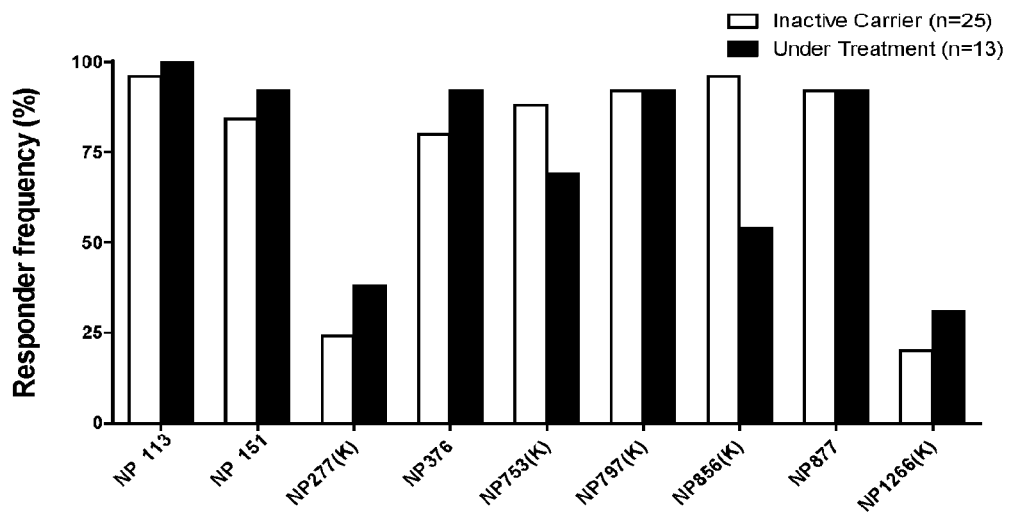
FIG. 10 shows the frequency of responders to the IFNγ ELISpot assay in response to HBV peptides measured in PBMCs from chronic HBV-infected (either HBeAg-negative inactive carriers or HBeAg-negative treated subjects). Following a 10 day culture with the nine unconjugated HBV peptides (NP113, NP151, NP277(K), NP376, NP753(K), NP797(K), NP856(K), NP877 and NP1266(K)) (0.1 μg/peptide/mL), PBMC were restimulated in an 18 h IFNγ ELISpot assay with individual peptides at a concentration of 5 μg/ml.
Figure 11:
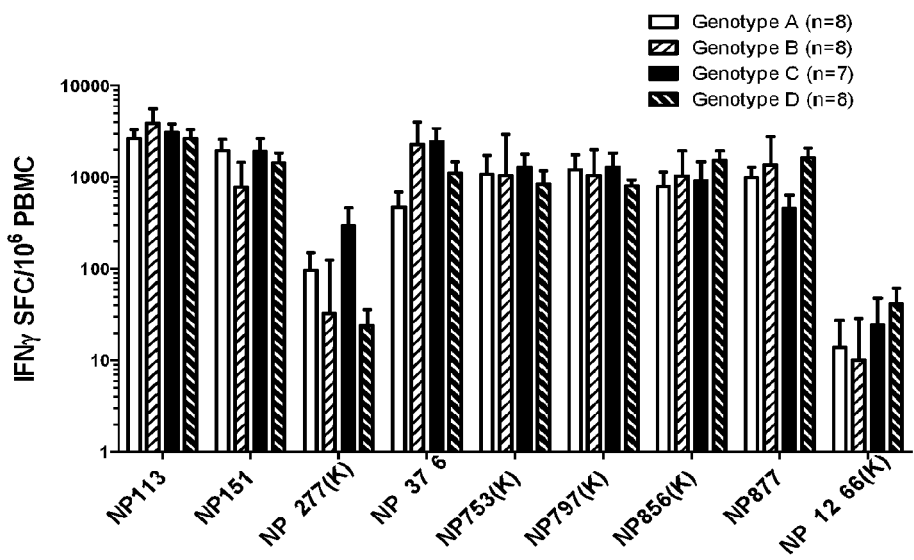
FIG. 11 shows the number of IFNγ spot forming cells (mean values) measured in PBMCs from chronic HBV-infected subjects grouped by infecting HBV genotypes. Following a 10 day culture with the nine unconjugated HBV peptides (NP113, NP151, NP277(K), NP376, NP753(K), NP797(K), NP856(K), NP877 and NP1266(K)) (0.1 μg/peptide/mL), PBMC were restimulated in an 18 h IFNγ ELISpot assay with individual peptides at a concentration of 5 μg/ml.

All peptide promoted detectable T cell responses in HBV carriers either HBeAg-negative inactive carriers and HBeAg-negative treated subjects (see FIGS. 9 and 10). Among the different peptides tested, NP113, NP151, NP376, NP753(K), NP797(K), NP856(K) and NP877 promote the highest level of responses in both patient populations and in the highest proportion of subjects. Surprisingly, the cumulative response to NP113 and NP151 is higher in both populations compared than any other combination of two peptides tested. Moreover, the cumulative response to NP113, NP151 and NP376 induces the highest level of response in both populations compared to any other combinations of three peptides tested. As shown in FIG. 11, all tested peptides promote cross-reactive T cell responses across all four HBV genotypes. Peptides NP113, NP151, NP376, NP753(K), NP797(K), NP856(K) and NP877 promote the highest responses across all four genotypes A, B, C & D compared to peptides NP2777(K) and NP1226(K). Surprisingly, NP113 promotes the highest T cell response across all four genotypes compared to all other peptides.

Figure 12:
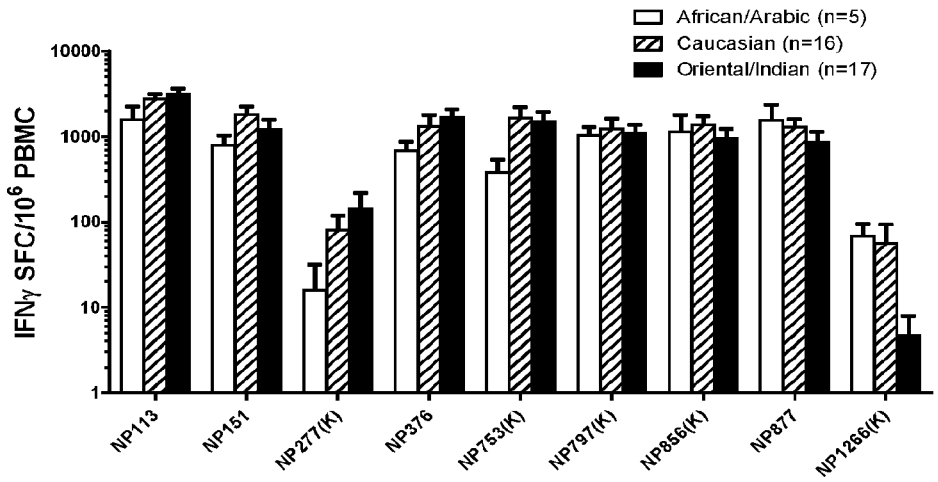
FIG. 12 shows the number of IFNγ spot forming cells measured (mean values) in PBMCs from chronic HBV-infected subjects grouped by ethnic background. Following a 10 day culture with the nine unconjugated HBV peptides (NP113, NP151, NP277(K), NP376, NP753(K), NP797(K), NP856(K), NP877 and NP1266(K)) (0.1 μg/peptide/mL), PBMC were restimulated in an 18 h IFNγ ELISpot assay with individual peptides at a concentration of 5 μg/ml.
Figure 13A:
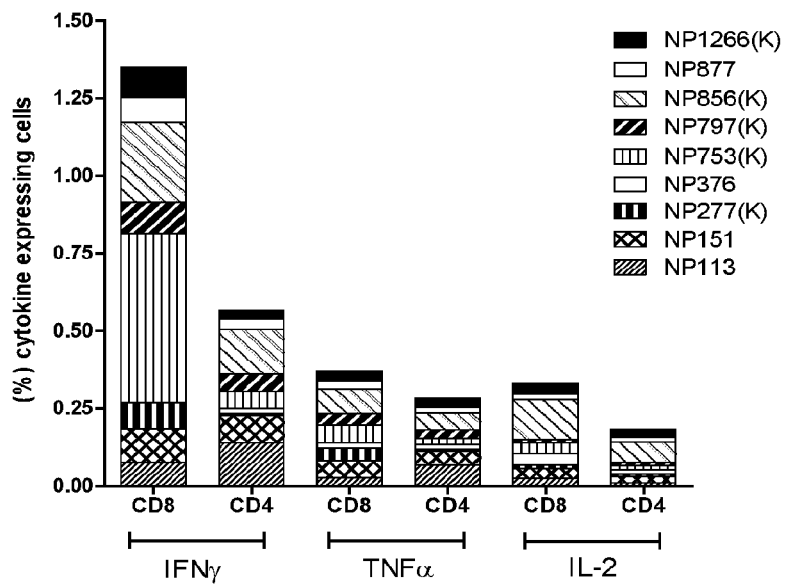
FIGS. 13A-13E show the frequency of cytokine-producing CD4+ and CD8+ T cell in PBMC from chronic HBV following stimulation with HBV derived peptides.
Figure 13B:
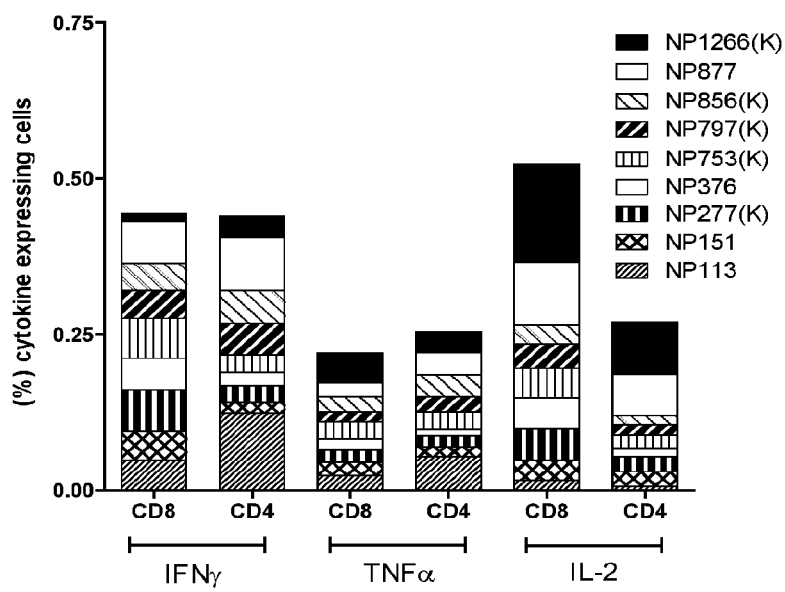
Figure 13C:
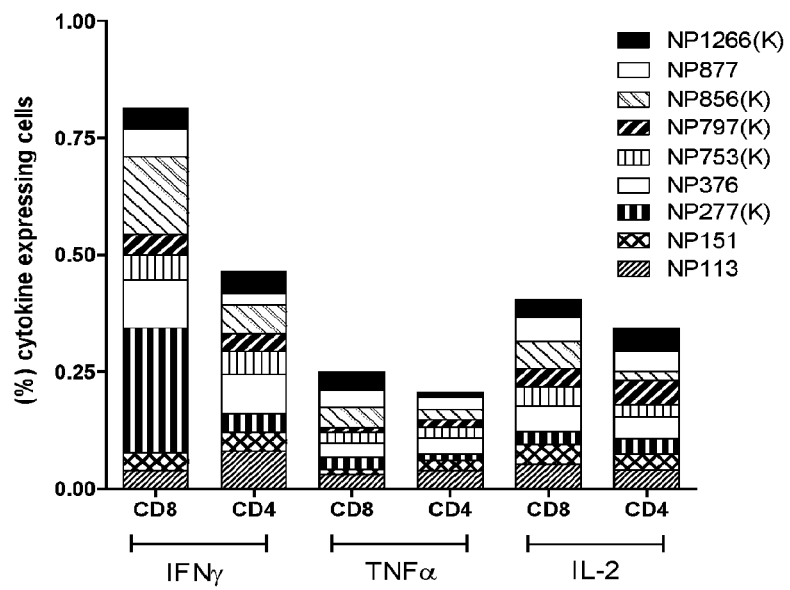
Figure 13D:
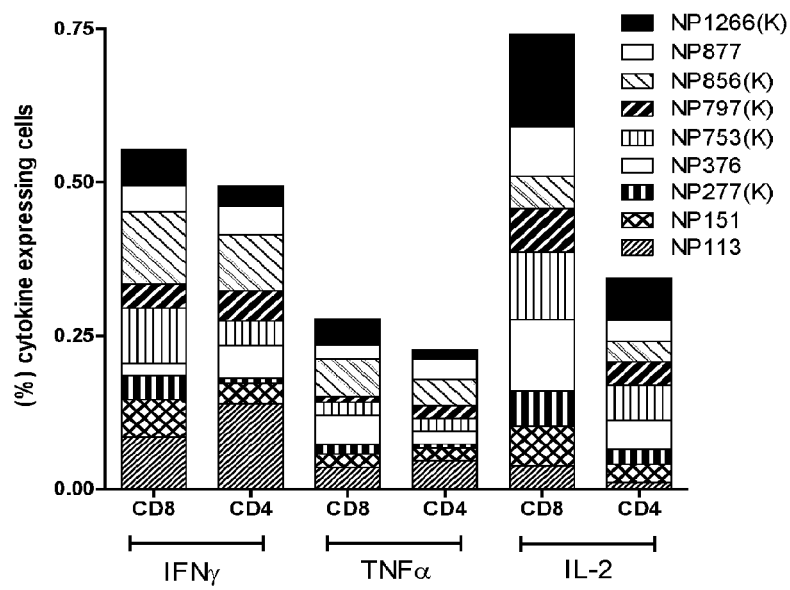
Figure 13E:
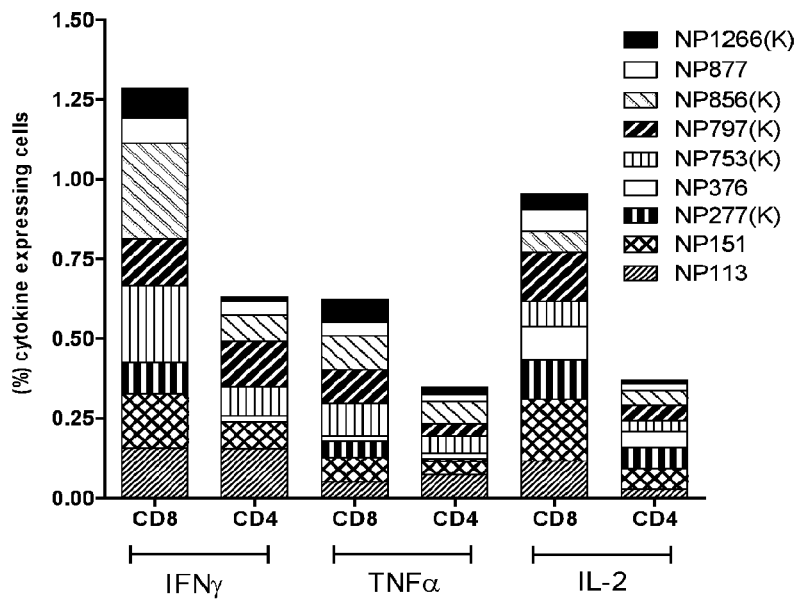

FIG. 12 shows that all peptides promote T cell responses across all ethnic groups tested. Peptides NP113, NP151, NP376, NP753(K), NP797(K), NP856(K) and NP877 promote the highest responses across all three ethnic groups compared to NP277(K) and NP1266(K).

In addition, all nine peptides show the ability to promote Th1 cytokine-producing CD4 and/or CD8 T cell responses as measured by intracellular cytokine staining across all HBV genotypes (FIGS. 13A-13E).

Example 6: Superiority of the Fluorocarbon-Conjugated Peptides Compared to Unconjugated Peptides in their Ability to Promote T Cell Responses In Vivo Methods and Materials The immunogenicity in mice of FP02.1 (containing nine fluorocarbon-conjugated peptides) was compared to NP02.1 (containing nine equivalent unconjugated peptides). Female BALB/c mice (n=7/group) were immunised intramuscularly with FP02.1 at a dose of 50 µg per peptide in a volume of 50 µL or with NP02.1 (containing the unconjugated HBV peptides (NP113, NP151, NP277(K), NP376, NP753(K), NP797(K), NP856(K), NP877 and NP1266(K)) at a equimolar dose (compared to FP02.1) of 43.8 µg per peptide in a volume of 50 µL. Mice were immunised on day 0 and sacrificed on day 14. Splenocytes were stimulated in vitro with 5 µg/mL/peptide of a mixture of each of the nine HBV peptides described in Example 3 for 18 hours in an ELISpot assay.

Alternatively, splenocytes were stimulated in vitro with 5 µg/mL/peptide of nine individual peptides for 18 hours in an ELISpot assay. The number of IFNγ+ spot forming cells (SFC) was counted. Plates then were washed with PBS, incubated with an IFNγ detection peroxidase-labelled antibody, followed by a substrate, according to the manufacturer's instructions. The developed spots were counted using an automated plate counting system (CTL Europe) to quantify the number of IFNγ+ SFCs.

Results

Figure 14:
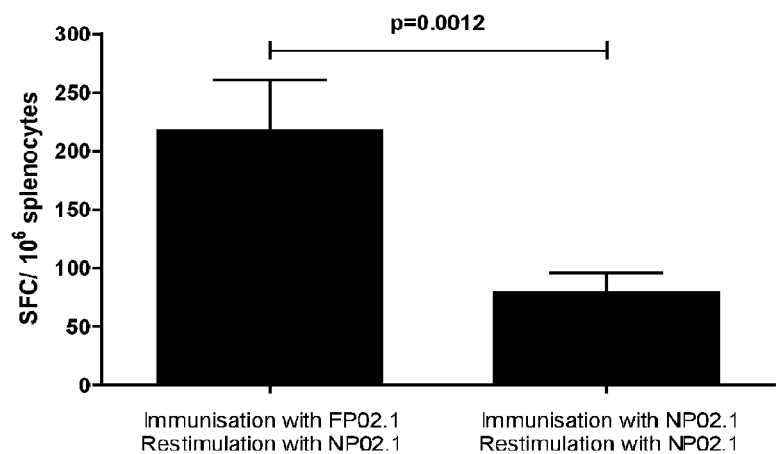
FIG. 14 shows IFNγ production by splenocytes from BALB/c mice (n=7) immunised with FP-02.1 or NP02.1. The graphic represents the number of IFNγ spot-forming cells per $10^6$ splenocytes measured in response to the 9 peptide components of the vaccines. Statistical analyses were performed using paired t tests, ns=not significant.
Figure 15:
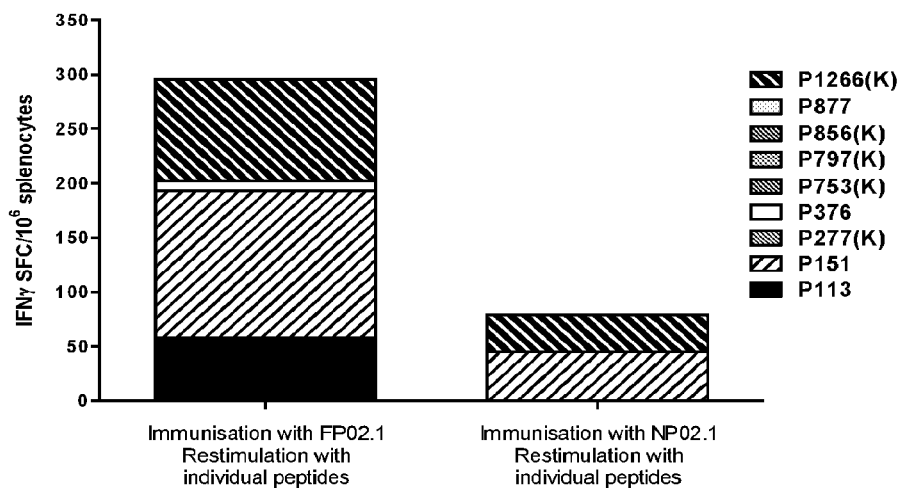
FIG. 15 shows IFNγ production by splenocytes from BALB/c mice (n=7) immunised with FP-02.1 or NP02.1. The graphic represents the number of IFNγ spot-forming cells per $10^6$ splenocytes measured in response each of the 9 peptide components of the vaccines. Bars represent cumulative median responses to each individual peptide.

Significantly higher magnitude T cell responses were observed in mice immunised with the mixture of fluorocarbon-conjugated peptides (FP02.1) compared to the equivalent mixture of unconjugated peptides (NP02.1) (see FIG. 14). Due to the MHC restriction in the syngeneic BALC/C model, immune responses were dominated by four out of the 9 peptides contained in the vaccine (peptides NP113, NP151, NP376 and NP1266(K); see FIG. 15).

Responses induced by FP02.1 were dominated by peptides NP113, NP151, NP376 and NP1266(K). Surprisingly, immune responses against peptide P113 and P376 were only observed with the formulation containing the fluorocarbon-conjugated peptides (see FIG. 15).

In conclusion, the conjugation of a fluorocarbon vector to the HBV derived peptide sequences promote higher and broader T cell responses compared to the equivalent unconjugated peptides.

Example 7: Fluorocarbon-Conjugated Peptides Promote a CTL/CD8+ T Cell Response

Methods and Materials

The quality of the immune response induced by FP02.1 (containing nine fluorocarbon-conjugated peptides) was evaluated in mice. Female BALB/c mice (n=7/group) were immunized intramuscularly with FP02.1 at a dose of 25 µg per peptide in a volume of 50 µL. Mice were immunised on day 0 and sacrificed on day 14.

Splenocytes were stimulated in vitro with either a CTL epitope derived from peptide NP113 (CTLI KYLPLDKGI) or a CTL epitope derived from NP151 (CTL 2 HYFQTRHYL) at concentrations ranging from $10^1$ to $10^{-9}$ µg/ml for 18 hours in an ELISpot assay. The number of IFNγ+ SFC was counted. Plates then were washed with PBS, incubated with an IFNγ detection peroxidase-labelled antibody, followed by a substrate, according to the manufacturer's instructions. The developed spots were counted using an automated plate counting system (CTL Europe) to quantify the number of IFNγ+ SFCs.

Results

Figure 16:
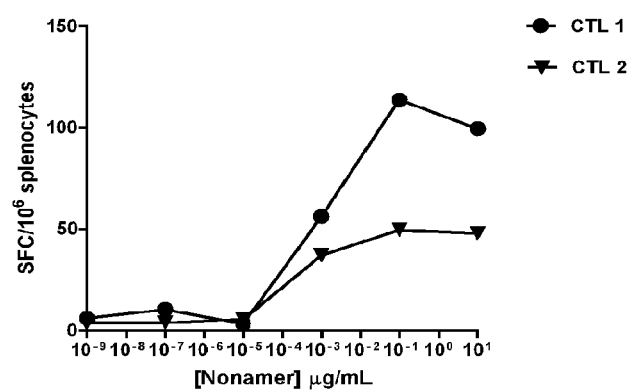
FIG. 16 shows that FP02.1 promotes T cell responses against CTL epitopes 5 restricted by MHC class I molecules after a single immunisation.

As shown in FIG. 16, FP02.1 promotes T cell responses against CTL epitopes restricted by MHC class I molecules after a single immunisation.

Example 8: Synergy Between Fluorocarbon-Peptides Contained in the Same Formulation Methods and Materials The immunogenicity of FA-P113 administered in mice alone or as part of a co-formulation with other fluorocarbon-conjugated peptides (FP02.1) was evaluated in mice. Female BALB/c mice (n=7/group) were immunised intramuscularly with FA-P113 at a dose of 25 µg or FP02.1 at a dose of 25 µg per peptide in a volume of 50 µL. Mice were immunised on day 0 and sacrificed on day 14. Splenocytes were stimulated in vitro with 5 µg/mL of NP113 (not conjugated to a fluorocarbon vector) for 18 hours in an ELISpot assay. The number of IFNγ+ SFC was counted. Plates then were washed with PBS, incubated with an IFNγ detection peroxidase-labeled antibody, followed by a substrate, according to the manufacturer's instructions. The developed spots were counted using an automated plate counting system (CTL Europe) to quantify the number of IFNγ+ SFCs.

Results

The results shown in Table 6 represent the number of nonamers derived from each HBV long peptide (NP113, NP151, NP277, NP376, NP753, NP797, NP856, NP877 and NP1266) having a binding score >=45% for each HLA allele. All long HBV peptides contain at least six epitopes having the ability to bind to at least 4 alleles. Any combination of six long peptides contains nonamer epitopes having the ability to bind to all alleles tested.

TABLE 6

Number of nonamers derived from each HBV long peptide (NP113, NP151, NP277(K), NP376, NP753(K), NP797(K), NP856(K), NP877 and NP1266(K)) having a binding score >= 45% for each HLA class I alleles. (a) represents the total number binding epitopes detected for each long peptide (b) represents the number of alleles for which positive binding was detected for each long peptide.

| Long peptide | HLA-A*0201 | HLA-A*0301 | HLA-A*1101 | HLA-A*2402 | HLA-B*0702 | HLA-B*0801 | HLA-B*3501 | Number of HLA binders (a) | Number of allele (b) |
|---|---|---|---|---|---|---|---|---|---|
| NP113 | 2 | 3 | 5 | 3 | 2 | 3 | 2 | 20 | 7 |
| NP797(K) | 6 | 1 | 1 | 5 | 4 | 3 | 2 | 22 | 7 |
| NP151 | 3 | 4 | 3 | 4 | 3 | 4 | 0 | 21 | 6 |
| NP376 | 8 | 0 | 1 | 10 | 4 | 6 | 6 | 35 | 6 |
| NP753(K) | 3 | 0 | 1 | 3 | 1 | 1 | 1 | 10 | 6 |
| NP1266(K) | 6 | 3 | 3 | 9 | 0 | 1 | 2 | 24 | 6 |
| NP277(K) | 6 | 0 | 0 | 5 | 3 | 1 | 3 | 18 | 5 |
| NP856(K) | 4 | 0 | 0 | 4 | 2 | 1 | 0 | 11 | 4 |
| NP877 | 2 | 0 | 0 | 2 | 1 | 1 | 0 | 6 | 4 |

Results

Figure 17:
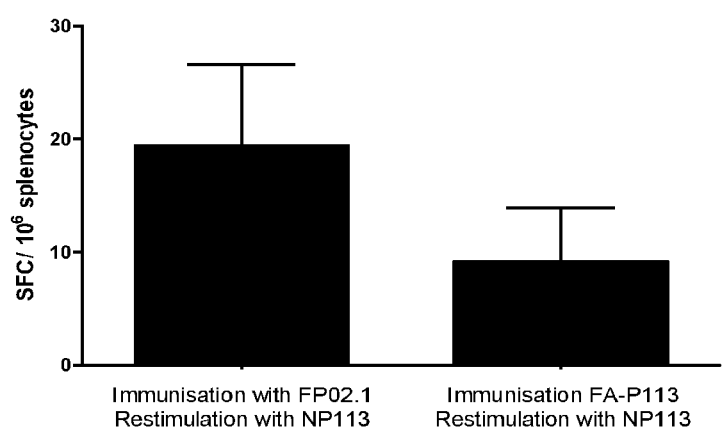
FIG. 17 shows IFNγ production by BALB/c mice immunised with FP-02.1 or NP02.1. Number of IFNγ SFC/$10^6$ splenocytes produced in response to a mixture of the nine peptides for each splenocyte population.

A higher magnitude of NP-113-specific T cell responses was observed in mice immunised with the mixture of fluorocarbon-conjugated peptides (FP02.1) than FA-P113 alone (see FIG. 17).

Example 9: Preferred HBV Peptides and Combinations Contain Epitopes Having the Ability to Bind to a Broad Range of HLA Class I Molecules Methods and Materials The ProImmune REVEAL binding assay was used to determine the ability of short peptides of nine amino-acids (derived from the HBV long peptides NP113, NP151, NP277(K), NP376, NP753(K), NP797(K), NP856(K), NP877 and NP1266(K)) to bind to one or more MHC class I alleles and stabilize the MHC-peptide complex. Detection is based on the presence or absence of the native conformation of the MHC-peptide complex. The highly frequent HLA class I alleles (HLA-A*0201, A*0301, A*1101, A*2402, B*0702, B*0801, and B*3501) were selected. Binding to MHC molecules was compared to that of a known T-cell epitope, a positive control peptide, with very strong binding properties. All potential nonamers for each HBV peptides (NP113, NP151, NP277(K), NP376, NP753 (K), NP797(K), NP856(K), NP877 and NP1266(K)) except those containing extra-lysines not present in the consensus HBV sequences were synthesised at a purity >90%. The score of the test peptide is reported quantitatively as a percentage of the signal generated by the positive control peptide, and the peptide is indicated as having a putative pass or fail result. Good binders are considered to be those peptides with scores 45% of the positive control as defined by ProImmune.

Example 10: Preferred HBV Peptides and Combinations Contain Epitopes Having the Ability to Bind to a Broad Range of HLA Class II Molecules Methods The ProImmune REVEAL® MHC-peptide binding assay was used to determine the ability of each HBV long peptide (NP113, NP151, NP277(K), NP376, NP753(K), NP797(K), NP856(K), NP877 and NP1266(K)) to bind one or more MHC class II allele and stabilise the MHC-peptide complex. The highly frequent HLA class II alleles HLA-DR1 (α1*01: 01; β1*01:01), HLA-DR15 (α1*01:01; β1*15:01), HLA-DR3 (α1*01:01; β1*03:01), HLA-DR4 (α1*01:01; β1*04: 01), HLA-DR11 (α1*01:01; β1*11:01), HLA-DR13 (α1*01:01; β1*13:01), and HLA-DR7 (α1*01:01; β1*07: 01) were selected. Each peptide was given a score relative to the positive control peptide, which is a known T-cell epitope. The score of the test peptide is reported quantitatively as a percentage of the signal generated by the positive control peptide, and the peptide is indicated as having a putative pass or fail result. Good binders are considered to be those peptides with scores >=15% of the positive control as defined by Proimmune.

Results

The results in Table 7 represent the binding score of each HBV long peptide (NP113, NP151, NP277(K), NP376, NP753(K), NP797(K), NP856(K), NP877 and NP1266(K)) across the range of HLA class II alleles. Six out of the nine HBV peptides bind to at least one HLA allele with a score >=15%. NP113, NP151 and NP376 bind to more than 3 different HLA class II alleles. Surprisingly, NP113 binds to a total 6 alleles.

The combination of peptides NP113 and NP877 binds to all HLA class II alleles tested.

TABLE 7

Binding of HBV peptides to a range of HLA class II molecules. Positive binding was defined as score >= 15% (a) represents the number of alleles for which positive binding was detected for each long peptide

| Long peptide | HLA-DR1 (α1*01:01; β1*01:01) | HLA-DR15 (α1*01:01; β1*15:01) | HLA-DR3 (α1*01:01; β1*03:0) | HLA-DP4 (α1*01:03; β1*04:01) | HLA-DR11 (α1*01:01; β1*11:01) | HLA-DR13 (α1*01:01; β1*13:01) | HLA-DR7 (α1*01:01; β1*07:01) | Number of allele (a) |
|---|---|---|---|---|---|---|---|---|
| NP113 | 54.44 | 28.04 | 49.98 | 33.51 | 52.86 | 0.00 | 99.17 | 6 |
| NP151 | 14.59 | 38.96 | 0.00 | 74.36 | 49.16 | 0.00 | 19.41 | 4 |
| NP277(K) | 0.49 | 0.18 | 0.10 | 36.19 | 1.25 | 0.00 | 0.01 | 1 |
| NP376 | 27.71 | 6.29 | 0.00 | 53.66 | 31.38 | 0.00 | 8.83 | 3 |
| NP753(K) | 0.11 | 0.00 | 0.00 | 0.65 | 1.51 | 0.00 | 0.00 | 0 |
| NP797(K) | 0.20 | 1.14 | 0.00 | 6.65 | 2.86 | 0.00 | 0.01 | 0 |
| NP856(K) | 2.33 | 5.71 | 0.13 | 10.72 | 0.33 | 0.00 | 0.40 | 0 |
| NP877 | 0.24 | 0.09 | 5.58 | 0.04 | 4.98 | 16.34 | 2.78 | 1 |
| NP1266(K) | 1.48 | 0.64 | 0.00 | 11.22 | 21.64 | 0.00 | 0.62 | 1 |

The invention claimed is:

1. A pharmaceutical composition comprising a combination of two or more fluorocarbon peptide constructs, wherein each construct comprises an immunogenic hepatitis B virus peptide sequence covalently attached to a vector for intracellular delivery of the peptide, wherein the vector comprises a chain comprising from 3 to 30 carbon atoms, at least one of which is substituted with fluorine, chlorine, bromine or iodine, and wherein the peptide is from 15 to 60 amino acids in length comprising at least 15 contiguous amino acids shown in any one of SEQ ID NOs: 1 to 4 or SEQ ID No: 55 or of a sequence having at least 90% identity to one of the sequences shown in SEQ ID NOs: 1 to 4 or SEQ ID NO: 55 wherein each peptide comprises at least one CD8+ T-cell epitope and at least one CD4+ T-cell epitope and wherein the peptide binds two or more HLA class I alleles.

2. The composition of claim 1, wherein at least one peptide further comprises one or more additional amino acid at the N-terminus and/or C-terminus to increase the net positive charge and/or to reduce hydrophobicity of the peptide.

3. The composition of claim 1, wherein said composition is capable of eliciting an immune response in PBMC from at least two individuals of different ethnicities and from two individuals infected with different HBV genotypes.

4. The composition of claim 3, wherein said composition is capable of eliciting an immune response in PBMC from two, three or all of: an individual infected with HBV genotype A, an individual infected with HBV genotype B, an individual infected with HBV genotype C and an individual infected with HBV genotype D.

5. The composition of claim 3, wherein said composition is capable of eliciting an immune response in PBMC from two, three or all of: an Oriental or Indian individual infected with HBV, a Caucasian individual infected with HBV and an African or Arabic individual infected with HBV.

6. The composition of claim 1, which further comprises HBc, HBe, or HBs antigen.

7. The composition of claim 1, which further comprises an adjuvant.

8. A method for treatment or prevention of HBV or hepatitis D virus (HDV) infection, comprising administering the composition of claim 1 to a patient in need thereof.

9. The method of claim 8, wherein the patient is HBeAg-negative.

10. The method of claim 8, wherein the patient is HBeAg-positive.

11. The method of claim 8, further comprising administering at least one of;

(i) interferon-alpha or nucleoside/nucleotide analogues (NUCs); or (ii) anti-PD1 blocking antibodies, anti-PD1L blocking antibodies, anti-LAG3 blocking antibodies, anti-TIM3 blocking antibodies, anti-CTLA4 blocking antibodies or cyclophosphamide.

12. A method for treatment or prevention of end-stage liver disease or hepatocellular carcinoma, comprising administering the composition of claim 1 to a patient in need thereof.

13. The composition of claim 1, wherein the combination of peptides are present in a solution at a concentration of about 0.1 mM to about 10 mM.

14. The composition of claim 1, wherein the composition is in a dried form.

15. The composition of claim 1, wherein each peptide is attached to a fluorocarbon chain having the structure $C_mF_n$—$C_yH_x$(Sp)-R, where m=3 to 30, n<=2m+1, y=0 to 15, x<=2y, (m+y)=3–30 and Sp is an optional spacer moiety and R is the peptide.

16. A pharmaceutical composition comprising a combination of peptides comprising a sequence shown in each of SEQ ID NOs: 24, 25, 28, 34, 33, 36, 37, 38 and 222, wherein each peptide is attached to a fluorocarbon chain having the structure $C_mF_n$—$C_yH_x$(Sp)-R, where m=3 to 30, n<=2m+1, y=0 to 15, x<=2y, (m+y)=3–30 and Sp is an optional spacer moiety and R is the peptide.

17. The composition of claim 16, wherein the fluorocarbon chain is selected from:

18. the composition of claim 16, wherein the fluorocarbon chain has the formula $C_8F_{17}(CH_2)_2$(Sp)-R.

19. A pharmaceutical composition comprising a combination of peptides comprising a sequence shown in each of SEQ ID NOs: 24, 25, 28, 34, 33, 36, 37, 38 and 222, wherein each peptide is attached to a fluorocarbon chain having the structure $C_8F_{17}$—$(CH_2)_2$(Sp)-R, where Sp is an optional spacer moiety and R is the peptide.

* * * * *